US00RE39355E

(19) United States
(12) Reissued Patent
Lee et al.

(10) Patent Number: US RE39,355 E
(45) Date of Reissued Patent: Oct. 17, 2006

(54) PREPARATION OF HUMAN IGF VIA RECOMBINANT DNA TECHNOLOGY

(75) Inventors: James M. Lee, San Bruno, CA (US); Axel Ullrich, Munich (DE)

(73) Assignee: Genetech, Inc., South San Francisco, CA (US)

(21) Appl. No.: 10/461,712

(22) Filed: Jun. 13, 2003

Related U.S. Patent Documents

Reissue of:
(64) Patent No.: 6,331,609
Issued: Dec. 18, 2001
Appl. No.: 08/464,361
Filed: Jun. 5, 1995

U.S. Applications:
(63) Continuation of application No. 06/506,078, filed on Jun. 20, 1983, now abandoned, which is a continuation-in-part of application No. 06/501,353, filed on Jun. 6, 1983, now abandoned.

(51) Int. Cl.
*C07K 14/65* (2006.01)

(52) U.S. Cl. ..... 530/324; 530/350; 530/399; 435/69.7

(58) Field of Classification Search ..... 530/324, 530/350, 399; 435/69.7
See application file for complete search history.

(56) References Cited

U.S. PATENT DOCUMENTS

| | | | | |
|---|---|---|---|---|
| 3,953,418 | A | * | 4/1976 | Yanaihara et al. |
| 4,110,322 | A | * | 8/1978 | Greven et al. |
| 4,342,832 | A | * | 8/1982 | Goeddel et al. |
| 4,350,764 | A | * | 9/1982 | Baxter et al. |
| 4,366,246 | A | * | 12/1982 | Riggs |
| 4,387,162 | A | * | 6/1983 | Aigle et al. |
| 4,411,994 | A | * | 10/1983 | Gilbert et al. |
| 4,425,437 | A | * | 1/1984 | Riggs |
| 4,431,740 | A | * | 2/1984 | Bell et al. |
| 4,440,859 | A | * | 4/1984 | Rutter et al. |
| 4,530,904 | A | * | 7/1985 | Hershberger et al. |
| 4,543,329 | A | * | 9/1985 | Daum et al. |
| 4,546,082 | A | * | 10/1985 | Kurjan et al. |
| 4,588,684 | A | * | 5/1986 | Brake |
| 4,652,525 | A | * | 3/1987 | Rutter et al. |
| 4,658,021 | A | * | 4/1987 | Goeddel et al. |
| 4,745,179 | A | * | 5/1988 | Ueda et al. ..... 530/350 |
| 5,015,575 | A | * | 5/1991 | Brake et al. |

FOREIGN PATENT DOCUMENTS

| | | | |
|---|---|---|---|
| CA | 1214739 | * | 12/1986 |
| EP | 022242 | * | 7/1979 |
| EP | 026598 | * | 4/1981 |
| EP | 046039 | * | 2/1982 |
| EP | 055945 | * | 7/1982 |
| EP | 075444 | * | 3/1983 |
| EP | 116201 | * | 8/1984 |
| EP | 121352 | * | 10/1984 |
| EP | 123228 | * | 10/1984 |
| EP | 123289 | * | 10/1984 |
| EP | 123294 | * | 10/1984 |
| EP | 123544 | * | 10/1984 |
| EP | 130166 | * | 1/1985 |
| EP | 135094 | * | 3/1985 |
| EP | 155655 | * | 9/1985 |
| EP | 189481 | * | 8/1986 |
| JP | 56-95199 | * | 8/1981 |
| JP | 57-200343 | * | 12/1982 |
| NL | 8302324 | * | 1/1985 |
| WO | WO 84/03103 | * | 8/1984 |

OTHER PUBLICATIONS

"Chiron's elegant, general purpose, rDNA yeast system. A breakthrough?" *Biotech News* 3(10):1–3 (May 15, 1983).
"Har "byggdes" Sveriges forsta konstgjorda gen" *Svdsvenska Dagbladet* (Feb. 1, 1983).
"Konstgjort arvsanlag framstallt vid Kabi" *Goteborgs–Posten* (Feb. 3, 1983).
Achstetter and Wolf, "Hormone processing and membrane–bound proteinases in yeast" *The EMBO Journal* 4(1):173–177 (1985).
Alberts, B. *Molecular Biology of the Cell,* New York and London:Garland Publishing, Inc. pps. 215 (1983).
Astell et al, "The sequence of DNAs coding for the mating type loci of *saccharomyces cerevisiae" Cell* 27:15–23 (1981).
Baum, R.M., "Enzyme chemistry set to advance as new techniques are applied" *Chemical and Engineering News* pps. 7–14 (Jul. 14, 1986).
Bell et al., "Nucleotide sequence of a cDNA clone encoding human preproinsulin" *Nature* 282:525–527 (1979).
Bell et al., "Sequence of a cDNA clone encoding human preproinsulin–like growth factor II" *Nature* 310:775–777 (1984).
Bradshaw and Niall, "Insulin–related growth factors" *TIBS* 3:274–278 (1978).
Brake et al, "α–Factor–directed synthesis and secretion of mature foreign proteins in *Saccharomyces cerevisiae" Proc. Natl. Acad. Sci* 81:4642–4646 (1984).
Brake et al., "Identification and Characterization of a Structural Gene for the Yeast Peptide Mating Pheromone, a–factor" *J. Cell. Biochem.* (abstract 1497) Supp. 7B (Apr. 29, 1983).
Brousseau et al., "Synthesis of a human insulin gene V. Enzymatic assembly, cloning and characterization of the human proinsulin DNA" *Gene* 17:279–289 (1982).
Carpenter, "Epidermal growth factor is a major growth–promoting agent in human milk" *Chemical Abstracts* (abstract No. 215932m) 93:96 (1980).

(Continued)

*Primary Examiner*—Marianne P. Allen
(74) *Attorney, Agent, or Firm*—Janet E. Hasak; Ginger R. Dreger; Heller Ehrman, LLP

(57) ABSTRACT

Human insulin-like growth factor is synthesized in recombinant cell culture by host cells transformed with expression vectors bearing DNA encoding human insulin-like growth factor.

1 Claim, 26 Drawing Sheets

OTHER PUBLICATIONS

Carpenter and Cohen, "Chapter 5—Epidermal Growth Factors" *Biochemical Actions of Hormones* (summarized in Chemical Abstracts, vol. 91 (11) 83626m (1979)), Academic Press, Inc. vol. V:203–247 (1978).

Carpenter et al., "Characterization of the binding of I–labeled epidermal growth factor to human fibroblasts" *J. Biol. Chemistry* 250(11):4297–4304 (Jun. 10, 1975).

Casabadan, "Transposition and Fusion of the lac Genes to Selected Promoters in *Escherichia coli* using Bacteriophage Lambda and Mu" *J. Mol. Biol.* 104:541–555 (1976).

Catanzaro et al., "Immunoscreening of Expression Clones Using Antibodies to Renin, EGF and NGF" *Manipulation and Expression of Genes in Eukaryotes,* Nagley et al. pps. 11–12 (1983).

Chan et al., "Cell–free synthesis of rat preproinsulins: Characterization and partial amino acid sequence determination" *Proc. Natl. Acad. Sci. USA* 73(6):1964–1968 (1976).

City of Hope; Genentech, Inc., "Research Scientists Synthesize Genes to "Command" Laboratory Bacteria to Manufacture Human Insulin" *Press Release* (Sep. 6, 1978).

Crea et al., "Chemical synthesis of genes for human insulin"0 *Proc. Natl. Acad. Sci. USA* 75:5765–5769 (1978).

Davis and Tai, "The mechanism of protein secretion across membranes" *Nature* 283:433–438 (1980).

Dayhoff, "Table of Contents, Preface, Data Section, Protein Data Introduction, Hormones, Active Peptides and Toxins" *Atlas of Protein Sequence and Structure,* Silver Spring: The National Biomedical Research Foundation vol. 5:vii–xxx, D1–D6, D176, D177, D2 (1972).

Dayhoff, "Table of Contents, Preface, Protein Data Introduction, Hormones and Active Peptides" *Atlas of Protein Sequence and Structure,* Silver Spring:The National Biomedical Research Foundation vol. 5(Supp. 3):vii–xxii, 25–28, 145–164 (1978).

Dayhoff, "Table of Contents, Preface, Protein Data Introduction, Hormones and Active Peptides" *Atlas of Protein Sequence and Structure,* Washington, DC:National Biomedical Research Foundation vol. 5(Supp. 2):vii–xx, 14, 21–24, 113–145 (1976).

deHaen et al., "Characterization of Proinsulin–Insulin Intermediates in Human Plasma" *J. Clin. Invest.* 62:727–737 (1978).

Dicker et al., "Similarities between fibroblast–derived growth factor and platelet–derived growth factor" *Chemical Abstracts* (abstract No. 201393r) 95:454 (1981).

Docherty et al., "Post–translational proteolysis in polypeptide hormone biosynthesis" *Annu Rev Physiol* 44:625–638 (1982).

Edge et al., "Total Synthesis of a Human Leukocyte Interferon Gene" *Nature* 292:756–762 (1981).

Estell et al., "Engineering an enzyme by site–directed mutagenesis to be resistant to chemical oxidation" *J. Biol. Chemistry* 260(11):6518–6521 (1985).

Frank and Chance, "Two Routes for Producing Human Insulin Utilizing Recombinant DNA Technology" *Munch. med. Wschr.* 125:14–20 (1983).

Gait, "Synthetic genes for human insulin" *Nature* 277:429–430 (1979).

Genentech, Inc., "First Successful Laboratory Production of Human Insulin Announced" *Press Release* (Sep. 6, 1978).

Gill et al. *Recombinant DNA,* Walton, A.G. pps. 213–227 (1981).

Goeddel et al., "Expression in *Escherichia coli* of Chemically Synthesized Genes for Human Insulin" *Proc. Natl. Acad. Sci. USA* 76(1):106–110 (1979).

Gregory, H., "Isolation and structure of urogastrone and its relationship to epidermal growth factor" *Nature* 257:325–327 (Sep. 25, 1975).

Grosjean and Fiers, "Preferential codon usage in prokaryotic genes: the optimal codon–anticodon interaction energy and the selective codon usage in efficiently expressed genes" *Gene* 18:199–209 (1982).

Higuchi et al., "A general method for cloning eukaryotic structural gene sequences" *Proc. Natl. Acad. Sci. USA* 73(9):3146–3150 (1976).

Hinnen et al., "High expression and secretion of foreign proteins in yeast" *Chemical Abstracts* (abstract No. 40931k) 102:150 (1985).

Hitzeman et al., "Expression of a Human Gene for Interferon in Yeast" *Nature* 293:717–722 (1981).

Hitzeman et al., "Secretion of human interferons by yeast" *Science* 219:620–625 (1983).

Hsiung et al., "Synthesis of human insulin gene. Part I. Development of reversed–phase chromatography in the modified triester method. Its application in the rapid and efficient synthesis of eight deoxyriboligonucleotides fragments constituting human insulin A DNA" *Nucl. Acids Res.* 6:1371–1385 (1979).

Hsiung et al., "Synthesis of human insulin gene. Part III. Chemical synthesis of 5'–phosphomonoester group containing deoxyribooligonucleotides by the modified phosphotriester method. Its application . . . seventeen fragments constituting human insulin C–chain DNA" *Nucl. Acids Res.* 8:5753–5765 (1980).

Humbel, "Insulin–like growth factors I and II" *European Journal of Biochemistry* 190:445–462 (1990).

Itakura et al., "Expression in *Escherichia coli* of a Chemically Synthesized Gene for the Hormone Somatostatin" *Science* 198:1056–1063 (1977).

Jansen et al., "Sequence of cDNA encoding human insulin–like growth factor I precursor" *Nature* 306:609–611 (1984).

Julius et al., "Isolation of the putative structural gene for the lysine–arginine–cleaving endopeptidase required for processing of yeast prepro–Á–factor" *Cell* 37:1075–1089 (1984).

Kadonaga et al., "The role of the β–lactamase signal sequence in the secretion of proteins by *Escherichia coli*" *Journal of Biological Chemistry* 259(4):2149–2154 (1984).

Kemmler et al., "Studies on the Conversion of Proinsulin to Insulin" *Journal of Biological Chemistry* 246(22):6786–6791 (1971).

Keshet et al, "Cloning of bovine growth hormone gene and its expression in bacteria" *Nucleic Acids Research* 9:19–30 (1981).

Kurjan et al., "Structure of a yeast pheromone gene (MFα) : a putative α–factor precursor contains four tandem copies of mature α–factor" *Cell* 30:933–973 (1982).

Li et al., "Total synthesis of insulin–like growth factor I (somatomedin C)" *Proc. Natl. Acad. Sci. USA* 80:2216–2220 (1983).

Lomedico et al., "Preparation of pancreatic mRNA: cell–free translation of an insulin–immunoreactive polypeptide" *Nucl. Acids Res.* 3(2):381–391 (1976).

Maniatis et al., "Expression of Eukaryotic Genes" *Molecular Cloning: A Laboratory Manual,* 1st edition, Cold Spring Harbor:Cold Spring Harbor Laboratory Press pps. 412–413 (1982).

Maniatis et al., "Preface, Contents, and List of References" *Molecular Cloning: A Laboratory Manual,* 1st edition, Cold Spring Harbor:Cold Spring Harbor Laboratory Press pps. iii–x; 507–520 (1983).

Mercereau–Puijalon et al. *Expression of Eukaryotic Viral & Cellular Genes,* Pettersson et al. pps. 295–303 (1981).

Mercereau–Puijalon et al., "Synthesis of a Chicken Ovalbumin–like Protein in the Yeast *Saccharomyces Cerevisiae" Gene* 11:163–167 (1980).

Merryweather et al. *Federation Proceedings* (AB#1161) 42(7):1956 (May 1, 1983).

Miller et al., "Synthesis of Biologically Active Proteins by Recombinant DNA Technology" *Drug Development Research* 1:435–454 (1981).

Mizuno and Matsuo, "A novel protease from yeast with specificity towards paired basic residues" *Nature* 309:558–560 (1984).

Mullenbach et al. *Amer. Soc. Biol. Chemists, 74th Annual Meeting,* San Francisco, CA (Poster Jun. 5, 1983).

Mullenbach et al., "The Chemical Synthesis, Molecular Cloning and Expression in Yeast of Genes Coding for Human Insulin–Like Growth Factors" *Federation Proceedings* (AB#434) 42(7):1832 (May 1, 1983).

Narang et al., "Synthesis of the human insulin gene. Part IV. New synthetic deoxyriboligonucleotide adaptors and primter for DNA cloning and sequence analysis" *Nucl. Acids Res.* Symp Series. 7:377–385 (1980).

O'Farrell et al., "Regulated Expression by Readthrough Translation from a Plasmid–Encoded beta–Galactosidase" *J. Bacteriology* 134(2):645–654 (1978).

Ohsuye et al., "Expression of chemically synthesized α–neo–endorphin gene fused to *E. coli* alkaline phosphatase" *Nucl. Acids Res.* 11(5):1283–1295 (1983).

Oyer et al., "Studies on Human Proinsulin" *Journal of Biological Chemistry* 246(5):1375–1386 (1971).

Polisky et al., "A plasmid cloning vehicle allowing regulated expression of eukaryotic DNA in bacteria" *Proc. Natl. Acad. Sci. USA* 73:3900–3904 (1976).

Riggs et al., "Synthesis, Cloning, and Expression of Hormone Genes in *Escherichia coli" Recent Prog. in Hormone Res.* 16:261–274 (1980).

Rinderknecht and Humbel, "The amino acid sequence of human insulin–like growth factor I and its structural homology with proinsulin" *Journal of Biological Chemistry* 253(8):2769–2776 (1978).

Rinderknecht and Humbel, "Amino–terminal sequences of two polypeptides from human serum with nonsuppressible insulin–like and cell–growth–promoting activities: Evidence for structural homology with insulin B chain" *Proc. Natl. Acad. Sci. USA* 73(12):4379–4381 (1976).

Rinderknecht and Humbel, "Polypeptides with nonsuppressible insulin–like and cell–growth promoting activities in human serum: isolation, chemical characterization, and some biological properties of forms I and II" *Proc. Natl. Acad. Sci USA* 73(3):2365–2369 (1976).

Rinderknecht et al., "Primary structure of human insulin–like growth factor II" *FEBS Letters* 89(2):283–286 (1978).

Roberts, T., "A lac Promoter System for the Overexpression of Prokaryotic and Eukaryotic Genes in *E. coli" Promoters: Structure and Function,* Rodriguez et al. (eds.). Praeger Scientific pps. 452–461 (1982).

Rossi et al., "An Alternate Method for Synthesis of Double–stranded DNA Segments" *Journal of Biological Chemistry* 257(16):9226–9229 (1982).

Rutter, "Production of "Valuable" Proteins in Alternate Biological Hosts" *Recombinant DNA and Genetic Experimentation,* Morgan and Whelan, Oxford:Pergamon Press pps. 123–128 (1979).

Schoenle et al., "Insulin–like growth factor I stimulates growth in hypophysectomized rats" *Nature* 296:252–253 (1982).

Server and Shooter, "Nerve Growth Factor" *Adv. Protein Chem.* 31:339–409 (1977).

Shine et al., "Expression of cloned β–endorphin gene sequences by *Escherichia coli" Nature* 285:456–461 (1980).

Stebbing, "Activity of cloned gene products in animal systems" *Miami Winter Symposia* 19:445–447 (1982).

Steiner, "Insulin Today" *Diabetes* 26:322–340 (1977).

Steiner et al., "Discussion of Jackson & Blobel: Canine pancreatic signal peptidase" *Annals of the NY Acad. Sci.* 343(1):403–404 (1980).

Steiner et al., "Insulin Biosynthesis: Evidence for a Precursor" *Science* 157:697–700 (1967).

Steiner et al., "New aspects of insulin biosynthesis" pps. 9–19 (1979).

Suggs et al., "Use of Synthetic Oligonucleotides as Hybridization Probes: Isolation of Cloned cDNA Sequences for Human $\beta_2$ Microglobulin" *Proc. Natl. Acad. Sci. USA* 78(11):6613–6617 (Nov. 1981).

Sung et al., "Synthesis of the human insulin gene. Part II. Further improvements in the modified phosphotriester method and the synthesis of seventeen deoxyribooligonucleotide fragments constituting human insulin chains B and mini–C DNA" *Nucl. Acids Res.* 7:2199–2212 (1979).

Sures et al., "Nucleotide sequence of human preproinsulin complementary DNA" *Science* 208:57–59 (1980).

Tacon et al., "The construction and characterisation of plasmid vectors suitable for the expression of all DNA phases under the control of the *E. coli* tryptophan promoter" *Molecular & General Genetics* 177(3):427–438 (1980).

Talmadge et al., "Eukaryotic Signal Sequence Transports Insulin Antigen in *Escherichia Coli" Proc. Natl. Acad. Sci. USA* 77(6):3369–3373 (1980).

Taniguchi et al., "Expression of the Human Fibroblast Interferon Gene in *Escherichia Coli" Proc. Natl. Acad. Sci. USA* 77(9):5230–5233 (1980).

Taniguchi et al., "Structure and expression of a cloned cDNA for human interleukin–2" *Nature* 302(24):305–309 (1983).

Taylor et al, "Epidermal Growth Factor" *J. Biol. Chemistry* 247:5928–5934 (1972).

Ullrich et al., "A bacterial clone synthesizing proinsulin" *Proc. Natl. Acad. Sci. USA* 75(8):3727–3731 (1978).

Ullrich et al., "Rat insulin genes: construction of plasmids containing the coding sequences" *Science* 196:1313–1319 (1977).

Valenzuela et al., "Is sequence conservation in interferons due to selection for functional proteins?" *Nature* 313:698–700 (Feb. 1985).

Wells and Powers, "In vivo formation and stability of engineered disulfide bonds in subtilisin" *J. Biol. Chemistry* 261(14):6564–6570 (May 15, 1986).
Wetzel et al., "Expression in *escherichia coli* of a chemically synthesized gene for a "mini–C" analog of human proinsulin" *Gene* 16:63–71 (1981).
Williams et al., "Cytoplasmic inclusion bodies in *escherichia coli* producing biosynthetic human insulin proteins" *Science* 215:687–689 (1982).
Woods et al., "Isolation of cDNA clones for the human complement protein factor B, a Class III Major Histocompatibility Complex Gene Product." *Proc. Natl. Sci. USA* 79:5661–5665 (Sep. 1982).
Wunsch et al., "Studies on Enzymatic Methods for Processing Hybrid Proteins Produced by Recombinant DNA Technology" *Hoppe–Seyler's Z. Physiol. Chem.* 362:1285–1287 (1981).
Zapf and Froesch, "Radioimmunological determination of insulinlike growth factors I and II in normal subjects and in patients with growth disorders and extrapancreatic tumor hypoglycemia" *Chemical Abstracts* (abstract No. 218639y) 95:385 (1981).
Zapf et al., "Insulin–like growth factors I and II: some biological actions and receptor binding characteristics of two purified constituents of nonsuppressible insulin–like activity of human serum" *Chemical Abstracts* (abstract No. 140765r) 89:78 (1978).
Bishop, "Scientists Use Bacteria to Produce Insulin in Step Toward Better Care for Diabetics" *The Wall Street Journal* pps. 14 (Jun. 12, 1978).
Lacy et al., "Method for the Isolation of Intact Islets of Langerhans from the Rat Pancreas" *Diabetes* 16:35–39 (1967).
Nichol and Smith, "Amino–Acid Sequence of Human Insulin" *Nature* 181:483–485 (1960).
Steiner, "Concluding remarks" *Proinsulin, Insulin, C–Peptide,* Baba et al., Amsterdam–Oxford:Excerpta Medica pps. 449–452 (1979).
Ullrich et al., "The structure and expression of the insulin gene" *Proinsulin, Insulin, C–Peptide,* Baba et al., Amsterdam–Oxford:Excerpta Medica pps. 20–26 (1979).
Villa–Komaroff et al., "A bacterial clone synthesizing proinsulin" *Proc. Natl. Acad. Sci. USA* 75(8):3727–3731 (1978).
Weinstein, "A Generalized Homology Correlation for Various Hormones and Proteins" *Experientia* 28:1517–1522 (1972).
Yanaihara et al., "Syntheses of C–peptides and human proinsulin" *Diabetes* 27:149–160 (1978).
Horner and Hintz, "Further Comparisons of the [$^{125}$I] Somatomedin A and the [$^{125}$I] Somatomedin C Radioreceptor Assays of Somatomedin Peptide" *J. Clin. Endocrinol. Metab.* 48(6):959–963 (1979).
Horner et al., "Comparison of [$^{125}$Y] Somatomedin A and [$^{125}$I] Somatomedin C Radioreceptor Assays for Somatomedin Peptide Content in Whole and Acid–Chromatographed Plasma" *J. Clin. Endocrinol. Metab.* 47(6):1287–1294 (1978).
Klapper et al., "Sequence Analysis of Somatomedin–C: Confirmation of Identity With Insulin–Like Growth Factor I" *Endocrinology* 112(6):2215–2217 (1983).
Svoboda et al., "Purification of Somatomedin–C from Human Plasma: Chemical and Biological Properties, Partial Sequence Analysis, and Relationship to Other Somatomedins" *Biochemistry* 19:790–797 (1980).
Chan et al., "Biosynthesis and Periplasmic Segregation of Human Proinsulin in *Escherichia coli" Proc. Natl. Acad. Sci. USA* 78(9):5401–5405 (1981).
*Protein, Nucleic Acid and Enzyme ISSN* 28(14):1480–1499 (Dec. 1983).
Hammarberg, B. et al., *PNAS,* 86:4367–4371, 1989.*
Hammarberg, B. et al., *J. of Biotechnology,* 14:423–438, 1990.*
Rhee, H. J. et al., *J. of Biotechnology,* 13:293–304, 1990.*

* cited by examiner

Chemically Synthesized DNA - IGF-1

Fig. 1.

IGF-1 LEFT HALF 1L (43-mer)

AGTTCTGATTTCGAATTCTATGGGTCCGGAAACTCTGTGCGGC

GACACGCCGCGACTCGACCAACTGCGAGACGTCTTAGTCTTGA 3L (43-mer)

2L (46-mer)

AGTTCTGATTCTGCAGTTCGTATGTGGTGATCGAGGCTTCTACTTC

GAAGATGAAGTTGTTTGGCTGACCCATGCCTAGGAGTTAGTCTTGA 4L (46-mer)

IGF-1 RIGHT HALF 1R (46-mer)

GACTGACTTCTGGATCCTCCTCTCGTCGTGCTCCGCAAACCGGCAT

TTGGCCGTAGCAACTACTTACGACAAAAGCCAGGACATTCAGTCAG 3R (46-mer)

2R (54-mer)

TGACTGACTTGGTCCTGTGACCTTCGCCGTCTGGAAATGTACTGCGCTCCGCTG

CGAGGCGACTTTGGCCGATTCAGACGTATCAGCTGAGTTCAGTCAG 4R (46-mer)

DNA Polymerase I Synthesized Double Stranded DNAs

Fig. 2.

IGF-1 LEFT HALF 12 additional bases — 9 additional bases 1 2 3 4 5 6 7 8 9 10 11 12 13 14 15

IniGlyProGluThrLeuCysGlyAlaGluLeuValAspAlaLeuGln

Part 1

AGTTCTGATTTCGAATTCTATGGGTCCGGAAACTCTGTGCGGCGCTGAGCTGGTTGACGCTCTGCAGAATCAGAACT

TCAAGACTAAAGCTTAAGATACCCAGGCCTTTGAGACACGCCGCGACTCGACCAACTGCGAGACGTCTTAGTCTTGA

EcoRI PstI 11 additional bases — 12 additional bases 15 16 17 18 19 20 21 22 23 24 25 26 27 28 29 30 31 32

GlnPheValCysGlyAspArgGlyPheTyrPheAsnLysProThrGlyTyrGly

Part 2

AGTTCTGATTCTGCAGTTCGTATGTGGTGATCGAGGCTTCTACTTCAACAAACCGACTGGGTACGGATCCTCAATCAGAACT

TCAAGACTAAGACGTCAAGCATACACCACTAGCTCCGAAGATGAAGTTGTTTGGCTGACCCATGCCTAGGAGTTAGTCTTGA

PstI BamHI

IGF-1 RIGHT HALF 11 additional bases — 12 additional bases 33 34 35 36 37 38 39 40 41 42 43 44 45 46 47 48 49 50 51

SerSerSerArgArgAlaProGlnThrGlyIleValAspGluCysCysPheArgSer

Part 3

GACTGACTTCTGGATCCTCCTCTCGTCGTGCTCCGCAAACCGGCATCGTTGATGAATGCTGTTTTCGGTCCTGTAAGTCAGTC

CTGACTGAAGACCTAGGAGGAGAGCAGCACGAGGCGTTTGGCCGTAGCAACTACTTACGACAAAAGCCAGGACATTCAGTCAG

BamHI AvaII 10 additional bases — 11 additional bases 51 52 53 54 55 56 57 58 59 60 61 62 63 64 65 66 67 68 69 70

SerCysAspLeuArgArgLeuGluMetTyrCysAlaProLeuLysProAlaLysSerAlaTer

Part 4

TGACTGACTTGGTCCTGTGACCTTCGCCGTCTGGAAATGTACTGCGCTCCGCTGAAACCGGCTAAGTCTGCATAGTCGACTCAAGTCAGTC

ACTGACTGAACCAGGACACTGGAAGCGGCAGACCTTTACATGACGCGAGGCGACTTTGGCCGATTCAGACGTATCAGCTGAGTTCAGTCAG

AvaII SalI

IGF-1 LEFT HALF

Part 1

1 2 3 4 5 6 7 8 9 10 11 12 13 14 15
IniGlyProGluThrLeuCysGlyAlaGluLeuValAspAlaLeuGln
AATTCTATGGGTCCGGAAACTCTGTGCGGCGCTGAGCTGGTTGACGCTCTGCAG
GATACCCAGGCCTTTGAGACACGCCGCGACTCGACCAACTGCGAGA
EcoRI PstI

Part 2

16 17 18 19 20 21 22 23 24 25 26 27 28 29 30 31
PheValCysGlyAspArgGlyPheTyrPheAsnLysProThrGlyTyr
TTCGTATGTGGTGATCGAGGCTTCTACTTCAACAAACCGACTGGGTAC
CGTCAAGCATACACCACTAGCTCCGAAGATGAAGTTGTTTGGCTGACCCATGCCTAG
PstI BamHI

Fig. 3.

IGF-1 RIGHT HALF

Part 3

33 34 35 36 37 38 39 40 41 42 43 44 45 46 47 48 49 50 51
SerSerSerArgArgAlaProGlnThrGlyIleValAspGluCysCysPheArgSer
GACTGACTTCTGGATCCTCCTCTCGTCGTGCTCCGCAAACCGGCATCGTTGATGAATGCTGTTTTCGGTCCTGTAAGTCAGTCCCCCCCCCCCCCCCCC
CCCCCCCCCCCCCCCCTGACTGAAGACCTAGGAGGAGAGCAGCACGAGGCGTTTGGCCGTAGCAACTACTTACGACAAAAGCCAGGACATTCAGTCAG
BamHI AvaII

Part 4

51 52 53 54 55 56 57 58 59 60 61 62 63 64 65 66 67 68 69 70
SerCysAspLeuArgArgLeuGluMetTyrCysAlaProLeuLysProAlaLysSerAlaTer
TGACTGACTTGGTCCTGTGACCTTCGCCGTCTGGAAATGTACTGCGCTCCGCTGAAACCGGCTAAGTCTGCATAGTCGACTCAAGTCAGTCCCCCCCCCCCCCCCCC
CCCCCCCCCCCCCCCCACTGACTGAACCAGGACACTGGAAGCGGCAGACCTTTACATGACGCGAGGCGACTTTGGCCGATTCAGACGTATCAGCTGAGTTCAGTCAG
AvaII SalI

Fig. 5.

Fig. 7.

```
met lys ala ile phe val leu lys gly ser leu asp arg asp leu asp ser arg ile glu
ATG AAA GCA ATT TTC GTA CTG AAA GGT TCA CTG GAC AGA GAT CTC GAC AGC CGT ATT GAA

leu glu met arg thr asp his lys glu leu ser glu his leu met leu val asp leu ala
CTG GAA ATG CGT ACC GAT CAT AAA GAG CTG TCT GAA CAT CTG ATG CTG GTT GAT CTC GCC

arg asn asp leu ala arg ile cys thr pro gly ser arg tyr val ala asp leu thr lys
CGT AAT GAT CTG GCA CGC ATT TGC ACC CCC GGC AGC CGC TAC GTC GCC GAT CTC ACC AAA

val asp arg tyr ser tyr val met his leu val ser arg val val gly glu leu arg his
GTT GAC CGT TAT TCC TAT GTG ATG CAC CTC GTC TCT CGC GTA GTC GGC GAA CTG CGT CAC

asp leu asp ala leu his ala tyr arg ala cys met asn met gly thr leu ser gly ala
GAT CTT GAC GCC CTG CAC GCT TAT CGC GCC TGT ATG AAT ATG GGG ACG TTA AGC GGT GCG

pro lys val arg ala met gln leu ile ala glu ala glu gly arg arg arg gly ser tyr
CCG AAA GTA CGC GCT ATG CAG TTA ATT GCC GAG GCG GAA GGT CGT CGC CGC GGC AGC TAC

gly gly ala val gly tyr phe thr ala his gly asp leu asp thr cys ile val ile arg
GGC GGC GCG GTA GGT TAT TTC ACC GCG CAT GGC GAT CTC GAC ACC TGC ATT GTG ATC CGC

ser ala leu val glu asn gly ile ala thr val gln ala gly ala gly val val leu asp
TCG GCG CTG GTG GAA AAC GGT ATC GCC ACC GTG CAA GCG GGT GCT GGT GTA GTC CTT GAT

ser val pro gln ser glu ala asp glu thr arg asn lys ala arg ala val leu arg ala
TCT GTT CCG CAG TCG GAA GCC GAC GAA ACC CGT AAC AAA GCC CGC GCT GTA CTG CGC GCT

ile ala thr ala his his ala gln glu phe pro ala gly pro glu thr leu cys gly ala
ATT GCC ACC GCG CAT CAT GCA CAG GAA TTC CCT GCC GGT CCG GAA ACT CTG TGC GGC GCT

glu leu val asp ala leu gln phe val cys gly asp arg gly phe tyr phe asn lys pro
GAG CTG GTT GAC GCT CTG CAG TTC GTA TGT GGT GAT CGA GGC TTC TAC TTC AAC AAA CCG

thr gly tyr gly ser ser ser arg arg ala pro gln thr gly ile val asp glu cys cys
ACT GGG TAC GGA TCC TCC TCT CGT CGT GCT CCG CAA ACC GGC ATC GTT GAT GAA TGC TGT

phe arg ser cys asp leu arg arg leu glu met tyr cys ala pro leu lys pro ala lys
TTT CGG TCC TGT GAC CTT CGC CGT CTG GAA ATG TAC TGC GCT CCG CTG AAA CCG GCT AAG

ser ala AM
TCT GCA TAG TCGACGTACATGAA
```

Translated Mol. Weight = 28671.51

Underscored - Mature Human IGF-1

Boxed - Collagenase Recognition Site sLE-IGF-1 Fusion Protein

Fig. 8.

```
  1                                       10
met lys ala ile phe val leu lys gly ser leu asp arg asp pro glu phe
ATG AAA GCA ATT TTC GTA CTG AAA GGT TCA CTG GAC AGA GAT CCA GAA TTC

        20                                      30
pro ala gly pro glu thr leu cys gly ala glu leu val asp ala leu gln phe val cys
CCT GCC GGT CCG GAA ACT CTG TGC GGC GCT GAG CTG GTT GAC GCT CTG CAG TTC GTA TGT

        40                                      50
gly asp arg gly phe tyr phe asn lys pro thr gly tyr gly ser ser ser arg arg ala
GGT GAT CGA GGC TTC TAC TTC AAC AAA CCG ACT GGG TAC GGA TCC TCC TCT CGT CGT GCT

        60                                      70
pro gln thr gly ile val asp glu cys cys phe arg ser cys asp leu arg arg leu glu
CCG CAA ACC GGC ATC GTT GAT GAA TGC TGT TTT CGG TCC TGT GAC CTT CGC CGT CTG GAA

        80                                  89
met tyr cys ala pro leu lys pro ala lys ser ala AM
ATG TAC TGC GCT CCG CTG AAA CCG GCT AAG TCT GCA TAG
```

Underscored - Mature Human IGF-1

Boxed - Collagenase Recognition Site

Yeast prepro α factor - IGF-1

Fig. 10.

```
met arg phe pro ser ile phe ser ala val leu phe ala ala ser ser ala leu ala ala
ATG AGA TTT CCT TCA ATT TTT AGT GCA GTT TTA TTC GCA GCA TCC TCC GCA TTA GCT GCT

pro val asn thr thr thr glu asp glu thr ala gln ile pro ala glu ala val ile gly
CCA GTC AAC ACT ACA ACA GAA GAT GAA ACG GCA CAA ATT CCG GCT GAA GCT GTC ATC GGT

tyr ser asp leu glu gly asp phe asp val ala val leu pro phe ser asn ser thr asn
TAC TCA GAT TTA GAA GGG GAT TTC GAT GTT GCT GTT TTG CCA TTT TCC AAC AGC ACA AAT

asn gly leu leu phe ile asn thr thr ile ala ser ile ala ala lys glu glu gly val
AAC GGG TTA TTG TTT ATA AAT ACT ACT ATT GCC AGC ATT GCT GCT AAA GAA GAA GGG GTA

ser leu asp lys arg glu ala glu ala leu glu phe pro ala gly pro glu thr leu cys
TCT TTG GAT AAA AGA GAG GCT GAA GCT CTA GAA TTC CCT GCC GGT CCG GAA ACT CTG TGC

gly ala glu leu val asp ala leu glu phe val cys gly asp arg gly phe tyr phe asn
GGT GCT GAA CTG GTT GAC GCT CTG GAG TTC GTA TGT GGT GAC CGT GGC TTT TAC TTC AAC

lys pro thr gly tyr gly ser ser ser arg arg ala pro gln thr gly ile val asp glu
AAA CCG ACT GGT TAC GGA TCC TCC TCT CGT CGC GCT CCG CAA ACT GGC ATC GTT GAT GAA

cys cys phe arg ser cys asp leu arg arg leu glu met tyr cys ala pro leu lys pro
TGC TGT TTT CGT TCT TGT GAC CTG CGC CGT CTG GAA ATG TAC TGC GCT CCG CTG AAA CCG

ala lys ser ala Term
GCT AAG TCT GCA TAG
```

Underscored - Mature Human IGF-1

Boxed - Collagenase Recognition Site

Yeast Invertase Signal - IGF-1 Protein

Fig. 12.

```
                1                                   10
                met leu leu gln ala phe leu phe leu leu ala gly phe ala ala lys ile
                ATG CTT TTG CAA GCT TTC CTT TTC CTT TTG GCT GGT TTT GCA GCC AAA ATA

            20                                      30
ser ala gly pro glu thr leu cys gly ala glu leu val asp ala leu gln phe val cys
TCT GCA GGT CCG GAA ACT CTG TGC GGC GCT GAG CTG GTT GAC GCT CTG CAG TTC GTA TGT

            40                                      50
gly asp arg gly phe tyr phe asn lys pro thr gly tyr gly ser ser ser arg arg ala
GGT GAT CGA GGC TTC TAC TTC AAC AAA CCG ACT GGG TAC GGA TCC TCC TCT CGT CGT GCT

            60                                      70
pro gln thr gly ile val asp glu cys cys phe arg ser cys asp leu arg arg leu glu
CCG CAA ACC GGC ATC GTT GAT GAA TGC TGT TTT CGG TCC TGT GAC CTT CGC CGT CTG GAA

            80                                  89
met tyr cys ala pro leu lys pro ala lys ser ala AM
ATG TAC TGC GCT CCG CTG AAA CCG GCT AAG TCT GCA TAG
```

Underscored - Mature Human IGF-1

HUMAN EGF

```
 ecoRI                                                  rsaI
 GAATTCATGA ACTCTGACTC TGAATGTCCA TTATCGCATG ATGGGT
 CTTAAGTACT TGAGACTGAG ACTTACAGGT AATAGCGTAC TACCCA

rsaI                hinfI     hinfI                    xbaI
 ACTG TTTGCACGAC GG            AGTCTGTA TGTATATTGA AGCT
 TGAC AAACGTGCTG CCTCA            GACAT ACATATAACT TCGAGATC

                                                                          sau3AI
xbaI                                                                     bglII
 CTAGAC AAGTACGCTT GTAACTGTGT TGTTGGTTAC ATCGGTGAAA GATGTCAATA CAGA
     TG TTCATGCGAA CATTGACACA ACAACCAATG TAGCCACTTT CTACAGTTAT GTCTCTAG

 sau3AI
bglII                                                  claI     hindIII
 GATCTA AAGTGGTGGG AATTGAGATA GATTGAATTG AATTGAAATC GATTAAAGCT T
     AT TTCACCACCC TTAACTCTAT CTAACTTAAC TTAACTTTAG CTAATTTCGA A
```

Fig. 15.

Yeast prepro α factor - EGF

Fig.16.

```
met arg phe pro ser ile phe ser ala val leu phe ala ala ser ser ala leu ala ala
ATG AGA TTT CCT TCA ATT TTT AGT GCA GTT TTA TTC GCA GCA TCC TCC GCA TTA GCT GCT

pro val asn thr thr thr glu asp glu thr ala gln ile pro ala glu ala val ile gly
CCA GTC AAC ACT ACA ACA GAA GAT GAA ACG GCA CAA ATT CCG GCT GAA GCT GTC ATC GGT

tyr ser asp leu glu gly asp phe asp val ala val leu pro phe ser asn ser thr asn
TAC TCA GAT TTA GAA GGG GAT TTC GAT GTT GCT GTT TTG CCA TTT TCC AAC AGC ACA AAT

asn gly leu leu phe ile asn thr thr ile ala ser ile ala ala lys glu glu gly val
AAC GGG TTA TTG TTT ATA AAT ACT ACT ATT GCC AGC ATT GCT GCT AAA GAA GAA GGG GTA

ser leu asp lys arg asn ser asp ser glu cys pro leu ser his asp gly tyr cys leu
TCT TTG GAT AAA AGA AAC TCT GAC TCT GAA TGT CCA TTA TCG CAT GAT GGG TAC TGT TTG

his asp gly val cys met tyr ile glu ala leu asp lys tyr ala cys asn cys val val
CAC GAC GGA GTC TGT ATG TAT ATT GAA GCT CTA GAC AAG TAC GCT TGT AAC TGT GTT GTT

gly tyr ile gly glu arg cys gln tyr arg asp leu lys trp trp glu leu arg AM
GGT TAC ATC GGT GAA AGA TGT CAA TAC AGA GAT CTA AAG TGG TGG GAA TTG AGA TAG
```

Yeast Preinvertase - EGF

Fig. 17.

```
            -19                                     -10
            met leu leu gln ala phe leu phe leu leu ala gly phe ala ala lys ile
GAATTCATG   ATG TTG TTG CAA GCT TTC TTG TTC TTG TTG GCT GGT TTC GCT GCT AAG ATC

          1                                     10
ser ala asn ser asp ser glu cys pro leu ser his asp gly tyr cys leu his asp gly
TCT GCT AAC TCT GAC TCT GAA TGT CCA TTA TCG CAT GAT GGG TAC TGT TTG CAC GAC GGA

     20                                     30
val cys met tyr ile glu ala leu asp lys tyr ala cys asn cys val val gly tyr ile
GTC TGT ATG TAC ATT GAA GCT CTA GAC AAG TAC GCT TGT AAC TGT GTT GTT GGT TAC ATC

     40                                     50          53
gly glu arg cys gln tyr arg asp leu lys trp trp glu leu arg AM
GGT GAA AGA TGT CAA TAC AGA GAT CTA AAG TGG TGG GAA TTG AGA TAG ATTGAATTGAATTGA

AATCGATTAAAGCTT
```

Human IGF-II coding sequence

Fig. 18.

```
                1                                       10
               met ala tyr arg pro ser glu thr leu cys gly gly glu leu val asp thr
TCTAGAATT      ATG GCT TAT CGA CCA TCT GAA ACC TTG TGT GGT GGT GAG CTG GTG GAC ACC

            20                                          30
leu gln phe val cys gly asp arg gly phe tyr phe ser arg pro ala ser arg val ser
CTC CAG TTC GTC TGT GGG GAC CGC GGT TTC TAC TTC TCT AGG CCC GCA AGC CGT GTG AGC

            40                                          50
arg arg ser arg gly ile val glu glu cys cys phe arg ser cys asp leu ala leu leu
CGT CGC AGT CGT GGC ATC GTT GAG GAG TGC TGT TTC CGC AGC TGT GAC CTG GCC CTA TTG

            60                                  68
glu thr tyr cys ala thr pro ala lys ser glu AM
GAA ACC TAC TGT GCT ACC CCA GCT AAG TCT GAA TAG GATCC
```

| | | | | | |
|---|---|---|---|---|---|
| Carboxy terminus of α-factor: | Gly -- | Gln -- | Pro -- | Met -- | Tyr COOH |
| Possible codons and their usage | GGU (90)<br>GGC (3)<br>GGA (0)<br>GGG (0) | CAA (20)<br>CAG (0) | CCA (32)<br>CCU (3)<br>CCC (1)<br>CCG (0) | AUG (20) | UAC (33)<br>UAU (0) |

Consensus oligonucleotides: 5'-GG$^{T}_{C}$CAACC$^{A}_{T}$ATGTAC

Synthesized oligonucleotide pools complementary to above:

I. 5'-GTACATTGGTTG$^{A}_{G}$CC

II. 5'-GTACATAGGTTG$^{A}_{G}$CC

Fig.19.

```
CGACAGTAAATTTTGCCGAATTTAATAGCTTCTACTGAAAAACAGTGGACCATGTGAAAAGATGCATCTCATTTATCAA
          -280                -260                -240                -220

ACACATAATATTCAAGTGAGCCTTACTTCAATTGTATTGAAGTGCAAGAAAACCAAAAAGCAACAACAGGTTTTGGATA
          -200                -180                -160                -140

AGTACATATATAAGAGGGCCTTTTGTTCCCATCAAAAATGTTACTGTTCTTACGATTCATTTACGATTCAAGAATAGTT
          -120                -100                -80                 -60

                                                        1
                                                   Met Arg Phe Pro Ser Ile
CAAACAAGAAGATTACAAACTATCAATTTCATACACAATATAAACGATTAAAAGA ATG AGA TTT CCT TCA ATT
          -40                 -20                       1

                                                  20
Phe Thr Ala Val Leu Phe Ala Ala Ser Ser Ala Leu Ala Ala Pro Val Asn Thr Thr Thr
TTT ACT GCA GTT TTA TTC GCA GCA TCC TCC GCA TTA GCT GCT CCA GTC AAC ACT ACA ACA
 20                         40                          60

                                                  40
Glu Asp Glu Thr Ala Gln Ile Pro Ala Glu Ala Val Ile Gly Tyr Leu Asp Leu Glu Gly
GAA GAT GAA ACG GCA CAA ATT CCG GCT GAA GCT GTC ATC GGT TAC TTA GAT TTA GAA GGG
 80                         100                         120

                                                  60
Asp Phe Asp Val Ala Val Leu Pro Phe Ser Asn Ser Thr Asn Asn Gly Leu Leu Phe Ile
GAT TTC GAT GTT GCT GTT TTG CCA TTT TCC AAC AGC ACA AAT AAC GGG TTA TTG TTT ATA
 140                        160                         180

                                                  80
Asn Thr Thr Ile Ala Ser Ile Ala Ala Lys Glu Glu Gly Val Ser Leu Asp Lys Arg Glu
AAT ACT ACT ATT GCC AGC ATT GCT GCT AAA GAA GAA GGG GTA TCT TTG GAT AAA AGA GAG
 200                        220                         240
```

*Fig. 21A.*

```
                                                    100
Ala Glu Ala Trp His Trp Leu Gln Leu Lys Pro Gly Gln Pro Met Tyr Lys Arg Glu Ala
GCT GAA GCT TGG CAT TGG TTG CAA CTA AAA CCT GGC CAA CCA ATG TAC AAG AGA GAA GCC
                     *     * *     *   *
 260                     280                     300

                                                    120
Glu Ala Glu Ala Trp His Trp Leu Gln Leu Lys Pro Gly Gln Pro Met Tyr Lys Arg Glu
GAA GCT GAA GCT TGG CAT TGG CTG CAA CTA AAG CCT GGC CAA CCA ATG TAC AAA AGA GAA
                     *     * *     *   *
 320                     340                     360

                                                    140
Ala Asp Ala Glu Ala Trp His Trp Leu Gln Leu Lys Pro Gly Gln Pro Met Tyr Lys Arg
GCC GAC GCT GAA GCT TGG CAT TGG CTG CAA CTA AAG CCT GGC CAA CCA ATG TAC AAA AGA
                         *     * *     *   *
 380                     400                     420

                                                    160                 165
Glu Ala Asp Ala Glu Ala Trp His Trp Leu Gln Leu Lys Pro Gly Gln Pro Met Tyr End
GAA GCC GAC GCT GAA GCT TGG CAT TGG TTG CAG TTA AAA CCC GGC CAA CCA ATG TAC TAA
                             *     * *     *   *
 440                     460                     480

GCCCGACTGATAACAACAGTGTAGATGTAACAAAGTCGACTTTGTTCCCACTGTACTTTTAGCTCGTACAAAATACAAT
500                 520                 540                 560
ATACTTTTCATTTCTCCGTAAACAACATGTTTTCCCATGTAATATCCTTTTCTATTTTTCGTTCCGTTACCAACTTTAC
580                 600                 620                 640
ACATACTTTATATAGCTATTCACTTCTATACACTAAAAAACTAAGACAATTTTAATTTTGCTGCCTGCCATATTTCAAT
660                 680                 700                 720
TTGTTATAAATTCCTATAATTTATCCTATTAGTAGCTAAAAAAAGATGAATGTGAATCGAATCCTAAGAGAATTC
740                 760                 780                 800
```

Fig. 21B.

```
TTCTTCATTGGTACATCAATGCCAGCAACGATGTGCGCATCTGGGCGACGCCTGTAGTGATTGTTTTCAAGGTATCGAG
              -300                -280                -260                -240

CCAAACTATTCATCGTTACTGTTTCAAATATTCAGTTGTTTCAGTACAGAGTCGCCGTGGACCTAGTGAAACTTGGTGT
              -220                -200                -180                -160

CTTTACAGCGCAGAGACGAGGGCTTATATGTATAAAAGCTGTCCTTGATTCTGGTGTAGTTTGAGGTGTCCTTCCTATA
              -140                -120                -100                -80

TCTGTTTTTATATTCTATATAATGGATAATTACTACCATCACCTGCATCAAATTCCAGTAAATTCACATATTGGAGAAA
              -60                 -40                 -20

 1                                  10                                  20
Met Lys Phe Ile Ser Thr Phe Leu Thr Phe Ile Leu Ala Ala Val Ser Val Thr Ala Ser
ATG AAA TTC ATT TCT ACC TTT CTC ACT TTT ATT TTA GCG GCC GTT TCT GTC ACT GCT AGT
1                       20                      40                      60

                                    30                                  40
Ser Asp Glu Asp Ile Ala Gln Val Pro Ala Glu Ala Ile Ile Gly Tyr Leu Asp Phe Gly
TCC GAT GAA GAT ATC GCT CAG GTG CCA GCC GAG GCC ATT ATT GGA TAC TTG GAT TTC GGA
                        80                      100                     120

                                    50                                  60
Gly Asp His Asp Ile Ala Phe Leu Pro Phe Ser Asn Ala Thr Ala Ser Gly Leu Leu Phe
GGT GAT CAT GAC ATA GCT TTT TTA CCA TTC AGT AAC GCT ACC GCC AGT GGG CTA TTG TTT
                        140                     160                     180

                                    70                                  80
Ile Asn Thr Thr Ile Ala Glu Ala Ala Glu Lys Glu Gln Asn Thr Thr Leu Ala Lys Arg
ATC AAC ACC ACT ATT GCT GAG GCG GCT GAA AAA GAG CAA AAC ACC ACT TTG GCG AAA AGA
                        200                     220                     240

                                    90                                  100
Glu Ala Val Ala Asp Ala Trp His Trp Leu Asn Leu Arg Pro Gly Gln Pro Met Tyr Lys
GAG GCT GTT GCC GAC GCT TGG CAC TGG TTA AAT TTG AGA CCA GGC CAA CCA ATG TAC AAG
                                        *     * *
                        260                     280                     300

                                    110                                 120
Arg Glu Ala Asn Ala Asp Ala Trp His Trp Leu Gln Leu Lys Pro Gly Gln Pro Met Tyr
AGA GAG GCC AAC GCT GAT GCT TGG CAC TGG TTG CAA CTC AAG CCA GGC CAA CCA ATG TAC
                                            *     * *
                        320                     340                     360

End
TGA AAAATGACCCTAAACTACTTCTAAACCCTCTCGATTTCTTTCACGTTCATACAACACCTAGTTTTATTTATTTTC
              380                 400                 420

TTTTCAATCTGAGTAGTTGAGTTTTCGATCACTCACATAGAACTATTTTTTGCCATTTAAATAAAGTATTCTCTCAAAT
440                 460                 480                 500

GATGCGATACTATAATACTCTTTGCCATATATTACATTCATTCATAAATAGGCTATGTTTCTATATCCGTTTCCGATTC
 520                 540                 560                 580

TGTCTGCAAGCAAGGTTCCCTATCATTACCGGATTGTTCACTATGGTTGGAGCTC
  600                 620                 640
```

Fig. 22.

p53
pBR322
α-factor
EcoRI
PstI
PstI
HindIII
EcoRI
BamHI
HindIII
T4 DNA Ligase
p57
pBR322
α-factor
EcoRI
PstI
PstI
HindIII
BamHI
HindIII
Klenow DNA Pol I
EcoRI
Isolate 1230bp fragment
EcoRI
PstI
PstI
GAAGCT
CTTCGA
CTAGAATTCATG
GATCTTAAGTAC
EcoRI
PstI
XbaI
Klenow DNA Pol I
PstI
Isolate 800bp fragment
pLeIFDtrpII
pBR322
LeIFD
E coli TRP promoter
EcoRI
XbaI
EcoRI
BamHI
EcoRI
PstI pBR322
EcoRI
BamHI
PstI
EcoRI, PstI
Isolate vector fragment
T4 DNA Ligase
p58
EcoRI
XbaI
PstI
PstI
EcoRI
BamHI
pBR322

PREPARATION OF HUMAN IGF VIA RECOMBINANT DNA TECHNOLOGY

Matter enclosed in heavy brackets [ ] appears in the original patent but forms no part of this reissue specification; matter printed in italics indicates the additions made by reissue.

CROSS REFERENCE TO RELATED APPLICATIONS

This application is related to commonly assigned applications filed concurrently herewith under U.S. Ser. Nos. 506,077 abandoned and 506,098 abandoned, and their parents U.S. Ser. Nos. 501,351 abandoned and 501,362 abandoned.

This is a continuation of application Ser. No. 06/506,078 filed on Jun. 20, 1983, abandoned, which is a continuation-in-part of Ser. No. 06/501,353 filed Jun. 6, 1983, now abandoned, which applications are incorporated herein by reference and to which applications priority is claimed under 35 USC §120.

FIELD OF THE INVENTION

This invention relates to the preparation of human IGF (insulin-like growth factor), in various forms, via recombinant DNA technology. Notably, the present invention provides for the preparation of human IGF as a mature protein product of expression, processing, and secretion in a recombinant DNA modified host organism. This invention thus provides for the production, isolation, and use of human IGF, in its various forms, as well as to the associated recombinant DNA technology by which it is prepared. In addition, the present invention relates to the similar preparation of a related protein, human EGF (Epidermal Growth Factor).

The present invention arises in part from the discovery of a novel system by which human IGF can be prepared by a recombinant host organism in the form of a discrete, mature protein. This is accomplished according to one aspect of the present invention by an expression system which permits the expression of the amino acid sequence of human IGF fused with at least a portion of the yeast alpha factor signal sequence, followed by processing of said signal sequence, and secretion of mature human IGF protein into the medium supporting the host organism. Thus, this novel aspect of the present invention, it is believed for the first time, permits the preparation, isolation, and utilization of human IGF as a discrete, mature protein. The present invention, in its broad compass, however, converts the preparation of the amino acid sequence of human IGF in other recombinant systems including bacteria and cell culture and includes, therefore, the expression of human IGF DNA sequences providing not only mature human IGF but also fusion product derivatives containing the amino acid sequence of IGF as the essential component. All such products have been found to be biologically active, hence useful as intended.

The publications and other materials hereof used to illuminate the background of the invention, and in particular cases, to provide additional details concerning its practice are incorporated herein by this reference and for convenience, are alphabetically and numerically referenced in the following text and respectively grouped in the appended bibliography.

BACKGROUND OF THE INVENTION

A. Human IGF (Insulin-like Growth Factor)

Human IGF has been the subject of a fair amount of intensive study by past workers. A body of literature has been developed related to various aspects of this protein or series of proteins (see references A through L).

Insulin-like growth factors I and II have been isolated from human serum (A). The designation "insulin-like growth factor" or IGF was chosen to express the insulin-like effects and the insulin-like structure of these polypeptides which act as mitogens on a member of cells. The complete amino acid sequences of IGF-I and IGF-II have been determined (D,E). They are both single-chain polypeptides with three disulphide bridges and a sequence identity of 49 and 47 percent respectively, to human insulin A and B chains. The connecting peptide or C region is considerably shorter than the one of proinsulin and does not show any significant homology to it. (For a summary of earlier studies on the biological efforts of IGF, see Reference F).

IGF-I and IGF-II are growth promoting polypeptides occurring in human serum and human cerebral spinal fluid. Their structure is homologous to proinsulin. IGF-I seems to be produced by the liver along with a specific IGF-binding protein both of which are under control of growth hormone. Thus, human IGF is considered to be an active growth promoting molecule that mediates the effect of human growth hormone.

It was perceived that the application of recombinant DNA and associated technologies would be a most effective way of providing the requisite large quantities of high quality human IGF for applied use to human beings as a growth factor. The goal was to produce human IGF either as biologically active fusion protein, or more importantly, as a mature protein, as products of recombinant DNA technology from a host organism. Such materials would exhibit bioactivity admitting of their use clinically in the treatment of various growth affected conditions.

B. Recombinant DNA Technology

Recombinant DNA technology has reached the age of some sophistication. Molecular biologists are able to recombine various DNA sequences with some facility, creating new DNA entities capable of producing copious amounts of exogenous protein product in transformed microbes and cell cultures. The general means and methods are in hand for the in vitro ligation of various blunt ended or "sticky" ended fragments of DNA, producing potent expression vehicles useful in transforming particular organisms, thus directing their efficient synthesis of desired exogenous product. However, on an individual product basis, the pathway remains somewhat tortuous and the science has not advanced to a stage where regular predictions of success can be made. Indeed, those who potend successful results without the underlying experimental basis, do so with considerable risk of inoperability.

DNA recombination of the essential elements, i.e., an origin of replication, one or more phenotypic selection characteristics, an expression promoter, heterologous gene insert and remainder vector, generally is performed outside the host cell. The resulting recombinant replicable expression vehicle, or plasmid, is introduced into cells by transformation and large quantities of the recombinant vehicle are obtained by growing the transformant. Where the gene is properly inserted with reference to portion which govern the transcription and translation of the encoded DNA message, the resulting expression vehicle is useful to actually produce the polypeptide sequence for which the inserted gene codes, a process referred to as expression. The resulting product may be obtained by lysing, if necessary, the host cell, in microbial systems, and recovering the product by appropriate purification from other proteins.

In practice, the use of recombinant DNA technology can express entirely heterologous polypeptides-so-called direct expression-or alternatively may express a heterologous polypeptide fused to a portion of the amino acid sequence of a homologous polypeptide. In the latter cases, the intended bioactive product is sometimes rendered bioinactive within the fused, homologous/heterologous polypeptide until it is cleaved in an extracellular environment. See reference (M) and (N).

Similarly, the art of cell or tissue cultures for studying genetics and cell physiology is well established. Means and methods are in hand for maintaining permanent cell lines, prepared by successive serial transfers from isolated normal cells. For use in research, such cell lines are maintained on a solid support in liquid medium, or by growth in suspension containing support nutriments. Scale-up for large preparations seems to pose only mechanical problems. For further background, attention is directed to references (O) and (P).

Likewise, protein biochemistry is a useful, indeed necessary, adjunct in biotechnology. Cells producing the desired protein also produce hundreds of other proteins, endogenous products of the cell's metabolism. These contaminating proteins, as well as other compounds, if not removed from the desired protein, could prove toxic if administered to an animal or human in the course of therapeutic treatment with desired protein. Hence, the techniques of protein biochemistry come to beat, allowing the design of separation procedures suitable for the particular system under consideration and providing a homogeneous product safe for intended use. Protein biochemistry also proves the identity of the desired product, characterizing it and ensuring that the cells have produced it faithfully with no alterations or mutations. This branch of science is also involved in the design of bioassays, stability studies and other procedures necessary to apply before successful clinical studies and marketing can take place.

SUMMARY OF THE INVENTION

The present invention is based upon the discovery that recombinant DNA technology can be used successfully to produce human IGF and related protein, human EGF, preferably in direct form and in amounts sufficient to initiate and conduct animal and clinical testing as prerequisites to market approval. The products human IGF and EGF are suitable for use in all of their forms as produced according to the present invention, viz. in tie prophylactic or therapeutic treatment of human beings for various growth associated conditions of diseases. Accordingly, the present invention, in one important aspect, is directed to methods of treating growth conditions in human subjects using human IGF or human EGF, and suitable pharmaceutical compositions thereof, prepared in accordance with the methods and means of the present invention.

The present invention further comprises essentially pure, mature human IGF, as a product of expression processing, and secretion in a recombinant host organism. Such human IGF is free from association with N-terminus amino acid sequence derivable from the expression systems that can be employed to prepare the material. Thus, while the present invention is directed to the preparation of polypeptides comprising the amino acid sequence of IGF, a notable aspect of the present invention involves the production of the mature human IGF directly into the medium of the recombinant host organism employed. The present invention is also directed to replicable DNA expression vehicle harboring gene sequences encoding human IGF and human EGF in expressible form, to microorganism strains or cell cultures transformed with such vehicles and to microbial or cell cultures of such transformants capable of producing amino acid sequences of human IGF and human EGF. In still further aspect, the present invention is directed to various processes useful for preparing said gene sequences, DNA expression vehicles, microorganisms and cell cultures and specific embodiments thereof. Still further, this invention is directed to the preparation of fermentation cultures of said microorganisms and cell cultures.

BRIEF DESCRIPTION OF THE DRAWINGS

FIG. 1 represents the chemically synthesized DNA strands used in the construction of expression vectors for human IGF (*DNA IGF-1 Left Half: 1L* (*43-mer*), *SEQ ID NO:14 ; DNA IGF-1 Left Half: 3L* (*43-mer*), *SEQ ID NO. 15; DNA IGF-1 Left Half: 2L* (*46-mer*), *SEQ ID NO. 16; DNA IGF-1 Left Half: 4L* (*46-mer*), *SEQ ID NO. 17, DNA IGF-1 Right Half: 1R* (*46-mer*), *SEQ ID NO. 18; DNA IGF-1 Right Half: 3R* (*46-mer*), *SEQ ID NO. 19; DNA IGF-1 Right Half: 2R* (*54-mer*), *SEQ ID NO. 20; DNA IGF-1 Right Half: 4R* (*46-mer*). *SEQ ID NO. 21*.

FIG. 2 shows the completed double stranded DNA of FIG. 1 (*Protein IGF-1 Left Half: Part 1, SEQ ID NO. 22; DNA IGF-1 Left Half: Part 1, SEQ ID NO. 23; Protein IGF-1 Left Half: Part 2, SEQ ID NO. 24; DNA IGF-1 Left Half: Part 2, SEQ ID NO. 25; Protein IGF-1 Right Half: Part 3, SEQ ID NO. 26; DNA IGF-1 Right Half: Part 3, SEQ ID NO. 27; Protein IGF-1 Right Half: Part 4, SEQ ID NO. 28; DNA IGF-1 Right Half: Part 4, SEQ ID NO. 29*).

FIG. 3 show the fragments of DNA of FIG. 2 after restriction by EcoRI and PstI and BamHI (*Protein IGF-1 Left Half: Part 1, SEQ ID NO. 30; DNA IGF-1 Left Half: part 1: 1L, SEQ ID NO. 31; DNA IGF-1 Left Half: Part 1: 3L, SEQ ID NO. 32; Protein IGF-1 Left Half: Part 2, SEQ ID NO. 33; DNA IGF-1 Left Half: Part 2: 2L, SEQ ID NO. 34; DNA IGF-1 Left Half: Part 2: 4L, SEQ ID NO. 35*).

FIG. 5 show parts 3 and 4 of IGF-I right half (*Protein IGF-1 Right Half: Part 3, SEQ ID NO. 36; DNA IGF-1 Right Half: Part 3, SEQ ID NO. 37; DNA IGF-1 Right Half: Part 3, SEQ ID NO. 38; Protein IGF-1 Right Half: Part 4, SEQ ID NO. 39; DNA IGF-1 Right Half: Part 4, SEQ ID NO. 40; DNA IGF-1 Right Half: Part 4, SEQ ID NO. 41*).

FIG. 7 shows a sequence of DNA (*SEQ ID NO. 43*) and deduced fusion protein containing IGF-I (*SEQ ID NO. 42*).

FIG. 8 shows a sequence of DNA (*SEQ ID NO. 45*) and deduced short fusion protein containing IGF-I (*sLE-IGF-1 Fusion Protein, SEQ ID NO. 44*).

FIG. 10 shows the DNA and protein sequence of IGF-I fused with alpha factor pre-pro sequence (*IGF-1 Protein fused with alpha factor pre-pro sequence, SEQ ID NO. 46; DNA, SEQ ID NO. 47*).

FIG. 12 shows the yeast invertase signal fused to IGF-I (*Yeast Invertase Signal-IGF-1 fusion protein, SEQ ID NO. 48; DNA, SEQ ID NO. 49*). *The amino acid sequence of mature human IGF-I is shown in the figure by the underscored amino acids* (*amino acids 20–89 of SEQ ID NO. 48*).

FIG. 15 is the synthetic DNA used to construct the coding sequence of mature human EGF (*SEQ ID NO. 50*).

FIG. 16 depicts the yeast alpha factor "pre-pro" sequence fused to the human EGF coding sequence (*Yeast alpha factor protein "pre-pro" sequence fused with EGF, SEQ ID NO. 51; EGF DNA fused with yeast alpha factor "pre-pro" sequence, SEQ ID NO. 52*).

FIG. 17 depicts the yeast invertase signal sequence fused to the human EGF coding sequence (*Yeast invertase signal protein sequence fused with EGF, SEQ ID NO. 53; EGF DNA fused with invertase sequence, SEQ ID NO. 54*).

FIG. 18 shows the coding sequence for human IGF-II (*Protein coding sequence for Human IGF-II, SEQ ID NO. 55; DNA coding sequence for Human IGF-II, SEQ ID NO. 56*).

FIG. 19 illustrates the structure of pools of synthetic oligonucleotides used as hybridization probes to isolate the gene for α-factor (*Protein carboxy terminus of alpha factor, SEQ ID NO. 57; DNA consensus oligonucleotides encoding alpha-factor carboxy terminus, SEQ ID NO. 58; DNA oligonucleotide pool I* (*complementary to SEQ ID 58*), *SEQ ID NO. 59; DNA oligonucleotide pool II* (*complementary to SEQ ID 58*), *SEQ ID NO. 60*).

FIG[S]. 21A (*DNA sequence of alpha factor, SEQ ID NO. 61; Protein sequence of alpha factor, SEQ ID NO. 62*) and *FIG.* 21B (*Protein sequence of alpha factor, SEQ ID NO. 63; DNA sequence of alpha factor, SEQ ID NO. 64*) and *FIG.* 22 (*DNA sequence of alpha factor, SEQ ID NO. 65; Protein sequence of alpha factor, SEQ ID NO. 66*) are the nucleotide sequences of α-factor genes.

Figure 23A:
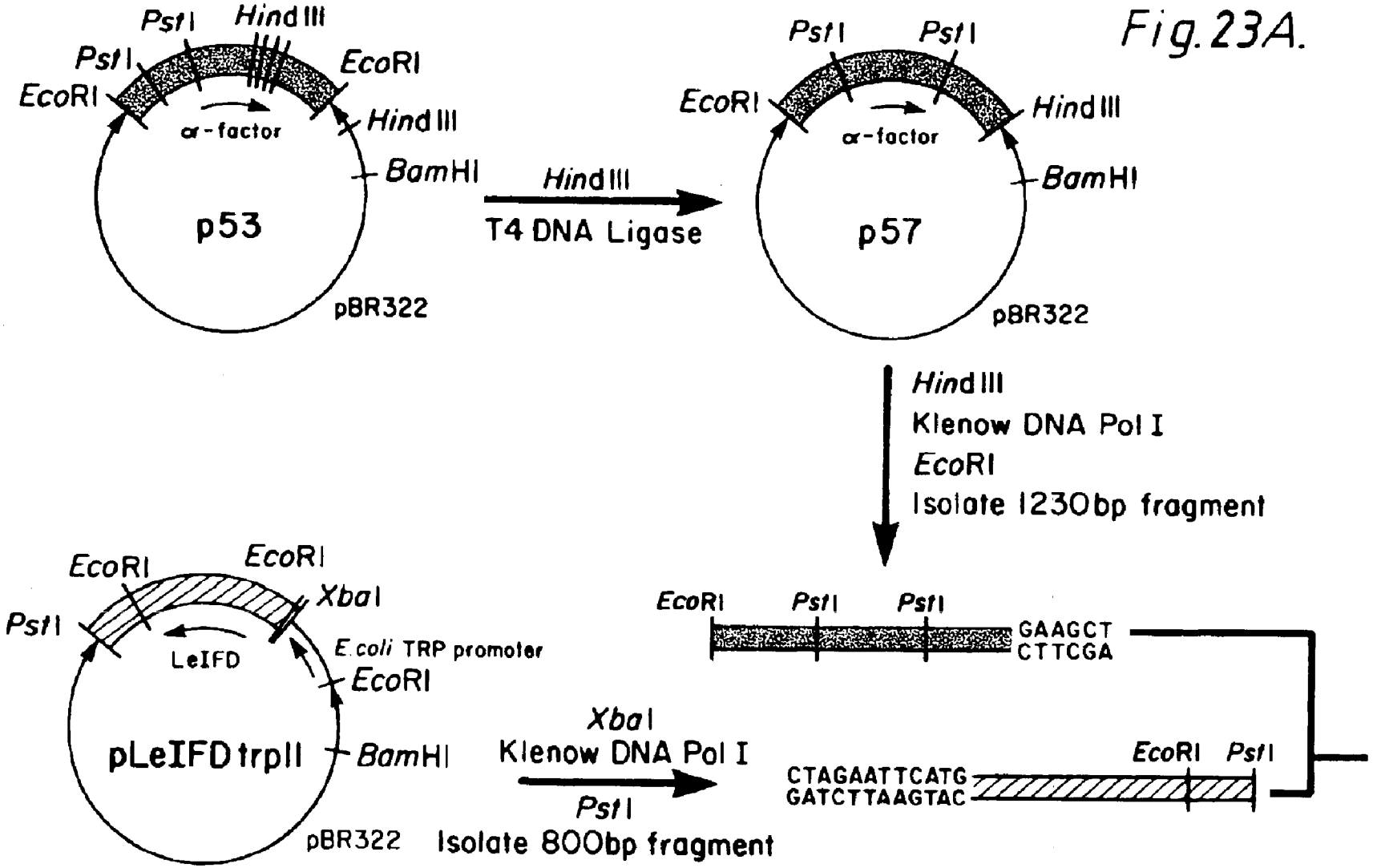
Figures 23, 23A, 23B:
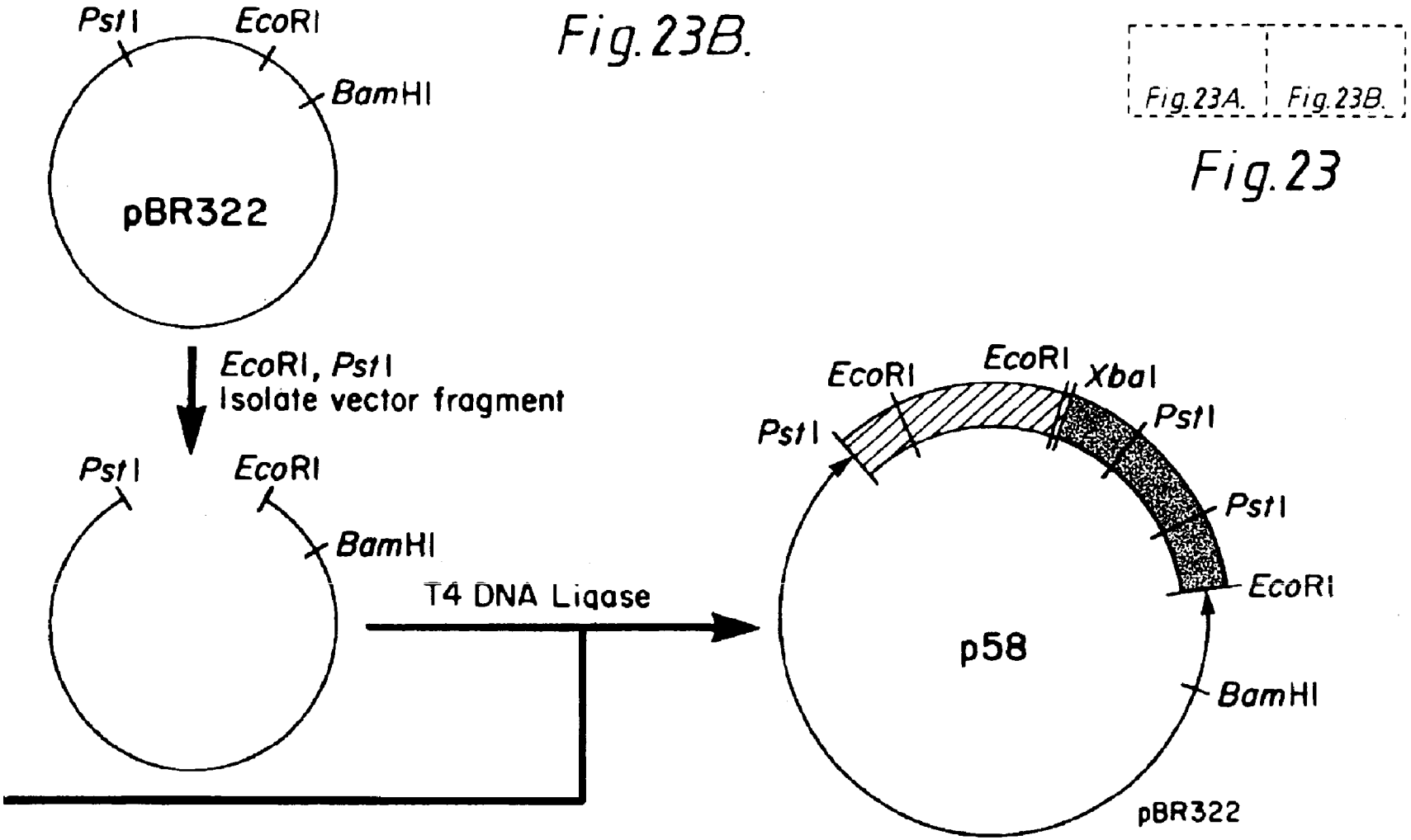

FIGS. 23A and 23B illustrates the scheme for joining the gene for human interferon D with the gene for the α-factor promoter and signal sequence.

Figure 24:
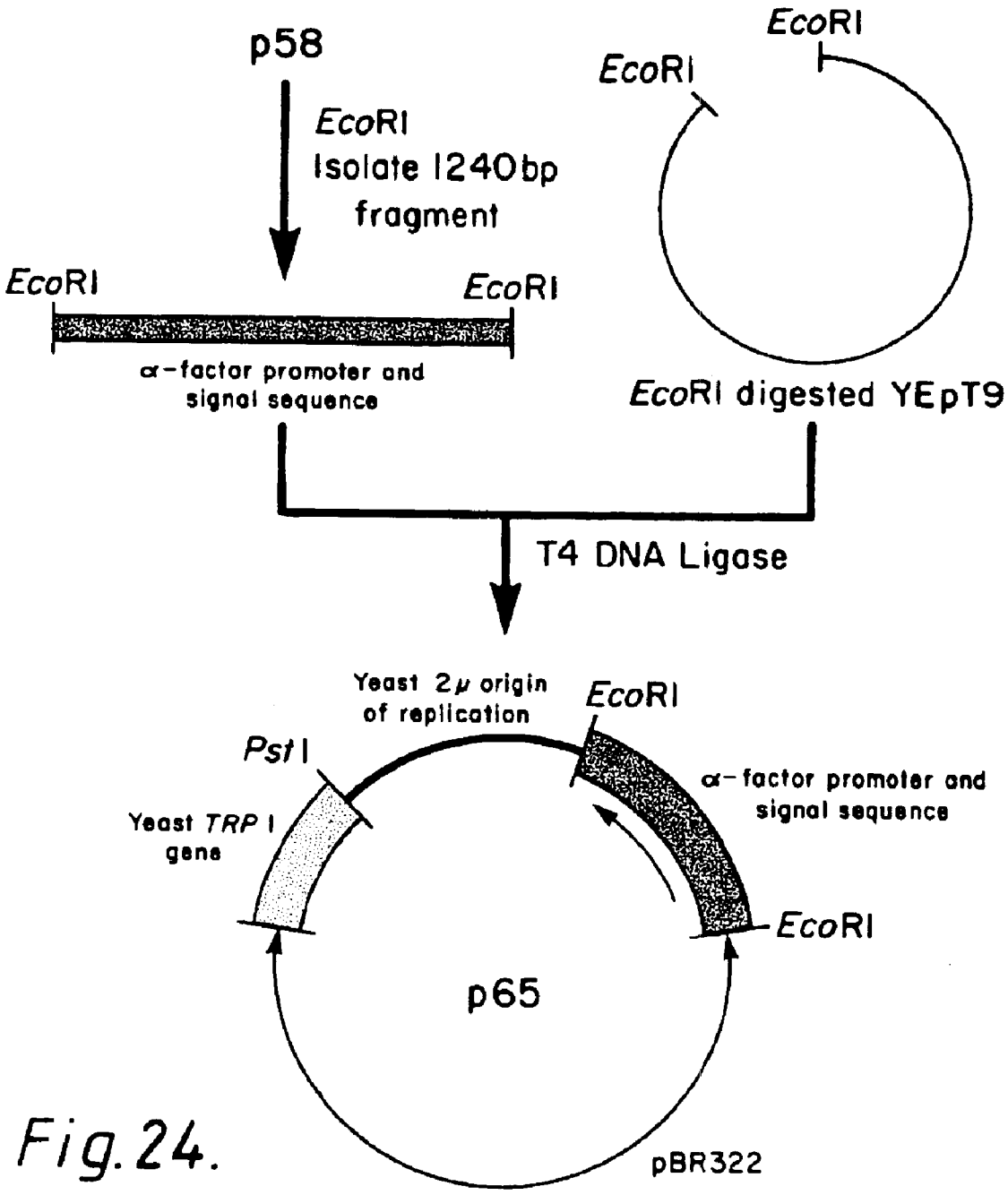

FIG. 24 illustrate the scheme for construction of a yeast/E. coli shuttle vector for use as a starting plasmid herein for expression of heterologous genes supplying the α-factor promoter and signal polypeptide gene sequences.

DETAILED DESCRIPTION

A. Definitions

As used herein, "human IGF" and "human EGF" denotes human insulin-like growth factor and human epidermal growth factor, produced by microbial or cell culture systems and bioactive forms comprising the amino acid sequence corresponding to human IGF and human EGF otherwise native to human tissue. The human IGF and EGF proteins produced herein have been defined by means of DNA, gene, and deductive amino acid sequencing. It will be understood that inasmuch as natural allelic variations exist and occur from individual to individual, as demonstrated by (an) amino acid difference(s) in the overall sequence or by deletions, substitutions, insertions, inversions, or additions of one or more amino acids of said sequences, the present invention is intended to embrace all of such allelic variations of the two molecules involved. In addition, the location of and the degree of glycosylation depend upon the nature of the recombinant host organism employed and such variations as may occur as included within the ambit of this invention. Finally, the potential exists in the use of DNA technology for the preparation of various derivatives of human IGF and human EGF by simple modification of the underlying gene sequence for such molecules. Such modifications could be accomplished by means of site directed mutagenesis of the underlying DNA, as an example. All such modifications resulting in derivatives of human IGF and human EGF are included within the scope of the present invention so long as the essential characteristic human IGF and human EGF activities remain unaffected in kind.

"Essentially pure form" when used to describe the state of human IGF or human EGF produced by this invention means that the proteins are free of proteins or other materials normally associated with human IGF or human EGF when produced by non-recombinant cells, i.e. in their "native" environments.

"Expression vector" includes vectors which are capable of expressing DNA sequences contained therein, where such sequences are operably linked to other sequences capable of effecting their expression, i.e., promotor/operator sequences. In sum, "expression vector" is given a functional definition: any DNA sequence which is capable of effecting expression of a specified DNA code disposed therein. In general, expression vectors of utility in recombinant DNA techniques are often in the form of "plasmids" which refer to circular double stranded DNA loops which in their vector form are not bound to the chromosome. In the present specification, "plasmid" and "vector" are used interchangeably as the plasmid is the most commonly used form of vector. However, the invention is intended to include such other forms of expression vectors which function equivalently and which become known in the art subsequently.

"Recombinant host cells" refers to cells which have been transformed with such vectors. Thus, the human IGF and human EGF molecules produced by such cells can be referred to as "recombinant human IGF" and "recombinant human EGF".

B. Host Cell Cultures and Vectors

The vectors and methods disclosed herein are suitable for use in host cells over a wide range of prokaryotic and eukaryotic organisms.

In general, or course, prokaryotes are preferred for cloning of DNA sequences in constructing the vectors useful in the invention. For example, E. coli K12 strain 294 (ATCC No. 31446) is particularly useful. Other microbial strains which may be used include E. coli strains such as E. coli B, and E. coli X1776 (ATTC No. 31537). The aforementioned strains, as well as E. coli W3110 ($F^-$, $\lambda^-$, prototrophic, ATTC No. 27325), bacilli such as Bacillus subtilus, and other enterobacteriaceae such as Salmonella typhimurium or Serratia marcesans, and various pseudomonas species may be used. These examples are, of course, intended to be illustrative rather than limiting.

In general, plasmid vectors containing replicon and control sequences which are derived from species compatible with the host cell are used in connection with these hosts. The vector ordinarily carries a replication site, as well as marking sequences which are capable of providing phenotypic selection is transformed cells. For example, E. coli is typically transformed using pBR 322, a plasmid derived from an E. coli species (Bolivar, et al., Gene 2: 95 (1977)) .pBR322 contains genes for ampicillin and tetracycline resistance and thus provides easy means for identifying transformed cells. The pBR322 plasmid, or other microbial plasmid must also contain, or be modified to contain, promoters which can be used by the microbial organism for expression of its own proteins. Those promoters most commonly used in recombinant DNA construction include the β-lactamase (penicillinase) and lactose promoter systems (Chang et al, Nature, 275: 615(1978), Itakura, et al, Science, 198: 1056 (1977); (Goeddel, et al Nature 281: 544 (1979) and a tryptophan (trp) promoter system (Goeddel, et al, Nucleic Acids Res., 8: 4057 (1980); EPO Appl Publ No. 0036776). While these are the most commonly used, other microbial promoters have been discovered and utilized, and details concerning their nucleotide sequences have been published, enabling a skilled worker to ligate them functionally with plasmid vectors (Siebenlist, et al, Cell 20: 269 (1980)).

In addition to prokaryotes, eukaryotic microbes, such as yeast cultures, may also be used. Saccharomyces cerevisiae, or common baker's yeast is the most commonly used among eukaryotic microorganisms, although a number of other strains are commonly available. For expression in Saccharomyces, the plasmid YRp7, for example, (Stinchcomb, et al, Nature, 282: 39 (1979); Kingsman et al, Gene 7: 141 (1979); Tschemper, et al, Gene 10: 157(1980)) is commonly used. This plasmid already contains the trp1 gene which provides a selection marker for a mutant strain of yeast lacking the ability to grow in tryptophan, for example ATCC No. 44076 or PEP4-1 (Jones, Genetics, 85: 12 (1977)). The presence of the trp1 lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman, et al., J. Biol. Chem., 255: 2073 (1980)) or other glycolytic enzymes (Hess, et al., J. Adv. Enzyme Reg., 7: 149 (1968); Hotland, et al, Biochemistry, 17: 4900 (1978)), such as enolase, glyceraldehyde-3-phosphatic dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination. Other promoters which have the additional advantage of transcription controlled by growth conditions are the promoter regions for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization (Holland, ibid). Any plasmid vector containing yeast-compatible promoter, origin of replication and termination sequences is suitable.

In addition to microorganisms, cultures of cells derived from multicellular organisms may also be used as hosts. In principle, any such cell culture is workable, whether from vertebrate or invertebrate culture. However, interest has been greatest in vertebrate cells, and propagation of vertebrate cells in culture (tissue culture) has become a routine procedure in recent years [Tissue Culture, Academic Press, Kruse and Patterson, editors (1973)]. Examples of such useful host cell lines are VERO and HeLa cells, Chinese hamster ovary (CHO) cell lines, and W138, BHK, COS-7 and MDCK cell lines. Expression vectors for such cells ordinarily include (if necessary) an origin of replication, a promoter located in front of the gene to be expressed, along with any necessary ribosome binding sites, RNA splice sites, polyadenylation site, and transcriptional terminator sequences.

For use in mammalian cells, the control functions on the expression vectors are often provided by viral material. For example, commonly used promoters are derived from polyoma. Adenovirus 2, and most frequently Simian Virus 40 (SV40). The early and late promoters of SV40 virus are particularly useful because both are obtained easily from the virus as a fragment which also contains the SV40 viral origin of replication (Fiers, et al, Nature, 273: 113 (1978) incorporated herein by reference. Smaller or larger SV40 fragments may also be used, provided there is included the approximately 250 bp sequence extending from the Hind III site toward the BglI site located in the viral origin of replication. Further, it is also possible, and often desirable, to utilize promoter or control sequences normally associated with the desired gene sequence, provide such control sequences are compatible with the host cell systems.

An origin of replication may be provided either by construction of the vector to include an exogenous origin, such as may be derived from SV40 or other viral (e.g. Polyoma, Adeno, VSV, BPV, etc.) source, or may be provided by the host cell chromosomal replication mechanism. If the vector is integrated into the host cell chromosome, the latter is often sufficient.

C. Methods Employed

If cells without formidable cell wall barriers are used as host cells, transfection is carried out by the calcium phosphate precipitation method as described by Graham and Van der Eb, Virology, 52: 546 (1978). However, other methods for introducing DNA into cells such as by nuclear injection or by protoplast may also be used.

If prokaryotic cells or cells which contain substantial cell wall constructions are used, the preferred method of transfection is calcium treatment using calcium chloride as described by Cohen, F. N. et al Proc. Natl. Acad. Sci. (USA), 69: 2110 (1972).

Construction of suitable vectors containing the desired coding and control sequences employ standard ligation techniques. Isolated plasmids or DNA fragments are cleaved, tailored, and religated in the form desired to form the plasmids required.

Cleavage is performed by treating with restriction enzyme (or enzymes) in suitable buffer. In general, about 1 μg plasmid or DNA fragments is used with about 1 unit of enzyme in about 20 μl of buffer solution. (Appropriate buffers and substrate amounts for particular restrictions enzymes are specified by the manufacturer.) Incubation times of about 1 hour at 37° C. are workable. After incubations, protein is removed by extraction with phenol and chloroform, and the nucleic acid is recovered from the aqueous fraction by precipitation with ethanol.

If blunt ends are required, the preparation is treated for 15 minutes at 15° with 10 units of Polymerase I (Klenow), phenol-chloroform extracted, and ethanol precipitated.

Size separation of the cleaved fragments is performed using 6 percent polyacrylamide gel described by Goeddel, D., et al, Nucleic Acids Res., 8: 4057 (1980) incorporated herein by reference.

For ligation approximately equimolar amounts of the desired components, suitably end tailored to provide correct matching are treated with about 10 units T4 DNA ligase per 0.5 μg DNA. (When cleaved vectors are used as components, it may be useful to prevent religation of the cleaved vector by pretreatment with bacterial alkaline phosphatase.)

For analysis to confirm correct sequences in plasmids constructed, the ligation mixtures are used to transform E. coli K12 strain 294 (ATCC 31446), and successful transformants selected by ampicillin resistance where appropriate. Plasmids from the transformants are prepared, analyzed by restriction and/or sequenced by the method of Messing, et al, Nucleic Acids Res., 9:309 (1981) or by the method of Maxam, et al, Methods in Enzymology, 65:499 (1980).

EXAMPLES

The following examples are intended to illustrate but not to limit the present invention.

Synthesis and Expression of Human IGF-1

Enzymes were obtained from the following suppliers:

New England Biolabs: restriction enzymes, T4 DNA ligase Bethesda Research Labs: restriction enzymes, Bact. Alkaline Phos.

Boehringer-Mannheim: E. coli DNA Polymerase I (Klenow) P+L Biochemicals: Polynucleotide kinase, Terminal Nucleotidyl Transferase New England Nuclear:

pBR322 [oligo(dG)-tailed] DNA

Reagents:

BioRad: Bis Acrylamide, Acrylamide, TEMED

Sigma: Ammonium Persulfate

Amersham: 10218$\gamma^{32}$P ATP-5000 Ci/mmol; 10165 $\alpha^{32}$P dCTP>400 Ci/mmol.

Solutions and Media: 1×TBE: 054M Tris Base, 0.54 M Boric

Acid, 0.017 M $Na_2$ EDTA.

Difco: Yeast Nitrogenous Base (YNB); Tryptone, Yeast

Extract, Bacto-Agar; Casamino Acids.

Autoradiography:

Kodak X-0 mat AR XAR-2 Film

Glass Beads:

0.45–0.60 mM B. Braun Melsungen AG

LB medium (per liter):

10 g NaCl; 5 g yeast extract; 10 g tryptone; 0.17 ml NaOH (50 percent)

LB Agar (per liter):

10 g tryptone; 5 g yeast extract; 0.5 g NaCl; 15 g Bacto-Agar adjusted to pH 7.5 with NaOH.

Antibiotics:

Tetracycline (5 μg/ml) in all mediums; Ampicillin (20 μg/ml) in all mediums (plates or liquid)

M9 Medium (per liter):

6 g $Na_2$ $HPO_4$ (anhydrous); 1 g $NH_4Cl$; 3 g $KH_2PO_4$; 0.5 g NaCl; 1 mM $MgSO_4$; 0.5 percent (w/v) glucose; 0.5 percent (w/v) Casamino Acids; 0.0001 percent Thiamine-HCl.

YNB-CAA (per liter):

6.7 g Yeast Nitrogenous Base (without Amino Acids); 10 mg adenine; 10 mg uracil; 5 g Casamino Acids; 20 g Glucose.

YNB-CAA agar plates (per liter):

Same as YNB-CAA +30 g agar.

Standard Ligation Conditions:

10-fold molar excess of insert (for linker) to vector. 1×T4 DNA ligase buffer and 400–800 U T4 DNA ligase; 14°–12–16 hours.

Standard Kination Conditions:

1× Polynucleotide kinase buffer, 15 U polynucleotide kinase;

37°60 minutes; followed by reaction termination by heating to 65° for 10 minutes.

1× Kinase Buffer:

70 mM Tris-HCl (pH 7.6); 10 mM $MgCl_2$; 5 mM DTT 1×T4 DNA Ligase Buffer:

50 mM Tris-HCl (pH 7.8); 10 mM $MgCl_2$; 20 mM DTT; 1 mM rATP.

Construction, Strategy and Selection of a DNA Sequence

The 1° protein structure of the human IGF-1 molecule has been determined (1). Based upon this protein sequence and the genetic code, a DNA sequence coding for mature human IGF-1 protein, including all possible base substitutions at any one base position, was determined by computer analysis (Genentech Untrans Program). Using a restriction site analysis program (Genentech Asearch Program), all potential restriction sites located in all possible DNA sequences consistently coding for the same protein were found. Three sites internal to the coding sequence were selected: PstI, BamHI, and AvaII. Two additional sites were placed at the ends, just outside of the coding sequence of the mature protein: one EcoRI site before the initiation codon, AUG, and the StiII site following the termination codon, TAG of the coding sequence. The choice of these sties facilitated the cloning of the coding sequence in separate parts, each of which subsequently could be excised and then assembled to form an intact synthetic IGF-1 gene. This construction involved in the assembly of 4 parts, 2 parts forming the left half, 2 parts forming the right half. Each part consisted of two single strands of chemically synthesized DNA (see FIG. 1; *SEQ ID NOS. 14–21*). Proposed synthetic fragments were also analysed for internal complementar[it]y.

The constructions used to generate these four parts employed the use of DNA Polymerase I repair synthesis of synthetic oligonucleotide substrates having 9–10 bp stretches of complementary sequence at their 3' termini. In the presence of DNA Polymerase I (Klenow) and the four deoxynucleotide triphosphates, these primer-templates were extended to become full-length double-stranded DNAs. To prevent priming at locations other than the desired portions as well as self-hybridizations, each set of single-stranded DNAs were analysed by a computer program (Genentech Homology Program), and wherever possible, sequences which would have potentially led to hairpin loops, self-priming, or mis-priming, were eliminated by alternate codon usage. Each of these four double-stranded DNAs were synthesized to include 9–12 additional bp of non-IGF-1 coding DNA at each end (see FIG. 2; *SEQ ID NOS. 22–29*). This additional DNA was included to allow generation of sticky ends by restriction enzyme digestion. The sticky ends thus formed facilitated the ligation of the double-stranded pieces to contiguous coding sections of the synthetic gene or into a cloning vehicle.

The 9–12 extra bp of double stranded DNA beyond the restriction site at the end of each part (see FIG. 2; *SEQ ID NOS. 22–29*) allowed for the TdT-mediated formation of single-stranded oligodeoxycytidine strands at the 3' ends of each double-stranded DNA section. These oligodeoxycytidine tailed double-stranded DNAs could then be annealed into a complementary oligodeoxyguanosine tailed PstI site of a cloning vehicle. Once cloned, and sequenced to ensure the correct base sequences, the parts could be easily isolated and ligated following restriction enzyme cleavage at the restriction sites selected at the ends of each of the four parts, to form the intact synthetic IGF-1 gene.

The method used successfully here was similar to that described by Rossi et al. (28); however, attempts at the construction and cloning of the IGF-1 coding sequence using the Rossi et al. method (28) with only two base pairs of extra DNA beyond the restriction enzyme recognition sites repeatedly failed. The method employed here also differs from the Rossi et al. procedure (28) in that restriction sites placed at both ends of a double stranded DNA allow for the convenience of cloning each double stranded DNA fragment, individually, by (dC)-tailing and annealing into a (dG)-tailed vector, a method which in practice requires less of the dobule stranded DNA than three-part ligations.

Chemical Synthesis

Eight fragments, 43, 43, 46, 46, 46, 46, 54, and 46 bases in length (see FIG. 1; *SEQ ID NOS. 14–21*), were chemically synthesized according to the method of Crea and Horn (2), the only change being the use of mesitylene nitrotriazole as the condensing agent rather than 2,4,6-Triisopropyl benzenesulfonylchloride tetrazole.

The syntheses of the fragments were accomplished from the appropriate solid support (cellulose) by sequential addition of the appropriate fully-protected dimer- or trimer-blocks. The cycles were carried out under the same conditions as described in the synthesis of oligothymidilic acid (see Crea et al., supra). The final polymers were treated with base (aqueous conc. $NH_3$) and acid (80 percent HoAc), the polymer pelleted off, and the supernatant was evaporated to dryness. The residue, dissolved in 4 percent aq. $NH_3$, was washed with ethyl ester (3×) and used for the isolation of the fully deprotected fragment.

Purification was accomplished by electrophoresis using 20 percent polyacrylamide gels. The pure oligonucleotide was ethanol precipitated following gel elution.

225–285 pmoles of each chemically synthesized fragment was mixed with an equivalent amount of the complementary single-stranded DNA fragment (i.e. 1L+3L; 2L+4L; 1R+3R; 2R+4R) in the presence of deoxyribonucleoside triphosphates at a final concentration of 200 μM with the exception of dCTP. dCTP was added to a concentration of 5 μM as a $\alpha^{32}$ P-labeled isotope (with a specific activity of 1000–2000 Ci/mmol) to allow easy monitoring to the repair-synthesis reaction product. The reactions were carried out in a buffer containing a final concentration of 50 mM Tris HCl pH 7.5; 20 mM $MgCl_2$; 20 mM DTT and 154 DNA Polymerase 1 (Klenow) in a reaction volume of 200 μl. Reactions were allowed to proceed at 4° for 12–18 hrs.

Upon completion, EDTA was added to a concentration of 25 mM. Sample buffer containing the mixes were phenol extracted, $CHCl_3$ extracted 2×, and products were etOH precipitated. Pellets were taken up in 0.3 M NaOAc and the DNA was reprecipitated with etOH. After dissolving the pellets in $H_2O$, the 1L+3L and 2L+4L products were then digested separately with PstI in 100 μl reaction mixes containing 1×PstI buffer (50 mM $(NH_4)_2$ $SO_4$, 20 mM Tris HCl pH 7.5, 10 mM $MgCl_2$), and 70 U PstI. After 4 hrs, EDTA was added to a concentration of 10 mM, and the material was ethanol precipitated. Pellets were then taken up in 0.3 M NaOAc and reprecipitated, then taken up in $H_2O$. The PstI-digested 1L+3L product was digested with EcoRI at 37° in a 100 μl reaction mix 1×EcoRI buffer (150 mM NaCl, 6 mM Tris HCl pH 7.5, 6 mM $MgCl_2$ ) and 70 U EcoRI. The PstI digested 2L+4L product was digest at 37° with BamHI in a 100 μl reaction mixed in 1×BamHI Buffer (150 mM NaCl, 6 mM Tris HCl pH 7.9, 6 mM $MgCl_2$) and 70 U BamHI. After 4 hrs, EDTA was added to both mixtures, and sample buffer was added. They were electrophoresed on a 6 percent polyacrylamide stab gel. Six percent slab gels were cast with a mixture containing 6 percent (w/v) acrylamide (20 to 1 ratio of acrylamide to Bis acrylamide) 1×TBE, 1 percent APS and 0.1 percent TEMED. Reaction products were located on the gel by autoradiography and the band corresponding to the 45 bp EcoRI-PstI digested 1L+3L product (Part 1) (see FIG. 3; *SEQ ID NOS. 30–32*) and the band corresponding to the 50 bp PstI-BamHI digested 2L+4L product (Part 2) (see FIG. 3; *SEQ ID NOS. 33–35*) were excised from the gel, and the material was electroeluted in 0.2×TBE, phenol extracted, $CHCl_3$ extracted, and ethanol precipitated. Parts 1 and 2 were dissolved in $H_2O$.

Cloning Vector Prep

Cloning vector was prepared by digesting 20 μg pBR322 (15) with 50 U EcoRI and 60 U BamHI, in 1×RI Buffer at 37° for 6 hr. After addition of EDTA to a concentration of 10 mM, sample buffer was added, and the mixture was run on a 5 percent polyacrylamide gel. The gel was developed by staining 10' in $H_2O$ containing 5 μg/ml Et. Bromide, rinsing 2× in $H_2O$ and placing upon a UV transilluminator (302 mM). The band corresponding to ca. 3712 bp EcoRI-BamHI digested pBR322 molecules was cut from the gel. The DNA was electroeluted from the gel slice, phenol extracted, $CHCl_3$ extracted 2×, and ethanol precipitated. The pellet was dissolved in $H_2O$ and was ready for ligation.

Ligation

Figure 4:
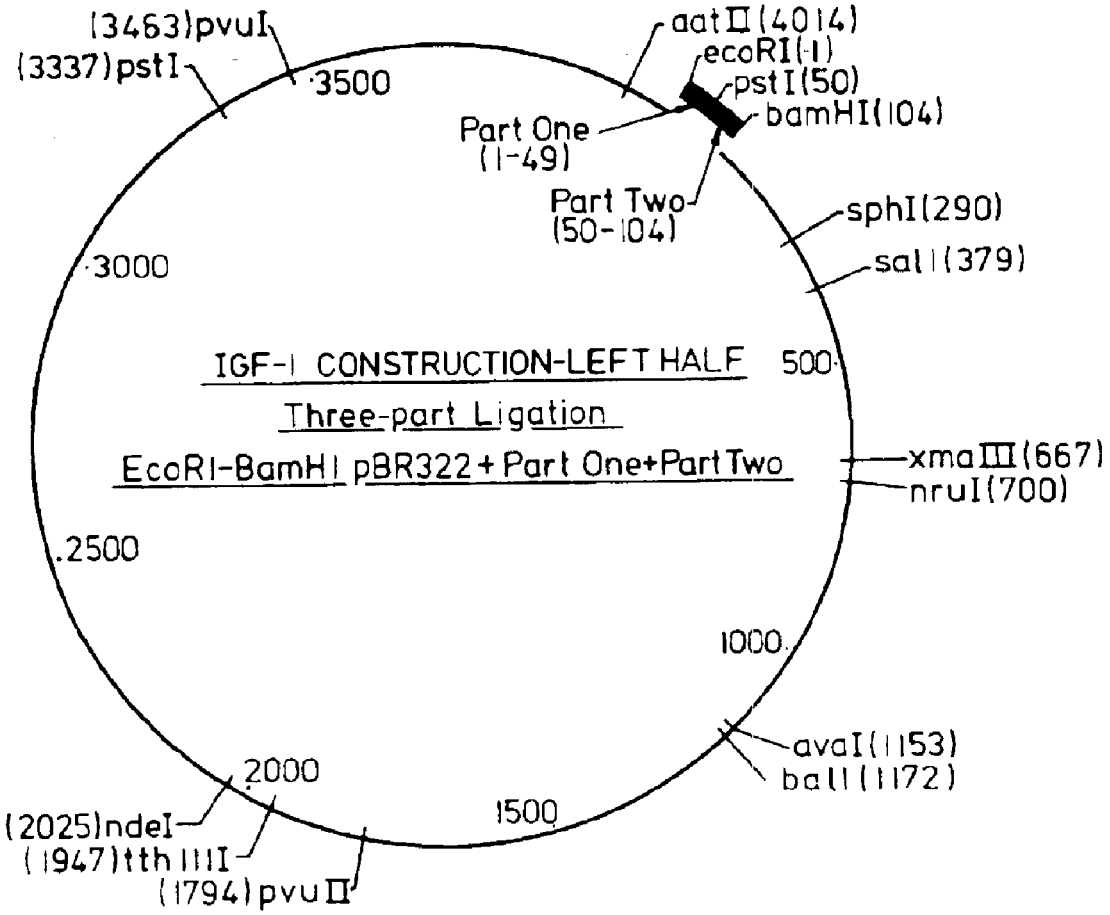
FIG. 4 depicts the ligation of parts 1 and 2 of FIG. 3 into PBR322.

In a three-part ligation (see FIG. 4), in which the molar ratio of inserts to vector in the ligation reaction was approximately 10 to 1, parts 1 and 2 were ligated into the EcoRI-BamHI digested 322 vector in 1×T4 DNA ligase buffer (cont. 50 mM Tris HCl pH 7.8; 10 mM $MgCl_2$, 20 mM DTT, 1 mM rATP) and ~800 U T4 DNA ligase (NEB). The reaction was carried out at 14° for 12–16 hrs.

Transformations

E. coli strain 294 was used as the transformation host, using the procedure of M. Dagert and S. D. Ehrlich (3). The transformed cells [W]*w*ere plated on LB-agar plates containing ampicillin (20 μg/ml; LB-Amp-plates) and transformants were screened and grown in LB medium containing ampicillin at 20 μg/ml ampicillin. Transformants were screened using a modification of the rapid miniscreen method of Birnhoim and Doly (4). Miniprep DNA prepared as such was digested with EcoRI and BamHI and run on polyacrylamide slab gels. Several transformants which illustrated a ca. 218 bp EcoRI-BamHI insert were grown in large scale and plasmids from each were isolated and sequenced according to the procedure of Maxam and Gilbert (5) to confirm the correct chemical synthesis and construction. The pBR322 vector containing the complete correct left half sequence of IGF-1 was called IGF-1 LH322 (see FIG. 5; *SEQ ID NOS. 36–41*).

Cloning of Fragments of the Right Half of IGF-1

Figure 6:
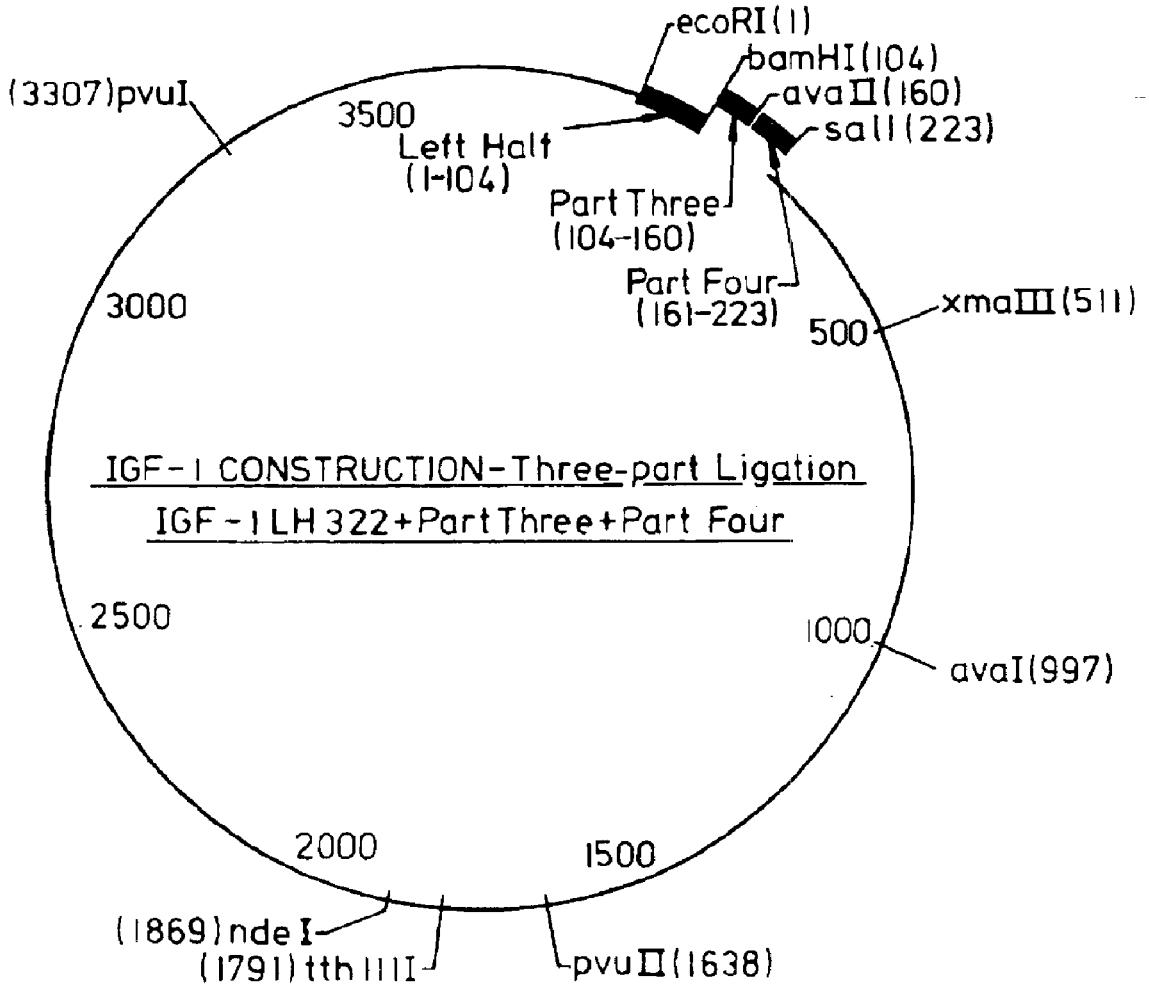
FIG. 6 depicts the ligation of parts 3 and 4 of FIG. 5 into the vector of FIG. 4.

Using the identical conditions of DNA Polymerase I-mediated repair-synthesis, the two pairs of fragments comprising the right half of the synthetic IGF-1 were converted into double-stranded DNAs. After the DNA Polymerase I reactions, and without enzymatic digestion, the 1R+3R (Part III) and 2R+4R (Part IV) reactions were run on a 6 percent polyacrylamide slab gels. The 83 bp (Part III) and 91 bp (Part IV) bands were located by autoradiography and cut from the gel. After electroelution the ethanol precipitated double-stranded DNAs were dC-tailed (see FIG. 6) using the procedures of Villa-Komaroff et al. (6) and Rowenkamp and Firtel (7). Reactions were carried out in 50 μl vols. of 1×tailing mix (cont. 0.2M Pot. Cacodylate, 25 mM Tris HCl pH 6.9, 2 mM DTT, 0.5 mM $CoCl_2$) and 22 μm dCTP. After prewarming at 37° for 10", The 150 second reaction was begun by the addition of 10–20 units of terminal nucleotidyl transferase and terminated by addition of EDTA followed by phenol extraction, $CHCl_3$ extraction 2×, and ethanol precipitation.

These oligo (dC) tailed Parts III and IV were then separately mixed with equimolar amounts of oligo (dG)- tailed PstI cut pBR322 vector in 50 μl of 1×annealing buffer (0.1M NaCl; 10 mM Tris HCl pH 7.8, 1 mM EDTA) at a final DNA concentration of 1–2 μg/ml. After heating to 75° C., the mixes were gradually cooled to 4° over a period of 16 hr and the mix transformed into competent E. coli 294 cells prepared according to the procedure of Dagert and Ehrlich (3). Transformed cells were plated on LB-Tetracycline-Agar plates and grown in LB-Tetracycline medium at tetracycline concentrations of 5 μg/ml. Tetracycline resistant transformants were picked and plated onto LB-Ampicillin-Agar plates to check for insertions at the PstI site. Several tetracycline resistant, Ampicillin-sensitive colonies for each Part 3 and 4 were miniscreened and those exhibiting insertions at the PstI locus were grown in large scale and sequenced by the Maxam and Gilbert technique (5) to confirm the correct DNA sequences of Parts 3 and 4.

Construction of an Intact Synthetic HuIGF-1 Coding Sequence

Preparation: Parts 3 and 4

Parts 3 and 4 Were separately removed from their vectors by digestions of 20 μg of each vector with AvaII in 2×AvaII buffer (60 mM NaCl, 6 mM Tris-HCl (pH 8.0); 10 nM $MgCl_2$; 6 mM 2-mercaptoethanol) and 30 U of AvaII. After 6hr., at 37°, EDTA was added to the 150 μl reactions to a concentration of 15 mM and the material phenol extracted, $CHCl_3$ extracted 2× and ethanol precipitated. The Part 3 pellet was then taken up in 1×BamHI buffer and digested in a volume of 150 μl with 30 U BamHI at 37° for 4 hr. The pellet containing Part 4 was digested with 30 U SalI in 150 μl of 1×SalI buffer at 37° for 4 hr.

Both digests were then run on 6 percent polyacrylamide slab gels and stained. The 51 bp band representing Part 3 and the 62 bp band representing Part 4 were removed from the gels and the DNA was electroeluted, phenol extracted, $CHCl_3$ extracted 2× and ethanol precipitated. Pellets were then taken up in $H_2O$ and were ready for ligation.

Vector Preparation

20 μg of the IGF-1 LH322 vector was digested with 50 U of BamHI and 50 U of SalI in a 200 μl reaction containing 1×BamHI buffer at 37° for 6 hr. After addition of EDTA to a concentration of 15 mM, the digestion mix was run on a 6 percent polyacrylamide slab gel, ethidium bromide stained and the 3814 bp band excised from the gel.

After electroelution, phenol extraction, chloroform extraction and ethanol precipitation, the DNA pellet was taken up in $H_2O$ and was ready for ligation with Parts 3 and 4 in a three-part ligation. The ligation was performed under conditions described above for a three-part ligation (see FIG. 7; *SEQ ID NOS. 42–43*). Parts 3 and 4 were present in the ligation mix at a 10-fold molar excess of inserts to vector. The mix was transformed into competent E. coli 294 cells prepared according to the Dagert and Ehrlich procedure (3) and plated onto LB-Ampicillin plates. Several transformants were miniscreened and two clones exhibiting a ca. 115 bp BamHi-SalI fragment were grown in large scale and their plasmids prepared. Both strands of the intact synthetic gene were sequenced by the Maxam,-Gilbert technique (5) to confirm the correct sequence. The pBR322 plasmid containing the complete correct sequence coding for Human IGF-1 was called pBR322 HuIGF-1.

Human IGF-1 Expression

IGF-1 Fusion Expression in Bacteria

Initial attempts were to obtain expression of IGF-1 as a fusion protein. To accomplish this, both the pNCV (9) and the pNCVsLE (10) expression vectors were used. (The pNCVsLE expression vector is a derivative of the pNCV vector and was prepared as follows: pNCV was treated with BglI, which cleaves at the 13 codon of the LE fusion. The site was converted to an ECoRI cleavage site using synthetic DNA, to give the expression vector pNCVsLE. The synthetic DNA introduced into the plasmid has the sequence:

5'-GATCCAGAATTC (*SEQ ID NO. 1*)

5'-GATCGAATTCTG (*SEQ ID NO. 2*) and this sequence was introduced into the plasmid:

```
GATCCAGAATTC          SEQ ID NO. 1

    GTCTTAAGCTAG      SEQ ID NO. 2
```

As a strategy to release the fused human IGF-1 protein from the trp fusion protein, a linker was designated such that an enzymatic proteolysis method reported by Wunsch et al. (8) could be applied to this expression system. To accomplish this, a DNA linker:

```
          ProAla
5'- AATTCCCTGCCG    -3'     SEQ ID NO. 3

3'      GGGACGGCCAG -5'     SEQ ID NO. 4
```

was chemically synthesized by standard methods (2) which when linked to the trp fusion protein and the IGF-1 gene, coded for the amino acid residues Proline and Alanine followed by Glycine and Proline which are the first two amino acid residues of IGF-1 and preceded by Proline and Alanine together comprise a recognition site for a collagenase isolated from Clostridium histolyticum (11,212). This enzyme reportedly acts at such a site to cleave the alanineglycine peptide bond.

To construct a DNA sequence coding for a fusion protein with a callagenase cleavage site, 30 μg pBR322 HuIGF-1 plasmid was cleaved with 50 U BamHI and 50 U PvuI enzyme in 200 μl 1×BamHI buffer at 37° for 6 hours. After addition of EDTA to a concentration of 15 mM, the reaction mix was chromatographed on a 6 percent polyacrylamide slab gel. The smaller PvuI-BamHI fragment ($^{-725}$ bp) was isolated and digested with 40 U AvaII in 150 μl 1×Sau96I buffer (60 mM NaCl, 6 mM Tris-HCl pH 7.4, 15 mM $MgCl_2$, 6 mM 2-mercaptoethanol). After addition of EDTA to a concentration of 15 mM, the resulting mix chromatographed on a 6 percent polyacrylamide slab gel. The smaller Sau96I-BamHI fragment (~86 bp) was extracted from the gel, phenol extracted, chloroform extracted 2×, and ethanol precipitated. This fragment was ready for ligation.

200 pmols of linker fragments were kinased with 100 U polynucleotide kinase in 20 μl of 1×polynucleotide kinase buffer (70 mM Tris-HCl (pH 7.6); 10 mM $MgCl_2$; 5 mM DTT; 1 mM rATP) at 37° for 1 hour. The reaction was terminated by heating to 65° C. for 5 minutes. 100 pmols of the kinased linker fragments were ligated to the 86 bp Sau96I-BamHI fragment with 400 U of T4 DNA ligase in 30 μl of 1×T4 DNA ligase buffer at 14° for 12–16 hours. The ligation reaction was terminated by addition of EDTA to a concentration of 15 mM followed by pheno extraction, chloroform extraction 2×, and ethanol precipitation. The pellet was then taken up in 1×BamHI buffer and digested in a 100 μl reaction with 50 U of EcoRI and 50 U of BamHI at 37° for 6 hrs. After terminating the digestion with EDTA, the mixture was chromatographed on a 6 percent polyacrylamide slab gel and the newly created (~97 bp) EcoRI-BamHI fragment was extracted from the gel, and prepared for ligation. The vector to receive this new fragment was prepared by digesting 30 μg pBR322 HuIGF-1 with 100 U of each EcoRI and BamHI in 100 μl of 1×BamHI buffer at 37° for 8 hr. The reaction was terminated, chromatographed on a 6 percent polyacrylamide slab gel and the larger band (~3830 bp) representing the EcoRI-BamHI digested plasmid was isolated and the plasmid DNA extracted and prepared for ligation as above. In a 30 μl ligation reaction containing a 10-fold molar excess of insert fragment to vector, the EcoRI-BamHI fragment was ligated into the EcoRI-BamHI digested plasmid pBR322 HuIGF-1 under standard ligation conditions mentioned above. Competent E. coli 294, prepared as above (3), were used as transformation hosts and the transformed cells were plated onto LB-Ampicillin agar plates. Several transformants were picked, miniscreened as above (4), and two exhibiting an EcoRI-BamHI insertion were grown in large scale and their plasmids purified. Using the Maxam-Gilbert procedure (5) the construction was sequenced to verify the correct synthesis and insertion of the EcoRI-Sau96I collagenase linker. This plasmid Was called pBR322 HuSynIGF-1-M.

To prepare this EcoRI-SalI IGF-1 coding sequence for insertion into pNCV and pNCVsLE, 30 μg of pBR322 HuSynIGF-1-M was digested with 70 U of SalI in 200 μl of 1×SalI buffer (150 mM NaCl, 6 mM Tris-HCl (pH 7.9); 6 mM $MgCl_2$; 6 mM 2-mercaptoethanol) at 37° for 6 hours. After addition of EDTA to 15 mM, the mixture was phenol extracted, chloroform extracted 2×, and ethanol precipitated.

Using standard chemical synthesis procedures (2) a SalI-EcoRI linker

```
5' TCGACGTACATG     3'      SEQ ID NO. 5

3'     GCATGTACTTAA 5'      SEQ ID NO. 6
```

was synthesized and 400 pmols kinased, as above. 200 pmols of the kinased linker was ligated to the SalI digested pBR322 HuSynIGF-1-M (prepared above) with 800 U T4 DNA ligase in 30 μl of 1×ligation buffer for 12–16 hours at 14° C.

After termination of the reaction with EDTA, the mixture was phenol extracted, chloroform extracted 2×, and ethanol precipitated. The pellet was then taken up in 1×EcoRI buffer and digested with 100 U EcoRI in a volume of 200 μl for 8 hours at 37°. After addition of EDTA to a concentration of 15 mM, the mixture was chromatographed on a 6 percent polyacrylamide slab gel. The gel was stained and the ~230 bp band corresponding to the EcoRI-EcoRI HuIGF-1 fragment was extracted from the gel, phenol extracted, chloroform extracted 2×, and ethanol precipitated. This fragment was ready for ligation into pNCV and pNCVsLE, pNCV and pNCVsLE were prepared for ligation by digestion of 20 μg of each with 100 U EcoRI in 200 μl×EcoRI buffer at 37° for 8 hours. After digestion, 200 U of bacterial alkaline phosphatase was added to each reaction and the mixtures were warmed to 65° C. for 2 hours. EDTA was added to a concentration of 15 mM and the mixes were phenol extracted 3×, chloroform extracted 2× and then ethanol precipitated. These expression vectors were prepared for ligation.

Ligations of the EcoRI-EcoRI Human IGF-1 fragment into the two expression vectors were performed in 30 μl reaction volumes in 1×T4 DNA ligase buffer with 800 U T4 DNA ligase at 14° for 12–16 hours. The EcoRI-EcoRI fragment was present at a 10-fold molar excess in vector.

Competent E. coli 294 were prepared (3) (ATCC 31446) and used as transformation hosts for the ligations. Transformed cells were plated onto LB-agar plates containing tetracycline (5 μg/ml; LB-Tet-plates) and transformants were miniscreened (4). Miniscreen plasmid DNA from transformants of the pNCV-IGF-1 construction were digested with both PstI and BGIII to determine the orientation of the EcoRI fragment insertions. Two clones whose plasmids contained a ~570 bp BgIII-PstI fragment (as opposed to a ~690 bp fragment) were grown in large scale and their plasmids prepared. The construction was sequenced using the Maxam-Gilbert procedure (5) to confirm the correct insertion at the junction of the trp fusion and IGF-1 protein coding sequences as well as retention of the desired reading frame. Plasmids with the correctly inserted IGF-1 fragment were called pNCVLE-IGF-1. Transformants of the pNCV-sLE-IGF-1 construction were also miniscreened by the same procedure (5), and the plasmid DNAs were digested with HincII and PstI. Two clones exhibiting a ~150 bp HincII-PstI fragment (as opposed to a ~105 bp HincII-HincII fragment) were grown in large scale and their plasmids prepared. Using the Maxam-Gilbert techniques (5), the functions of the trp fusion and IGF-1 protein coding sequences were sequenced to ascertain proper orientation and retention of the proper reading frame. Those plasmids possessing the correct insertion and proper reading frame were called pNCV-sLe-IGF-1.

To attempt expression of each of these constructions, two clones, one possessing pNCV-IGF-1 and the other possessing pNCV-sLE-IGF-1, were inoculated into 10 ml M9-Tetracycline culture medium supplemented with 0.5 mg/ml Tryptophan. A clone containing pNCV-LE with no IGF-1 gene insert was also inoculated into culture medium to provide as a negative control in assays.

After 12–16 hours growth at 37° with agitation, 0.5 ml of these cultures were used to inoculate 250 milliliters of M9-Tetracycline culture medium. After growing for 12–16 hours at 37° with agitation, the cells were harvested by centrifugation at 5000 rpm for 10 minutes in a Sorvall GSA rotor. The refractile bodies were purified from the pelleted cells by: a) suspending the host cells in a buffered solution of ionic strength suitable to solubilize most of the host protein, b) subjecting the suspension to cell wall/membrane disruption, c) centrifuging the disrupted suspension at low speed to form a pellet, optionally repeating the foregoing steps, and d) recovering the heterologous protein as refractile bodies in the pellet (Reference 13). A small quantity of refractile particles of each of the three preparations was boiled in SDS and 2-mercaptoethanol containing sample buffer and run on SDS-polyacrylamide slab gels according to the Laemmli method (14). The size of the protein expressed by pNCV-IGF-1 (LE-IGF-1) was ~28,670 Daltons (see FIG. 7; *SEQ ID NOS. 42–43*), and ~9770 Daltons for the pNCV-sLE-IGF-1 protein (sLE-IGF-1) (see FIG. 8; *SEQ ID NOS. 44–45*). These two expressed proteins were subjected to solubilization in 6M Guanidine-HCl followed by 50-fold dilution with dilute buffers. The final buffer for pNCV-IGF-1 after dilution was 0.12 M Guanidine-HCl; 0.05 M 7922 Tris-HCl pH 8, 20 percent glycerol; 0.1 mg/ml BSA; 0.15 M NaCl; 0.1 mM EDTA and the final buffer after dilution of the pNCV-sLE-IGF-1 refractile bodies was 0.14 M Guanidine-HCl; 25 mM Tris-CHl pH 7.6; 10 mM $CaCl_2$. After spinning out particulate matter, the two solutions containing solubilized trp-IGF-1 fusion proteins were assayed by a radioimmune assay procedure of Furlanetto et al. (23), as modified by Hintz et al. (24). Both fusion proteins demonstrated activity in this assay. A negative control prep was also included in the assay and the control exhibited no measurable activity.

Expression and Secretion in Yeast

To avoid the necessity of refractile body purification and solubilization, from bacterial cell lysates, yeast expression-secretion systems were sought as an alternative. Aside from the advantage of avoiding protein purification from cell lysates, coupled expression-secretion systems might obviate a subsequent in vitro processing step to remove a fused protein. Available were three yeast expression-secretion systems. These were: 1) yeast a factor (22), employing yeast α-factor promoter and preprosequence; 2) yeast invertase (16) consisting of the invertase promoter and signal sequence; and 3) a hybrid composed of the PGK promoter (25) and invertase signal (16).

Yeast Alpha-Factor Promoter Pre-Alpha Factor IGF-1 Plasmid Construction

Figure 9:
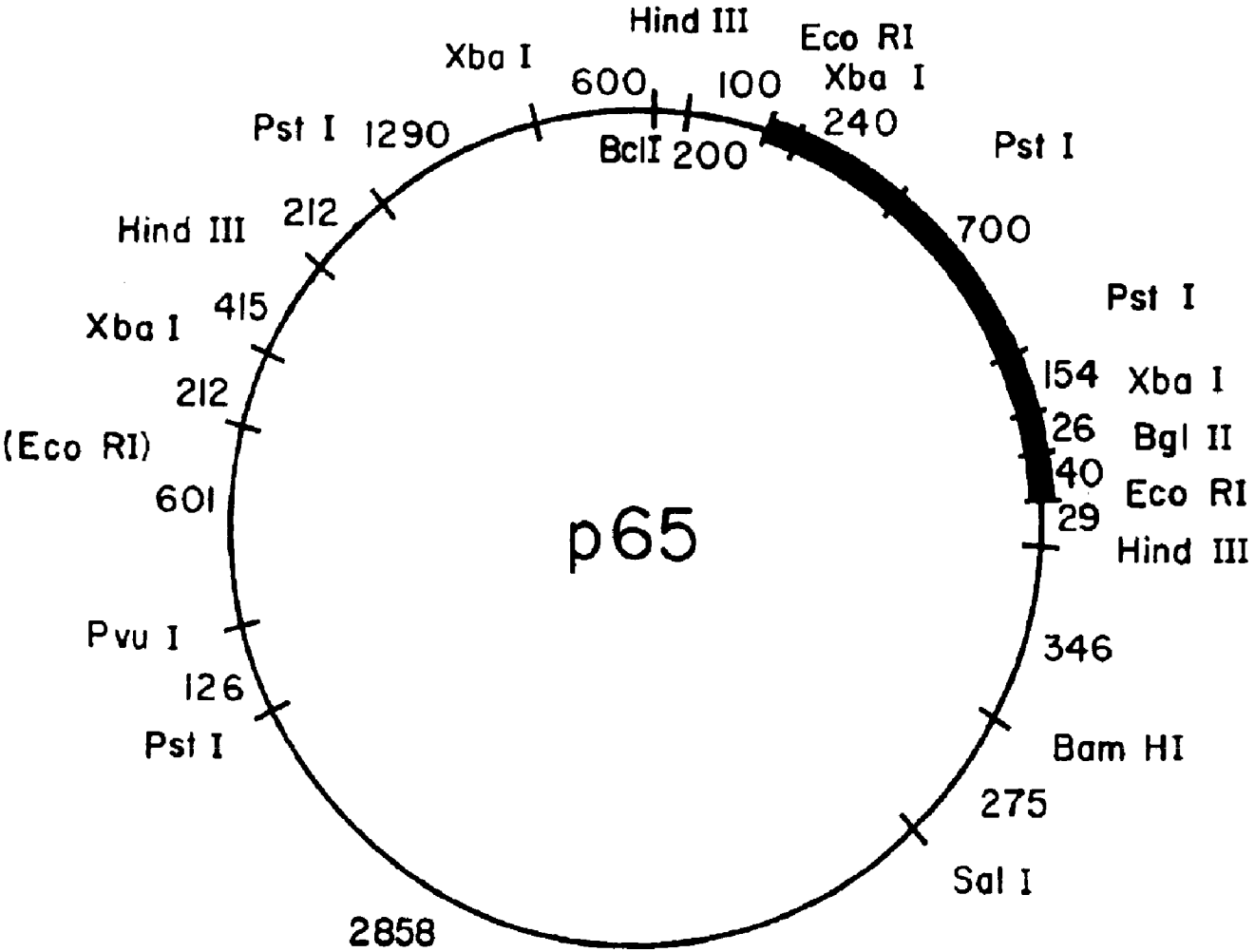
FIG. 9 depicts a plasmid used in the present construction.

To obtain expression of IGF-1 using the a factor promoter and preprosequence, a plasmid constructed by Singh (22) was used. Plasmid P65 (FIG. 9) possesses sequences of the α-factor promoter, α-factor preprosequence, yeast 2 micron terminator, the yeast Trp 1 gene, as well as portions of the pBR322 plasmid. Plasmid p65 was obtained by its following method: The 15-mer oligonucleotide probes for the α-factor gene were designed on the basis of the amino acid sequence of the pheromone (23a) and yeast codon usage frequencies. The rationale is outlined in FIG. 19 (*SEQ ID NOS. 57–60*) where the last 5 amino acids of the α-factor and all the possible codons and their usage frequencies are given. (The codon usage is the total of 2 different glyceraldehyde-3-phosphate dehydrogenase clones (23b, 23c) and of alcohol dehydrogenase I.) The codon usage for these and other genes has recently been summarized identical, to the MFα1. The α-factor encoded by this gene is apparently made as a precursor protein of 120 amino acid residues containing two copies of the pheromone. One of the α-pheromone tridecapeptides contained in the putative precursor is identical to the pheromone copies encoded by the MFα1 gene, whereas the second copy contains a Gln→Asn and a Lys→Arg.

E. Construction of a Plasmid p65 for Expression and Secretion of Human Interferon The preparation of a plasmid to demonstrate the usefulness of the α-factor promoter and the α-factor presequences for expression and secretion of heterologous gene products is outlined in FIGS. 23–24. The DNA sequences coding for the α-factor peptides were removed from one of the α-factor clones (p53) such that the resulting plasmid, p57, contained the promoter sequences and the sequence corresponding to 89 amino acids of the α-factor "prepro" protein. This sequence was then joined with human interferon D (IFN-$\alpha_1$) gene to form plasmid p58. For this purpose an expression plasmid p65 was constructed as shown in FIG. 24. This plasmid, like YEp9T, contains the origins of replication for E. coli and yeast as well as selective markers for selection in each of these two organisms. It also contains a convenient EcoRI site for gene insertion so that any gene that is contained on an EcoRI fragment where the first codon of the gene is immediately preceded by the EcoRI site could be tested for the synthesis and secretion of the corresponding protein. Due to the dearth of convenient restriction sites in the α-factor preprosequence, to insert the IGF-1 coding sequence, the identical ~230 bp EcoRI-EcoRI HuSynIGF-1-M fragment that was ligated into pNCV and pNCVsLE (as mentioned previously in bacterial construction) was used. This EcoRI-EcoRI fragment contained the collagenase recognition site Proline-Alanine-Glycine-Proline, and allowed for collagenase digestion should IGF-1 be secreted as a fusion protein. The protein expressed in this construction (see FIG. 10; *SEQ ID NOS. 46–47*) consists of the repro α-factor protein fused to IGF-1.

To insert the ~230 bp EcoRI-EcoRI fragment, the plasmid P65 was partially digested in 1×EcoRI buffer with EcoRI, and then sized upon a 0.7 percent horizontal agarose gel. The band corresponding to the linearized singularly restricted plasmid was excised, eluted from the gel, and phenol extracted, chloroform extracted 2×, and then ethanol precipitated. This DNA pellet was then taken up in 50 mM Tris-HCl (pH 8) and treated with bacterial alkaline phosphatase under conditions to ensure 100 percent dephosphorylation of the 5' protruding ends. Following this treatment, the phosphatase activity was removed by first adding EDTA to a concentration of 15 mM, then extracting the DNA with phenol 3×, chloroform extracting 2×, and ethanol precipitating the vector. This material then contained linearized P65 vector, digested with EcoRI in either of two locations: one, either at the EcoRI site upstream of the α-factor promoter and preprosequence, or at another, at the EcoRI site just downstream of the α-factor promoter and preprosequence. The ~230 bp EcoRI-EcoRI IGF-1 fragment was ligated into the vector. The desired location of insertion was at the EcoRI site just downstream from the α-factor promoter and preprosequence.

Figure 11:
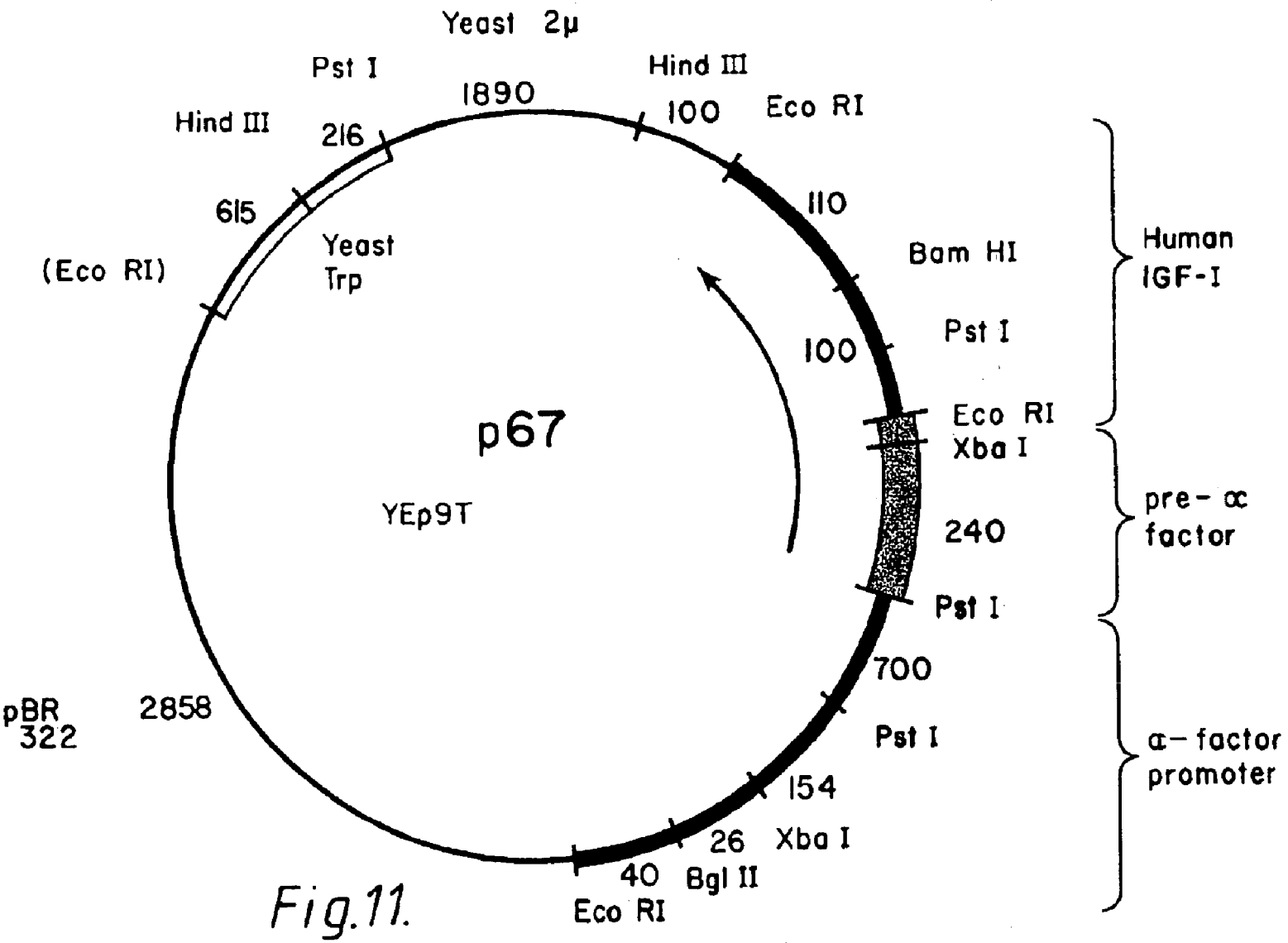
FIG. 11 is a vector containing alpha factor promotor and pre-pro sequence fused to IGF-I.

The ligation was carried out under standard ligation conditions and the transformation hosts were competent E. coli 294 prepared according to Dagert and Ehrlich (3). The transformed cells were plated onto LB-Amp-Agar plates. Several transformants were miniscreened according to the method of Birnboim and Doly (4), and plasmid DNA prepared as such was digested with both SaLI and HINDIII in the appropriate buffers. One of several clones which contained a plasmid with an ~110 bp EcoRI-HindIII fragment was grown in large scale and its plasmid was purified. This plasmid, YEp9T α-factor EcoRI-EcoRI IGF-1 (see FIG. 11), was used to transform competent yeast strain 20B-12 (atrp $pep^4$) cells according to the Hitzeman modification (19) of Hinnen et al. (17) and Beggs et al. (18) procedures.

Two such transformants, as well as a negative control transformant (with no IGF-1 insertion in the plasmid), were grown in suspension as were those of the yeast pre-invertase-IGF-1 plasmid transformations. Supernates were tested for secreted IGF-1 activity, as measured by the radioimmune assay procedure of Furlanetto et al. (23) as modified by Hintz et al. (24). Both supernates of transformants having plasmids with IGF-1 inserts contained IGF-1 activity and the negative control supernate did not. One of these transformants was grown in large scale in a 10 liter fermenter and the supernate contained secreted IGF-1 activity at a peak level of ~3 μg/ml. The IGF-1 activity of the fermentation supernate was also demonstrated by a placental membrane radioreceptor assay developed by Horner et al. (26).

Yeast Invertase Promoter Signal IGF-1 Plasmid Construction

Based upon evidence of correct processing and secretion in yeast of proteins with heterologous signal sequences (16), the yeast invertase expression-secretion system became of interest. Attempted first was expression of the yeast invertase signal protein fused to IGF-1 (FIG. 12*SEQ ID NOS. 48–49*), coupled with the processing and secretion of IGF-1, using the invertase promoter as a starting point for transcription.

The yeast invertase signal coding sequence was attached to the IGF-1 gene by the use of a NcoI-HindIII (~400 bp) fragment containing the initiation ATG codon and 5' end of the signal DNA sequence, and 4 DNA fragments synthesized by standard procedures (2):

```
5' AGCTTTCCTTTTCCTTTTGGC      3'    SEQ ID NO. 7

3'     AAGGAAAAGGAAAACCGACCAA 5'    SEQ ID NO. 8

5' TGGTTTTGCAGCCAAAATATCTGCAG    3'  SEQ ID NO. 9

3'      AACGTCGGTTTTATAGACGTCCAG 5'  SEQ ID NO. 10
```

The construction began with the isolation of the 90 bp AvaII-BamHI IGF-1 left half fragment by AvaII digestion of a ~730 bp PvuI-VamHI fragment isolated from PvuI-BamHI digested pBR322-HuSynGF-1.

After phosphorylation of all four synthetic DNA fragments using standard kination conditons, the four synthetic fragments were mixed with the AvII-BamHI IGF-1 left half fragment and ligated using standard ligation conditions. Following inactivation of the ligase by phenol and chloroform extraction 2×, the ethanol precipitated DNA pellet was dissolved and digested with HindIII and BamHI in the appropriate buffers. Newly constructed HindIII-BamHI (ca. 140 bp) fragment was isolated and extracted from a 6 percent polyacrylamide gel. This material was then ligated into HindIII-BamHI digested pBR322 vector, which had been first digested with HindIII, then BamIII in the appropriate buffers, followed by purification of the 4014 bp vector fragment from a 6 percent gel.

The transformation host was competent E. coli 294 prepared by standard procedures (3) and the transformed cells were plated onto LB-Ampicillin agar plates. Several tranformants were miniscreened by the Birnboim-Doly procedure (4) and their plasmid DNAs digested with EcoRI and BamHI. Two plasmids containing a ~bp EcoRI-BamHI fragment (illustrating the insertion of a 140 bp fragment into the HindIII and BamHI sites) were grown in large scale and their plasmids prepared. Using Maxam-Gilbert sequencing techniques (5), the entire 43 bp HindIII-AvaII section of DNA was sequenced to confirm the correct chemical synthesis and construction. The correctly constructed plasmid was called pBR322-P-I-HuSynIGF HindIII-BamHI (~4154 bp).

To insert the right half of the IGF-1 gene, this newly created plasmid was digested with BamHI-SalI in the appropriate buffers and the larger fragment (~3879 bp) was purified by gel fractionation. pBR322 HuSynIGF was digested with BamHI-SalI in the appropriate buffers and the 115 bp BamHI-SalI fragment corresponding to the right half of the IGF-1 gene was isolated by gel fractionation. This 115 bp BAMIII-SalI IGF-1 right half fragment was then ligated into the BamHI-SalI digested pBR322-P-I-IGF-1 LH HindIII-BamHI vector using standard ligation conditions. Competent E. coli strain 294 prepared according to Dagert and Ehrlich (3) were used as transformation hosts and transformed cells were plated onto LB-Amp-Agar plates. Several transformants were miniscreened using standard techniques (4) and plasmid DNA prepared as such was digested with EcoRI and SalI in the appropriate buffers and those plasmids illustrating an insertion of the BamHi SalI fragment corresponding to the right half of IGF-1 were called PBR322 P-I-HuSynIGF-1 HindIII-SalI. One of the clones containing the pBR322 P-I-IGF-1 HindIII-SalI plasmid was grown in large scale and the plasmid was isolated. This plasmid was then digested with HindIII and SalI in the appropriate buffer to prepare a 255 bp HindIII-SalI fragment containing all of the IGF-1 gene and the 3' portion of the yeast invertase signal coding sequence. This fragment of DNA was isolated by polyacrylamide gel fractionation and prepared for ligation by standard techniques. The (~400 bp) NcoI-HindIII fragment containing the 5' end of the DNA sequence coding for the invertase signal as well as the yeast invertase promoter was created by NcoI and HindIII digestion of plasmid Ylpsp-LelFA (16) in the appropriate buffers. The YIpsp-LelFA plasmid was first digested with NcoI to completion in the appropriate buffer, then phenol extracted, chloroform extracted 2× and ethanol precipitated. The linearized molecules were then taken up in 1×HindIII buffer and partially digested to generate the needed NcoI-HindIII (~400 bp) fragment which contains an internal HindIII restriction site. This NcoI-HindIII fragment was then isolated by gel fractionation and prepared for ligation using standard techniques. To provide for a vector, plasmid pUC12-YI (EcoRI-BamHI)(designated p4.3 kb in citation 16) was digested with NcoI and SalI in the appropriate buffers. After purification by gel fractionation, the ~2.6 kbp vector was eluted from the gel and prepared for ligation by standard techniques. To perform the final construction, a three-part ligation was arranged using standard ligation techniques. The DNA used in the ligation included the NcoI-SalI-digested pUC12-1 (EcoRI-BamHI) (16), the ~400 bp NcoI-HindIII and the ~255 bp HindIII-SalI fragments. After ligation, the material was transformed into competent E. coli 294 cells prepared according to Dagert et al. (3). Transformed cells were plated onto LB-Amp-Agar plates and several transformants were miniscreened using the procedure of Birnboim and Doly (4). Plasmid DNA prepared as such was digested with NcoI and SalI in the appropriate buffers and one of several clones containing plasmids exhibiting the insertion of a ~625 bp NcoI-SalI DNA fragment was grown in large scale and its plasmid was purified.

As a final step, this plasmid was linearized by digestion with SalI in the appropriate buffer. SalI-EcoRI linker, prepared as mentioned above, and kinased under standard kination conditions, was ligated to the linearized vector to convert the SalI ends to EcoRI ends using standard ligation conditions. After termination of the ligation reaction by addition of EDTA to 15 mM, phenol extraction, chloroform extraction 2× and ethanol precipitation, the DNA pellet was dissolved in 1×EcoRI buffer, and digested with EcoRI. The EcoRI digestion released a ~1150 bp EcoRI fragment which contained the yeast invertase promoter, yeast invertase signal coding sequence and the IGF-1 coding sequence in one contiguous sequence. This material was isolated as a ~1150 bp band from a 6 percent polyacrylamide slab get after fractionation and prepared for ligation using standard procedures.

The yeast-E. coli shuttle vector to receive the EcoRI fragment was prepared by EcoRI digestion of plasmid YEp9T (16) to-linearize the vector, followed by treatment of the EcoRI termini with bacterial alkaline phosphatase using conditions recommended by the manufacturer to produce 100 percent dephosphorylation of the 5' protruding ends. The phosphatase reaction was terminated by addition of EDTA to 15 mM and the mixture phenol extracted 3×, chloroform extracted 2×, and then the DNA was ethanol precipitated. After redissolving the DNA pellet in 1×ligation buffer, the vector was mixed with the EcoRI ~1150 bp fragment and ligated under standard ligation conditions. Competent E. coli 294 cells prepared according to Dagert et al. (3) were used as transformation hosts and the transformants were placed onto LB-Amp-Agar plates. To determine the orientation of the insertion, several transformants were miniscreened using the method of Birnboim and Doly (4) and plasmid DNAs purified as such were digested with BamHI in the appropriate buffer. One of several transformants possessing plasmids which produced a 1.3 kb BamHI-BamHI fragment upon BamHI digestion (as opposed to a ~475 bp fragment) was grown in large scale and its plasmid was purified. This plasmid, called P.I.IGF-1 EcorRI-EcoRI P.I. Promoter was used to transform competent yeast cells prepared essentially according to the methods of Hinnen, A., et al. (17), and Beggs, J. D. (18), but with the modification of Hitzeman (19). The yeast strain 20B-12 (αtrpl pep4) was used and was obtained from the Yeast Genetics Stock Center. In this construction, the expression of IGF-1 begins With transcription at the invertase promoter and terminates in the yeast 2 micron sequence. The fusion protein expressed by this construction consisted of the yeast invertase signal fused to the IGF-1 protein, the combined molecular weight of which was 9964 Daltons. Another plasmid with the EcoRI fragment inserted in the reverse orientation was also used to transform competent yeast cells. In this construction, the IGF-1 was not provided with the yeast terminator.

Several transformants were picked and streaked on YNB-CAA agar plates. Among these, three transformants were picked and inoculated into 10 ml of YN3-CAA grow-up medium, in shake flasks. A fourth culture was also started using a colony transformed with the same vector, but with the EcoRI fragment inserted into the vector in the reverse orientation. After 16–20 hours growth at 30°, the cultures were sampled (1 ml) and cleared of cells by spinning 5' in an eppendorf microfuge. Supernatants were taken off and assayed for secreted activity using the radioimmune assay procedure of Furlanetto et al. (23) as modified by Hintz et al. (24). The supernates of the three transformants demonstrated activities of 1.7 to 3.3 ng/ml of IGF-1 activity and the negative control showed no activity. To determine intracellular activity, the pellets from 1 ml of culture were washed 1×in 25 mM Tris-HCl (pH 7.6), 1 mM EDTA and then lysed by 3–4 minutes of vigorous vortexing in 0.5 ml of the above Tris-EDTA solution with 0.4 ml of glass beads.

Assay of the cell lysates demonstrated IGF-1 activities of 1.5–2.8 ng/ml in the three IGF-1 secreting transformants and no activity in the negative control transformant. The highest secretor of the three transformants was grown in a 5 liter fermentation and the secreted IGF-1 activity reached a peak of 74 ng/ml of supernate.

Yeast PGK Promoter Pre-Invertase IGF-1 Plasmid Construction

One difficulty in the use of the invertase promoter was that it was subject to repression in the presence of glucose. Due to the incompatibility of glucose with high levels of transcription initiation at the invertase promoter, the PGK promoter was sought as an alternative promoter, glucose, being the mainstay carbon source of fermentation processes.

To begin construction of the PGK promoter P.I.IGF-1 construction, it was necessary to clone a fragment containing the entire invertase signal coding sequence. To do this, plasmid pLeIF-A-Invertase Signal (16) was digested with BgIII and then BamHI in the appropriate buffers. This digestion released several fragments, one of which was a ~625 bp BgIII-BamHI fragment which was isolated from a 6 percent polyacrylamide slab gel and prepared for ligation using standard techniques. To clone this fragment, the pUC8 vector was chosen as a cloning vehicle. pUC8 plasmid was digested with BamHI in 1×BamHI buffer, treated with bacterial alkaline phosphatase to dephosphorylate the 5' termini, and then run onto and purified from a 5 percent polyacrylamide slab gel.

After standard preparation for ligation the BamHI digested vector was mixed with the above ~625 bp BgIII-BamHI fragment, and ligated under typical ligation conditions. The mixture was then transformed into competent E. coli 294 prepared by the Dagert et al. method (3) and the transformed culture plated onto LB-Amp-Agar plates. Several transformants were picked and miniscreened using the Birnboim and Doly (4) technique. Miniscreen plasmid DNA was digested with EcoRI and an analytical gel of the digests illustrated two types of plasmids having EcoRI fragments either ~260 bp or ~385 bp in length. One clone containing a ~260 bp EcoRI fragment was grown in large scale and its plasmid purified. This plasmid was called pUC8P.I. Promoter-Signal BgIII-BamHI.

A clone of this type was chosen because of the desired orientation of the inserted BgIII-BamHI fragment. What was needed from this plasmid was an ~20 bp EcoRI-HindIII fragment containing the ATG initiation condon and 5' end of the invertase signal coding sequence.

To construct the intact invertase signal coding DNA sequence, ~150 bp HindIII-BamHI fragment containing the 3' end of the signal sequence fused to the left half of the IGF-1 gene was isolated from HindIII-BamHI digestion of plasmid pBR322 P.I. IGF-LH HindIII-BamHI (~4154 bp). Isolation was by polyacrylamide slab gel fractionation, and the DNA band corresponding to the ~150 bp fragment was excised and prepared for ligation using standard techniques.

To obtain the short (~20 bp) EcoRI-HindIII fragment, the plasmid pUC8 P.I. Promoter-Signal-BgIII-BamHI was digested with EcoRI in 1×EcoRI buffer. This digestion released the ~260 bp EcoRI-EcoRI fragment which was isolated from a 6 percent polyacrylamide slab gel after fractionation of the digestion mixture. This ~260 bp fragment was then digested with HindIII in the appropriate buffer, causing the creation of two. HindIII-EcoRI fragments, one ~20 bp and the other ~240 bp in length. After complete digestion, the digestion was terminated by addition of EDTA to 15 mM and the entire mix phenol extracted, chloroform extracted 2×, and then ethanol precipitated.

A vector was prepared by EcoRI-BamHI digestion of pBR322 (15) in the appropriate buffers followed by purification of the EcoRI-BamHI digested vector from a 5 percent polyacrylamide slab gel. After preparation for ligation using standard techniques, the vector was mixed with the ~150 bp HindIII-BamHI fragment (3' end of invertase signal +Left Half IGF-1), and the two HindIII-EcoRI fragments (the ~20 bp fragment containing the 5' end of the invertase signal coding sequence), and the entire mixture was ligated under standard ligation conditions. Competent E. coli 294 prepared according to Dagert and Ehrlich (3) were used as transformation hosts for the ligation, and the transformed cells plated onto LB-Amp-Agar plates. Several transformants were miniscreened according to Birnboim and Doly (4) and the purified miniscreen DNAs were digested with EcoRI and BamHI. One of several clones possessing an ~170 bp EcoRI-BamHI fragment was grown in large volume and its plasmid purified. This plasmid contained the complete yeast invertase signal coding sequence fused to the left half of IGF-1 and was called P.I. IGF-1 L.H. RI-BamHI.

The desired ~170 bp EcoRI-BamHI fragment was isolated from this plasmid by digestion of the plasmid with EcoRI and BamHI in the appropriate buffers followed by slab gel fractionation of the reaction mix. Using standard techniques, the ~170 bp band of DNA was prepared for ligation. To complete the construction, the right half of IGF-1 was isolated as an ~120 bp BAMHI-EcoRI fragment from the plasmid P.I. IGF-1 EcoRI-EcoRI-P.I. Promoter by digestion with EcoRI and BamHI in the appropriate buffers followed by elution from a gel slice after polyacrylamide slab gel fractionation of the digestion mixtures. These two fragments the ~170 bp EcoRI-BamHI and the ~120 bp BamHI-EcoRI, were ligated together in vitro under standard ligation conditions, with both fragments present in roughly equimolar concentrations. This ligation mixture was then terminated by the addition of EDTA to ~15 mM followed by phenol extraction, chloroform extraction 2×, and ethanol precipitation. The DNA pellet was then taken up in 1×ExoRI buffer and digested with EcoRI. The digest was then run on a 6 percent polyacrylamide slab gel and the DNA band staining at ~290 bp (as opposed to ~340 bp and 240 bp) was excised and prepared for ligation using standard techniques. This ~290 bp EcoRI-EcoRI fragment contained the entire yeast invertase signal coding sequence fused to the complete IGF-1 coding sequence.

Figure 13:
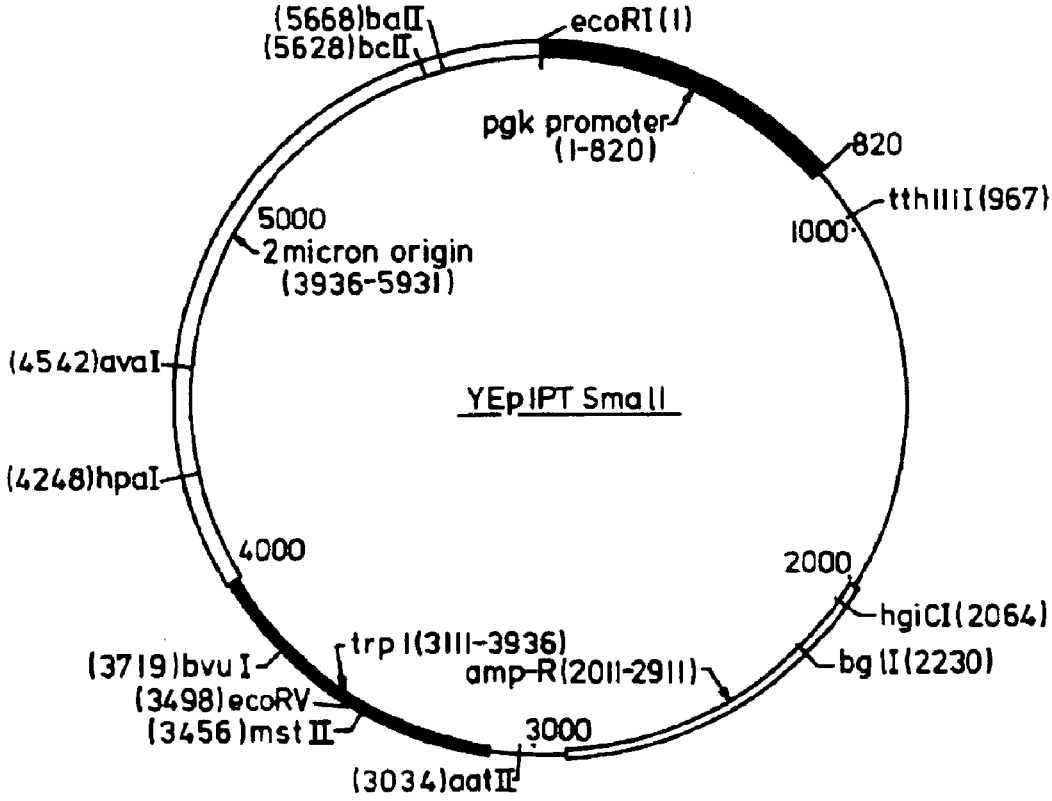
FIG. 13 shows the parental plasmid containing the yeast PGK promoter.

To express this protein, it was necessary to select a yeast vector with a promoter. The PGK promoter of the plasmid YEp1PT Small (see FIG. 13) was used. YEp1PT Small was constructed as a derivative of YEp1PT (21) by ClaI and PvuII digestion of YEp1PT in the appropriate buffers. The ClaI 5' protruding end was converted to a blund end by use of DNA polymerase 1 (Klenow) under conditions recommended by the vendor. After blunting the (ClaI protruding ends, the blunt ends ClaI and PvuII) of the linearized vector were fused using T4 DNA ligase under standard ligation conditions. The resultant YEp1PT small vector was ~5.9 kbp in size (or ~2.7 kbp smaller than YEp1PT). Just as YEp1PT, YEp1PT small possesses the 2 micron origin and terminator, the PGK promoter, the TRP1 gene, and sequences from pBR322, including the β-lactamase gene.

YEp1PT Small was employed as a vector by insertion of the ~290 bp EcoRI fragment into the unique EcoRI site of the plasmid. EcoRI linearized YEp1PT Small vector was prepared by EcoRI digestion of YEp1PT Small followed by bacterial alkaline phosphatase (BAP) treatment (to prevent religation of the complementary termini). The BAP Was removed by phenol extraction 3×, chloroform extraction 2×, and ethanol precipitation. Under standard ligation conditions, the ~290 bp EcoRI fragment was ligated into the vector.

Figure 14:
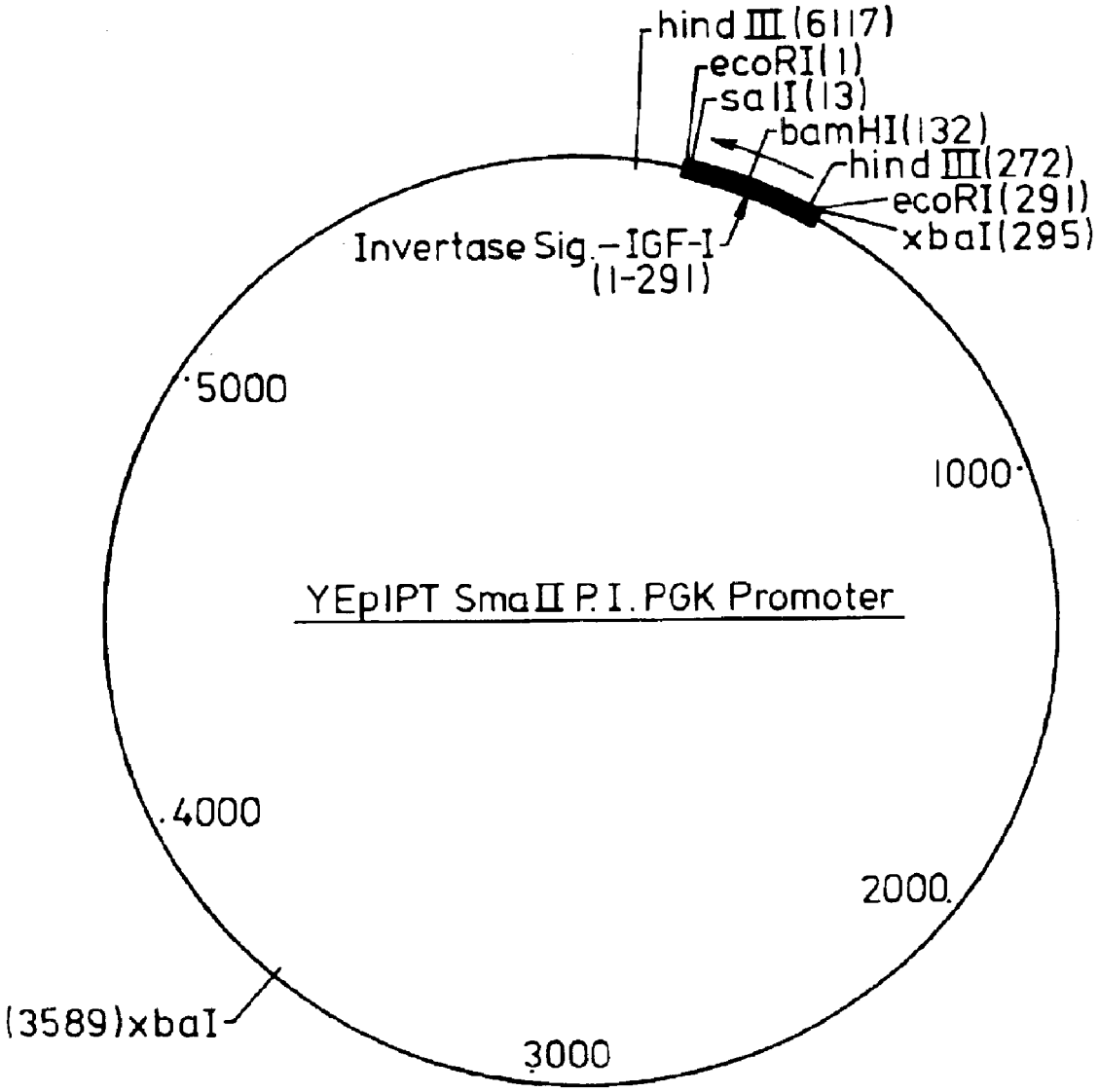
FIG. 14 depicts a yeast expression vector containing PGK promoter, invertase signal and human IGF-I gene.
Figure 20A:
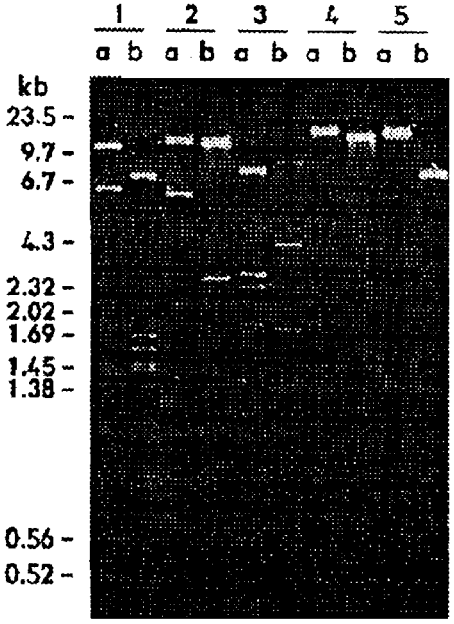
FIGS. 20A and 20B illustrate the results of electrophoresis of DNA fragments obtained using the probes of FIG. 19.
Figure 20B:
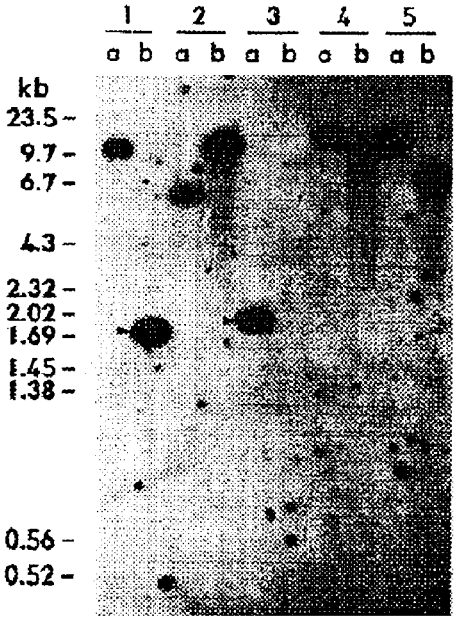

Competent E. coli 294 prepared according to Dagert and Ehrlich (3) were used as transformation hosts and the transformed culture was plated onto LB-Amp-Agar plates. Several transformants were miniscreened by the Birnboim and Doly procedure (4) and miniscreen plasmid DNAs were digested with HindIII in the appropriate buffer to determine the orientation of the insert. One of several transformants possessing a plasmid with a ~400 bp HindIII fragment was grown in large scale and its plasmid was purified. This plasmid was called YEp1PT Small P.I. IGF-1 PGK promoter (see FIG. 14) and was used to transform competent yeast strain 20B-12 (ATCC 200626) (αtrp pep4) cells employing the Hitzeman modification (19) of Hinnen et al. (17), and Beggs et al. (18) procedures.

Several yeast transformants were grown in suspension in identical fashion as were those of the P.I. IGF-1 EcoRI-EcoRI P.I. promoter plasmid transformation and supernates were measured for activity determined by a radioimmune assay method of Furlanetto et al. (23) as modified by Hintz et al. (24). Shake flask supernates of three transformants contained activities ranging from 38 to 53 ng/ml of supernate. Similarly, one of these transformants was selected and grown in larger scale, utilizing a 10 liter fermenter and the secreted IGF-1 activity in the supernate reached a peak of ~780 ng/ml. This fermentation supernate was also subjected to a radioreceptor assay (26) and was demonstrated to contain IGF-1 activity.

Stature Human IGF Production

To construct a DNA sequence coding for the α-factor pre-pro protein fused to the DNA sequence coding for mature IGF-1, and M-13 in vitro mutagenesis technique was employed (See Regin et al., Proc. Acad. Science (USA) 75, 4208; Hutchinson, et al., Journal Biological Chem. 253, 6551; Gilliam, et al., Gene 8, 81 an 99; Gillam, et al., Nucleic Acids Research 6, 2973; Adelman, et al., DNA (June, 1983).)

To construct the M13 plasmid, the plasmid YEp9T α-factor EcoRI-EcoRI IGF-1 (FIG. 16; *SEQ ID NOS. 51–52*) was digested with BglII and SalI and the ca. 1.5 Kbp fragment containing the α-factor promoter-signal fused to IGF-1 was isolated by polyacrylamide gel electrophoresis. This fragment was then ligated under standard ligation conditions to an MP-8 (BRL) vector digested with B3BamHI and SalI, and treated with bacterial alkaline phosphatase. This ligation mix was then transformed into competent JM4101 cells prepared according to the method of Dagert and Ehrlich (3). These transformants were then mixed with non-competent JM101 cells grown to log phase, mixed with top agar and plated onto LB agar plates. Several clear plaques [W]*were* picked and sequenced using M-13 dideoxy sequencing technique to confirm the presence of an insertion into the SalI-BamHI sites of the vector.

To perform the deletion according to the method above, a single strand of DNA of the sequence.

5' AGAGTTTCCGGACCG CTT TTATCCAAAG 3' *SEQ ID NO. 11* was chemically synthesized by standard methods (2) and used to delete the DNA sequence.

```
5' GAGGCTGAAGCTCTAGAATTCCCTGCC 3'    SEQ ID NO. 12

3' CTCCGACTTCGAGATCTTAAGGGACGG 5'    SEQ ID NO. 13
```

just preceding the IGF-1 coding sequence of the α-factor promotor/signal IGF-1 fusion sequence. This construction was then isolated as a replicate form, using a large scale plasmid preparation procedure from a JM101 cell culture inoculated with this plasmid containing the deletion.

The isolated replicate form (10 mg) Was then digested with SalI, phenol-chloroform extracted and then ethanol precipitated and prepared for ligation. To this replicate form was ligated Sal I-EcoRI linkers. After ligation and inactivation of the ligase by phenol, chloroform extraction followed by ethanol precipitation, the material was digested with ~50 U EcoRI enzyme under standard conditions and then run onto a 6 percent polyacrylamide gel. The ca. 1.5 khp RI-EcoRI fragment released was isolated from the gel and prepared for ligation using standard conditions.

Yeast vector was prepared by digestion of 10 mg YEP9T plasmid with 50 units of EcoRI followed by treatment with bacteral alkaline phosphatase. The digestion was then repeatedly phenol-chloroform extracted and then ethanol precipitated and prepared for ligation.

The ca. 1.5 kbp EcoRI-EcoRI fragment containing the deletion was then ligated to the EcoRI-EcoRI YEP9t vector and the ligation mix was then transferred into competent 294 cells prepared according to the method of Dagert and Erhlich (3) and miniscreened using the method of Birnboin and Doly (4). DNA prepared was screened by digestion with EcoRI and those DNAs illustrating an insertion of the ca. 1.5 kbp fragment were used to transform competent yeast strain 20B-12 (ATCC 2026) according to the modification of Ilitzerman (19) of the Hinner, et al., (17), and Beggs, et al., (18) procedures.

Transformants were then grown in shaker flasks and supernates assayed and shown to have IGF-1 activity by the radioimmune assay procedure of Furlanetto. et al., (23) as modified by Hintz, et al., (24).

One of these clones was grown in large scale in a 10-liter fermentor and IGF-1 purified from the supernatant of this fermentation. This material was then subjected to amino terminal protein sequencing and shown to be mature IGF-1 protein.

Human EGF is prepared in accordance with the invention following analogous procedures as those described above.

Construction, Expression, and Secretion of Human EGF.

In a fashion similar to IGF-1, double stranded DNA (FIG. 15; *SEQ ID NO. 50*) synthesized either by chemical means or through polymerization reactions was assembled to form a mature EGF coding sequence, with a codon coding for methionine (ATG) just preceding the amino-terminal asparagine found in the mature protein, and a codon (GTC) substituting valine for methionine at residue number 21 from the amino terminal asparagine. This construction was then attached at the 5' end to an additional coding sequence, which when expressed in yeast or bacteria produced a fusion protein. This fusion protein was then susceptible to CNBr cleavage at the methionine to release the valine substituted human EGF molecule.

To secrete the mature form of EGF from yeast, the above sequence coding for the mature protein was attached to the α-factor promoter/prepro sequence, the codon coding for valine at residue number 21 was replaced by ATG, and the appropriate deletion was made to bring the coding sequence for mature EGF adjacent to the α-factor signal coding sequence (FIG. 16; *SEQ ID NOS. 51–52*). This construction was then inserted into the yeast vector Yep9T and transformed into yeast. Transformants produced as such expressed and secreted mature human EGF. In addition, the sequence coding for mature EGF was attached to the preinvertase signal sequence (FIG. 17; *SEQ ID NOS. 53–54*) and this construction, when inserted into the yeast vector Yep1PT Small containing the PGK promoter, and transformed into yeast, resulted in the expression and secretion of human EGF.

Construction, Expression, and Secretion of Human IGF-II

A double stranded DNA sequence coding for mature IGF-II was constructed from a combination of synthetic and natural DNA sequences (FIG. 18; *SEQ ID NOS. 55–56*). This coding sequence, which did not contain an internal methionine, was attached to the TrpE leader protein coding sequence and was expressed as a fusion protein. Mature IGF-II was chemically cleaved from the purified fusion product by the action of CNBr upon a methionine residue preceding the first residue (alanine) of the mature protein.

The IGF-II coding sequence was also attached to the α-factor promoter/prepro sequence and after the appropriate deletion was made to bring the 3' end of the α-factor signal coding sequence adjacent to the 5' end of mature IGF-II coding sequence, the construction was inserted into the Yep9T vector and transformed into yeast. Resultant transformants expressed and secreted mature human IGF-II. In the same manner, the sequence coding for mature IGF-II was attached to the preinvertase coding sequence. The resultant construction was inserted into Yep1PT Small and transformed into yeast. Transformants produced as such expressed and secreted mature human IGF-II.

Pharmaceutical Compositions

The compounds of the present invention can be formulated according to known methods to prepare pharmaceutically useful compositions, whereby the human IGF and human EGF or products hereof are combined in admixture with a pharmaceutically acceptable carrier vehicle. Suitable vehicles and their formulation, inclusive of other human proteins, e.g. human serum albumin are described, for example, in Remington's Pharmaceutical Sciences by E. W. Martin, which is hereby incorporated by reference. Such compositions will contain an effective amount of the protein hereof together with a suitable amount of vehicle in order to prepare pharmaceutically acceptable compositions suitable for effective administration.

Notwithstanding that reference has been made to particular preferred embodiments of the present invention, it will be understood that the present invention is not to be construed as limited to such but rather to the lawful scope of the appended claims.

Bibliography

A. Rinderknecht, E. W. et al., Proceedings National Academy of Sciences (USA) 73, 2365 (1976).
B. Rinderknecht, et al., Proceedings National Academy of Sciences (USA) 73, 4379 (1976).
C. Blundell, et al., Proceedings National Academy of Sciences (USA) 75, 1980 (1978).
D. Rinderknecht, et al., Journal of Biological Chemistry 253, 2769 (1978), 2365 (1976).
E. Rinderknecht, et al., FEBS Letters 89, 283 (1978).
F. Zaph, et al., Metabolism 27, 1803 (1978).
G. Hintz, et al., Journal of Clinical Endocrinology and Metabolism 50, 405 (1980).
H. Blundell, et al., Nature 287, 781 (1980).
I. Hintz, et al., Journal of Clinical Endo. and Metabolism 51, 672 (1980).
J. Baxter, et al., Journal of Clinical Endo. and Metabolism 54, 464 (1980).
K. Hintz, et al., Journal of Clinical Endo, and Metabolism 54, 442 (1982).
L. Schoenie, et al., Nature 296, 252 (1982).
M. British Patent Application Publication No. 2007676A.
N. Wetzel, American Scientist 68, 664 (1980).
O. Microbiology, Second Edition, Harper and Row Publications Inc., Hagerstown, Md. (1973), especially pages 1122 et sequence.
P. Scientific American 245, 106 (1981).
1. Rinderknecht, E. and Humbel, R. E., J. Biol. Chem. 253, 8, 2769–2776 (1978).
2. Crea, R. and Horn, T., Nucleic Acids Research 8, 2331–2776 (1980).
3. Dagert, M. and Ehrlich, S. D., Gene 6, 23–28 (1979).
4. Birnboim, H. C. and Doly, J., Nucleic Acids Research 7, 1513–1523 (1979).
5. Maxam, A. and Gilbert, W. Methods in Enzymology 65, 499 (1980).
6. Villa-Komaroff et al., Proc. Natl. Acad. Sci. USA 75, 3727 (1979).
7. Rowenkamp and Firtel, Dicryostelium Dev. Biol. 79, 409 (1980).
8. Wunsch, E. et al., Hoppe-Seyler's Z. Physiol. Chem. Bd. 362, S1285–1287 (September 1981).
9. Maniatis, T. et al., Molecular Cloning, 426 (1982).
10. Kleid., D. G., New York Acad. of Sci., Annals. (in press)
11. Seifer, S. and Gallop, P. M. The Proteins, 2nd Ed. (H. Neurath, ed.) Vol. V. p. 659 (1966).
12. Nordwig, A., Leder 13, 10 (1962).
13. Lin, N. (U.S. Ser. No. 06/452,363, filed Dec. 22, 1982).
14. Laemmli, U. K. Nature (London) 227, 680–685 (1970).
15. Bolivar, F. et al., Gene 2, 95 (1977).
16. Chang, C. N. (U.S. Ser. No. 06/488337, filed Apr. 25, 1983 filed as a continuation U.S. Ser. No. 07/541,186 on Jun. 20, 1990, and issued as U.S. Pat. No. 5,010,003).

17. Hinnen, A. et al., Proc. Natl. Acad. Sci. USA 75, 1929–1933 (1978)
18. Beggs, J. D., Nature 275, 104–109 (1978).
19. Hitzeman, R. A. et al. U.S. Ser. No. 438236, filed Nov. 1, 1982
20. Capon, D. (refer to Bovine Interferon patent number) (1983).
21. Hitzeman, R. A. et al., Science 219, 620–625 (1983).
22. Singh, A. (U.S. Ser. No. 06/488323, filed Apr. 25, 1983).
23. Furlanetto, R. W., Underwood, L. E., Van Wyk, J. J., D'Ercole, A. J., J. Clin. Invest. 60, 648 (1977).
24. Hintz, R. L., Liu, F., Marshall, L. B., Chung, D., J. Clin. Endocrinol. Metab. 50, 405 (1980).
25. Hitzeman, R. A. et al., Proceedings of the Berkeley Workshop on Recent Advances in Yeast Molecular Biology: Recombinant DNA U.C. Press, Berkeley, p. 173 (1982).
26. Horner, J. M., Liu, F., Hintz, R. A., J. Clin. Endocrinol. Metab. 47, 6, p. 1287 (1978).
27. Rossi, J. J. Zierzek, R., Huang, T., Walker, P. A., Itakura, K., J. Biol. Chem. 257, 16, 9226 (1982).

SEQUENCE LISTING

```
<160> NUMBER OF SEQ ID NOS: 66

<210> SEQ ID NO 1
<211> LENGTH: 12
<212> TYPE: DNA
<213> ORGANISM: Artificial Sequence
<220> FEATURE:
<223> OTHER INFORMATION: Synthetic DNA

<400> SEQUENCE: 1

gatccagaat tc                                                          12


<210> SEQ ID NO 2
<211> LENGTH: 12
<212> TYPE: DNA
<213> ORGANISM: Artificial Sequence
<220> FEATURE:
<223> OTHER INFORMATION: Synthetic DNA

<400> SEQUENCE: 2

gatcgaattc tg                                                          12


<210> SEQ ID NO 3
<211> LENGTH: 12
<212> TYPE: DNA
<213> ORGANISM: Artificial Sequence
<220> FEATURE:
<223> OTHER INFORMATION: 5' ProAla DNA linker; synthetic DNA

<400> SEQUENCE: 3

aattccctgc cg                                                          12


<210> SEQ ID NO 4
<211> LENGTH: 11
<212> TYPE: DNA
<213> ORGANISM: Artificial Sequence
<220> FEATURE:
<223> OTHER INFORMATION: 3' ProAla DNA linker; synthetic DNA

<400> SEQUENCE: 4

gaccggcagg g                                                           11


<210> SEQ ID NO 5
<211> LENGTH: 12
<212> TYPE: DNA
<213> ORGANISM: Artificial Sequence
<220> FEATURE:
<223> OTHER INFORMATION: 5' SalI-EcoRI DNA linker; synthetic DNA

<400> SEQUENCE: 5

tcgacgtaca tg                                                          12
```

-continued

<210> SEQ ID NO 6
<211> LENGTH: 12
<212> TYPE: DNA
<213> ORGANISM: Artificial Sequence
<220> FEATURE:
<223> OTHER INFORMATION: 3' SalI-EcoRI DNA linker; synthetic DNA

<400> SEQUENCE: 6 aattcatgta cg 12

<210> SEQ ID NO 7
<211> LENGTH: 21
<212> TYPE: DNA
<213> ORGANISM: Artificial Sequence
<220> FEATURE:
<223> OTHER INFORMATION: 5' synthetic DNA; yeast invertase coding signal

<400> SEQUENCE: 7 agctttcctt ttccttttgg c 21

<210> SEQ ID NO 8
<211> LENGTH: 22
<212> TYPE: DNA
<213> ORGANISM: Artificial Sequence
<220> FEATURE:
<223> OTHER INFORMATION: 3' synthetic DNA; yeast invertase coding signal

<400> SEQUENCE: 8 aaccagccaa aaggaaaagg aa 22

<210> SEQ ID NO 9
<211> LENGTH: 26
<212> TYPE: DNA
<213> ORGANISM: Artificial Sequence
<220> FEATURE:
<223> OTHER INFORMATION: 5' synthetic DNA; yeast invertase coding signal

<400> SEQUENCE: 9 tggttttgca gccaaaatat ctgcag 26

<210> SEQ ID NO 10
<211> LENGTH: 24
<212> TYPE: DNA
<213> ORGANISM: Artificial Sequence
<220> FEATURE:
<223> OTHER INFORMATION: 3' synthetic DNA; yeast invertase coding signal

<400> SEQUENCE: 10 gacctgcaga tattttggct gcaa 24

<210> SEQ ID NO 11
<211> LENGTH: 28
<212> TYPE: DNA
<213> ORGANISM: Artificial Sequence
<220> FEATURE:
<223> OTHER INFORMATION: Synthetic DNA

<400> SEQUENCE: 11 agagtttccg gacctctttt atccaaag 28

<210> SEQ ID NO 12
<211> LENGTH: 27
<212> TYPE: DNA
<213> ORGANISM: Artificial Sequence
<220> FEATURE:
<223> OTHER INFORMATION: 5' Synthetic DNA; isolated replicative form -continued

<400> SEQUENCE: 12 gaggctgaag ctctagaatt ccctgcc 27

<210> SEQ ID NO 13
<211> LENGTH: 27
<212> TYPE: DNA
<213> ORGANISM: Artificial Sequence
<220> FEATURE:
<223> OTHER INFORMATION: 3' Synthetic DNA; isolated replicative form

<400> SEQUENCE: 13 ggcagggaat tctagagctt cagcctc 27

<210> SEQ ID NO 14
<211> LENGTH: 43
<212> TYPE: DNA
<213> ORGANISM: Artificial Sequence
<220> FEATURE:
<223> OTHER INFORMATION: DNA IGF-1 Left Half: 1L (43-mer); Synthetic DNA

<400> SEQUENCE: 14 agttctgatt tcgaattcta tgggtccgga aactctgtgc ggc 43

<210> SEQ ID NO 15
<211> LENGTH: 43
<212> TYPE: DNA
<213> ORGANISM: Artificial Sequence
<220> FEATURE:
<223> OTHER INFORMATION: DNA IGF-1 Left Half: 3L (43-mer); Synthetic DNA

<400> SEQUENCE: 15 agttctgatt ctgcagagcg tcaaccagct cagcgccgca cag 43

<210> SEQ ID NO 16
<211> LENGTH: 46
<212> TYPE: DNA
<213> ORGANISM: Artificial Sequence
<220> FEATURE:
<223> OTHER INFORMATION: DNA IGF-1 Left Half: 2L (46-mer); Synthetic DNA

<400> SEQUENCE: 16 agttctgatt ctgcagttcg tatgtggtga tcgaggcttc tacttc 46

<210> SEQ ID NO 17
<211> LENGTH: 46
<212> TYPE: DNA
<213> ORGANISM: Artificial Sequence
<220> FEATURE:
<223> OTHER INFORMATION: DNA IGF-1 Left Half: 4L (46-mer); Synthetic DNA

<400> SEQUENCE: 17 agttctgatt gaggatccgt acccagtcgg tttgttgaag tagaag 46

<210> SEQ ID NO 18
<211> LENGTH: 46
<212> TYPE: DNA
<213> ORGANISM: Artificial Sequence
<220> FEATURE:
<223> OTHER INFORMATION: DNA IGF-1 Right Half: 1R (46-mer); Synthetic
DNA

<400> SEQUENCE: 18 gactgacttc tggatcctcc tctcgtcgtg ctccgcaaac cggcat 46

-continued

<210> SEQ ID NO 19
<211> LENGTH: 46
<212> TYPE: DNA
<213> ORGANISM: Artificial Sequence
<220> FEATURE:
<223> OTHER INFORMATION: DNA IGF-1 Right Half: 3R (46-mer); Synthetic
DNA

<400> SEQUENCE: 19 gactgactta caggaccgaa aacagcattc atcaacgatg ccggtt 46

<210> SEQ ID NO 20
<211> LENGTH: 54
<212> TYPE: DNA
<213> ORGANISM: Artificial Sequence
<220> FEATURE:
<223> OTHER INFORMATION: DNA IGF-1 Right Half: 2R (54-mer); Synthetic
DNA

<400> SEQUENCE: 20 tgactgactt ggtcctgtga ccttcgccgt ctggaaatgt actgcgctcc gctg 54

<210> SEQ ID NO 21
<211> LENGTH: 46
<212> TYPE: DNA
<213> ORGANISM: Artificial Sequence
<220> FEATURE:
<223> OTHER INFORMATION: DNA IGF-1 Right Half: 4R (46-mer); Synthetic
DNA

<400> SEQUENCE: 21 gactgacttg agtcgactat gcagacttag ccggtttcag cggagc 46

<210> SEQ ID NO 22
<211> LENGTH: 15
<212> TYPE: PRT
<213> ORGANISM: Artificial Sequence
<220> FEATURE:
<223> OTHER INFORMATION: Protein IGF-1 Left Half: Part 1; Synthetic
Protein

<400> SEQUENCE: 22

Gly Pro Glu Thr Leu Cys Gly Ala Glu Leu Val Asp Ala Leu Gln
1 5 10 15

<210> SEQ ID NO 23
<211> LENGTH: 77
<212> TYPE: DNA
<213> ORGANISM: Artificial Sequence
<220> FEATURE:
<223> OTHER INFORMATION: DNA IGF-1 Left Half: Part 1; Synthetic DNA

<400> SEQUENCE: 23 agttctgatt tcgaattcta tgggtccgga aactctgtgc ggcgctgagc tggttgacgc 60 tctgcagaat cagaact 77

<210> SEQ ID NO 24
<211> LENGTH: 18
<212> TYPE: PRT
<213> ORGANISM: Artificial Sequence
<220> FEATURE:
<223> OTHER INFORMATION: Protein IGF-1 Left Half: Part 2; Synthetic
Protein

<400> SEQUENCE: 24

Gln Phe Val Cys Gly Asp Arg Gly Phe Tyr Phe Asn Lys Pro Thr Gly
1 5 10 15

Tyr Gly

<210> SEQ ID NO 25
<211> LENGTH: 82
<212> TYPE: DNA
<213> ORGANISM: Artificial Sequence
<220> FEATURE:
<223> OTHER INFORMATION: DNA IGF-1 Left Half: Part 2; Synthetic DNA

<400> SEQUENCE: 25 agttctgatt ctgcagttcg tatgtggtga tcgaggcttc tacttcaaca aaccgactgg 60 gtacggatcc tcaatcagaa ct 82

<210> SEQ ID NO 26
<211> LENGTH: 19
<212> TYPE: PRT
<213> ORGANISM: Artificial Sequence
<220> FEATURE:
<223> OTHER INFORMATION: Protein IGF-1 Right Half: Part 3; Synthetic
Protein

<400> SEQUENCE: 26

Ser Ser Ser Arg Arg Ala Pro Gln Thr Gly Ile Val Asp Glu Cys Cys
1 5 10 15

Phe Arg Ser

<210> SEQ ID NO 27
<211> LENGTH: 83
<212> TYPE: DNA
<213> ORGANISM: Artificial Sequence
<220> FEATURE:
<223> OTHER INFORMATION: DNA IGF-1 Right Half: Part 3; Synthetic DNA

<400> SEQUENCE: 27 gactgacttc tggatcctcc tctcgtcgtg ctccgcaaac cggcatcgtt gatgaatgct 60 gttttcggtc ctgtaagtca gtc 83

<210> SEQ ID NO 28
<211> LENGTH: 20
<212> TYPE: PRT
<213> ORGANISM: Artificial Sequence
<220> FEATURE:
<223> OTHER INFORMATION: Protein IGF-1 Right Half: Part 4; Synthetic
Protein

<400> SEQUENCE: 28

Ser Cys Asp Leu Arg Arg Leu Glu Met Tyr Cys Ala Pro Leu Lys Pro
1 5 10 15

Ala Lys Ser Ala
20

<210> SEQ ID NO 29
<211> LENGTH: 91
<212> TYPE: DNA
<213> ORGANISM: Artificial Sequence
<220> FEATURE:
<223> OTHER INFORMATION: DNA IGF-1 Right Half: Part 4; Synthetic DNA

<400> SEQUENCE: 29 tgactgactt ggtcctgtga ccttcgccgt ctggaaatgt actgcgctcc gctgaaaccg 60 gctaagtctg catagtcgac tcaagtcagt c 91

-continued

<210> SEQ ID NO 30
<211> LENGTH: 15
<212> TYPE: PRT
<213> ORGANISM: Artificial Sequence
<220> FEATURE:
<223> OTHER INFORMATION: Protein IGF-1 Left Half: Part 1; Synthetic
Protein

<400> SEQUENCE: 30

Gly Pro Glu Thr Leu Cys Gly Ala Glu Leu Val Asp Ala Leu Gln
1 5 10 15

<210> SEQ ID NO 31
<211> LENGTH: 54
<212> TYPE: DNA
<213> ORGANISM: Artificial Sequence
<220> FEATURE:
<223> OTHER INFORMATION: DNA IGF-1 Left Half: Part 1; 1L; Synthetic DNA

<400> SEQUENCE: 31 aattctatgg gtccggaaac tctgtgcggc gctgagctgg ttgacgctct gcag 54

<210> SEQ ID NO 32
<211> LENGTH: 46
<212> TYPE: DNA
<213> ORGANISM: Artificial Sequence
<220> FEATURE:
<223> OTHER INFORMATION: DNA IGF-1 Left Half: Part 1; 3L; Synthetic DNA

<400> SEQUENCE: 32 gatacccagg cctttgagac acgccgcgac tcgaccaact gcgaga 46

<210> SEQ ID NO 33
<211> LENGTH: 16
<212> TYPE: PRT
<213> ORGANISM: Artificial Sequence
<220> FEATURE:
<223> OTHER INFORMATION: Protein IGF-1 Left Half: Part 2; Synthetic
Protein

<400> SEQUENCE: 33

Phe Val Cys Gly Asp Arg Gly Phe Tyr Phe Asn Lys Pro Thr Gly Tyr
1 5 10 15

<210> SEQ ID NO 34
<211> LENGTH: 48
<212> TYPE: DNA
<213> ORGANISM: Artificial Sequence
<220> FEATURE:
<223> OTHER INFORMATION: DNA IGF-1 Left Half: Part 2; 2L; Synthetic DNA

<400> SEQUENCE: 34 ttcgtatgtg gtgatcgagg cttctacttc aacaaaccga ctgggtac 48

<210> SEQ ID NO 35
<211> LENGTH: 57
<212> TYPE: DNA
<213> ORGANISM: Artificial Sequence
<220> FEATURE:
<223> OTHER INFORMATION: DNA IGF-1 Left Half: Part 2; 4L; Synthetic DNA

<400> SEQUENCE: 35 cgtcaagcat acaccactag ctccgaagat gaagttgttt ggctgaccca tgcctag 57

<210> SEQ ID NO 36
<211> LENGTH: 19
<212> TYPE: PRT

-continued

<213> ORGANISM: Artificial Sequence
<220> FEATURE:
<223> OTHER INFORMATION: Protein IGF-1 Right Half: Part 3; Synthetic
Protein

<400> SEQUENCE: 36

Ser Ser Ser Arg Arg Ala Pro Gln Thr Gly Ile Val Asp Glu Cys Cys
1 5 10 15

Phe Arg Ser

<210> SEQ ID NO 37
<211> LENGTH: 99
<212> TYPE: DNA
<213> ORGANISM: Artificial Sequence
<220> FEATURE:
<223> OTHER INFORMATION: DNA IGF-1 Right Half: Part 3; Synthetic DNA

<400> SEQUENCE: 37 gactgacttc tggatcctcc tctcgtcgtg ctccgcaaac cggcatcgtt gatgaatgct 60 gttttcggtc ctgtaagtca gtcccccccc cccccccc 99

<210> SEQ ID NO 38
<211> LENGTH: 98
<212> TYPE: DNA
<213> ORGANISM: Artificial Sequence
<220> FEATURE:
<223> OTHER INFORMATION: DNA IGF-1 Right Half: Part 3; Synthetic DNA

<400> SEQUENCE: 38 cccccccccc ccccccctgac tgaagaccta ggaggagagc agcacgaggc gtttggccgt 60 agcaactact tacgacaaaa gccaggacat tcagtcag 98

<210> SEQ ID NO 39
<211> LENGTH: 21
<212> TYPE: PRT
<213> ORGANISM: Artificial Sequence
<220> FEATURE:
<223> OTHER INFORMATION: Protein IGF-1 Right Half: Part 4; Synthetic
Protein

<400> SEQUENCE: 39

Ser Cys Asp Leu Arg Arg Leu Glu Met Tyr Cys Ala Pro Leu Lys Pro
1 5 10 15

Ala Lys Ser Ala Thr
20

<210> SEQ ID NO 40
<211> LENGTH: 107
<212> TYPE: DNA
<213> ORGANISM: Artificial Sequence
<220> FEATURE:
<223> OTHER INFORMATION: DNA IGF-1 Right Half: Part 4; Synthetic DNA

<400> SEQUENCE: 40 tgactgactt ggtcctgtga ccttcgccgt ctggaaatgt actgcgctcc gctgaaaccg 60 gctaagtctg catagtcgac tcaagtcagt ccccccccc cccccc 107

<210> SEQ ID NO 41
<211> LENGTH: 106
<212> TYPE: DNA
<213> ORGANISM: Artificial Sequence
<220> FEATURE:
<223> OTHER INFORMATION: DNA IGF-1 Right Half: Part 4; Synthetic DNA -continued

<400> SEQUENCE: 41 cccccccccc cccccactga ctgaaccagg acactggaag cggcagacct ttacatgacg 60 cgaggcgact ttggccgatt cagacgtatc agctgagttc agtcag 106

<210> SEQ ID NO 42
<211> LENGTH: 262
<212> TYPE: PRT
<213> ORGANISM: Artificial Sequence
<220> FEATURE:
<223> OTHER INFORMATION: Deduced fusion protein containing IGF-1;
synthetic protein

<400> SEQUENCE: 42

Met Lys Ala Ile Phe Val Leu Lys Gly Ser Leu Asp Arg Asp Leu Asp
1 5 10 15

Ser Arg Ile Glu Leu Glu Met Arg Thr Asp His Lys Glu Leu Ser Glu
20 25 30

His Leu Met Leu Val Asp Leu Ala Arg Asn Asp Leu Ala Arg Ile Cys
35 40 45

Thr Pro Gly Ser Arg Tyr Val Ala Asp Leu Thr Lys Val Asp Arg Tyr
50 55 60

Ser Tyr Val Met His Leu Val Ser Arg Val Val Gly Glu Leu Arg His
65 70 75 80

Asp Leu Asp Ala Leu His Ala Tyr Arg Ala Cys Met Asn Met Gly Thr
85 90 95

Leu Ser Gly Ala Pro Lys Val Arg Ala Met Gln Leu Ile Ala Glu Ala
100 105 110

Glu Gly Arg Arg Arg Gly Ser Tyr Gly Gly Ala Val Gly Tyr Phe Thr
115 120 125

Ala His Gly Asp Leu Asp Thr Cys Ile Val Ile Arg Ser Ala Leu Val
130 135 140

Glu Asn Gly Ile Ala Thr Val Gln Ala Gly Ala Gly Val Val Leu Asp
145 150 155 160

Ser Val Pro Gln Ser Glu Ala Asp Glu Thr Arg Asn Lys Ala Arg Ala
165 170 175

Val Leu Arg Ala Ile Ala Thr Ala His His Ala Gln Glu Phe Pro Ala
180 185 190

Gly Pro Glu Thr Leu Cys Gly Ala Glu Leu Val Asp Ala Leu Gln Phe
195 200 205

Val Cys Gly Asp Arg Gly Phe Tyr Phe Asn Lys Pro Thr Gly Tyr Gly
210 215 220

Ser Ser Ser Arg Arg Ala Pro Gln Thr Gly Ile Val Asp Glu Cys Cys
225 230 235 240

Phe Arg Ser Cys Asp Leu Arg Arg Leu Glu Met Tyr Cys Ala Pro Leu
245 250 255

Lys Pro Ala Lys Ser Ala
260

<210> SEQ ID NO 43
<211> LENGTH: 803
<212> TYPE: DNA
<213> ORGANISM: Artificial Sequence
<220> FEATURE:
<223> OTHER INFORMATION: Synthetic DNA

<400> SEQUENCE: 43 atgaaagcaa ttttcgtact gaaaggttca ctggacagag atctcgacag ccgtattgaa 60

-continued

```
ctggaaatgc gtaccgatca taaagagctg tctgaacatc tgatgctggt tgatctcgcc    120

cgtaatgatc tggcacgcat ttgcaccccc ggcagccgct acgtcgccga tctcaccaaa    180

gttgaccgtt attcctatgt gatgcacctc gtctctcgcg tagtcggcga actgcgtcac    240

gatcttgacg ccctgcacgc ttatcgcgcc tgtatgaata tggggacgtt aagcggtgcg    300

ccgaaagtac gcgctatgca gttaattgcc gaggcggaag gtcgtcgccg cggcagctac    360

ggcggcgcgg taggttattt caccgcgcat ggcgatctcg acacctgcat tgtgatccgc    420

tcggcgctgg tggaaaacgg tatcgccacc gtgcaagcgg gtgctggtgt agtccttgat    480

tctgttccgc agtcggaagc cgacgaaacc cgtaacaaag cccgcgctgt actgcgcgct    540

attgccaccg cgcatcatgc acaggaattc cctgccggtc cggaaactct gtgcggcgct    600

gagctggttg acgctctgca gttcgtatgt ggtgatcgag gcttctactt caacaaaccg    660

actgggtacg gatcctcctc tcgtcgtgct ccgcaaaccg gcatcgttga tgaatgctgt    720

tttcggtcct gtgaccttcg ccgtctggaa atgtactgcg ctccgctgaa accggctaag    780

tctgcatagt cgacgtacat gaa                                            803
```

<210> SEQ ID NO 44
<211> LENGTH: 89
<212> TYPE: PRT
<213> ORGANISM: Artificial Sequence
<220> FEATURE:
<223> OTHER INFORMATION: sLE-IGF-1 Fusion Protein; synthetic Protein

<400> SEQUENCE: 44

```
Met Lys Ala Ile Phe Val Leu Lys Gly Ser Leu Asp Arg Asp Pro Glu
 1               5                  10                  15

Phe Pro Ala Gly Pro Glu Thr Leu Cys Gly Ala Glu Leu Val Asp Ala
            20                  25                  30

Leu Gln Phe Val Cys Gly Asp Arg Gly Phe Tyr Phe Asn Lys Pro Thr
        35                  40                  45

Gly Tyr Gly Ser Ser Ser Arg Arg Ala Pro Gln Thr Gly Ile Val Asp
    50                  55                  60

Glu Cys Cys Phe Arg Ser Cys Asp Leu Arg Arg Leu Glu Met Tyr Cys
65                  70                  75                  80

Ala Pro Leu Lys Pro Ala Lys Ser Ala
                85
```

<210> SEQ ID NO 45
<211> LENGTH: 270
<212> TYPE: DNA
<213> ORGANISM: Artificial Sequence
<220> FEATURE:
<223> OTHER INFORMATION: Synthetic DNA

<400> SEQUENCE: 45

```
atgaaagcaa ttttcgtact gaaaggttca ctggacagag atccagaatt ccctgccggt     60

ccggaaactc tgtgcggcgc tgagctggtt gacgctctgc agttcgtatg tggtgatcga    120

ggcttctact tcaacaaacc gactgggtac ggatcctcct ctcgtcgtgc tccgcaaacc    180

ggcatcgttg atgaatgctg ttttcggtcc tgtgaccttc gccgtctgga aatgtactgc    240

gctccgctga aaccggctaa gtctgcatag                                     270
```

<210> SEQ ID NO 46
<211> LENGTH: 164
<212> TYPE: PRT

-continued

<213> ORGANISM: Artificial Sequence
<220> FEATURE:
<223> OTHER INFORMATION: IGF-1 Protein fused with alpha factor pre-pro
sequence; synthetic protein

<400> SEQUENCE: 46

Met Arg Phe Pro Ser Ile Phe Ser Ala Val Leu Phe Ala Ala Ser Ser
1 5 10 15

Ala Leu Ala Ala Pro Val Asn Thr Thr Thr Glu Asp Glu Thr Ala Gln
20 25 30

Ile Pro Ala Glu Ala Val Ile Gly Tyr Ser Asp Leu Glu Gly Asp Phe
35 40 45

Asp Val Ala Val Leu Pro Phe Ser Asn Ser Thr Asn Asn Gly Leu Leu
50 55 60

Phe Ile Asn Thr Thr Ile Ala Ser Ile Ala Ala Lys Glu Glu Gly Val
65 70 75 80

Ser Leu Asp Lys Arg Glu Ala Glu Ala Leu Glu Phe Pro Ala Gly Pro
85 90 95

Glu Thr Leu Cys Gly Ala Glu Leu Val Asp Ala Leu Glu Phe Val Cys
100 105 110

Gly Asp Arg Gly Phe Tyr Phe Asn Lys Pro Thr Gly Tyr Gly Ser Ser
115 120 125

Ser Arg Arg Ala Pro Gln Thr Gly Ile Val Asp Glu Cys Cys Phe Arg
130 135 140

Ser Cys Asp Leu Arg Arg Leu Glu Met Tyr Cys Ala Pro Leu Lys Pro
145 150 155 160

Ala Lys Ser Ala

<210> SEQ ID NO 47
<211> LENGTH: 495
<212> TYPE: DNA
<213> ORGANISM: Artificial Sequence
<220> FEATURE:
<223> OTHER INFORMATION: Synthetic DNA

<400> SEQUENCE: 47 atgagatttc cttcaatttt tagtgcagtt ttattcgcag catcctccgc attagctgct 60 ccagtcaaca ctacaacaga agatgaaacg gcacaaattc cggctgaagc tgtcatcggt 120 tactcagatt tagaagggga tttcgatgtt gctgttttgc cattttccaa cagcacaaat 180 aacgggttat tgtttataaa tactactatt gccagcattg ctgctaaaga agaaggggta 240 tctttggata aaagagaggc tgaagctcta gaattccctg ccggtccgga aactctgtgc 300 ggtgctgaac tggttgacgc tctggagttc gtatgtggtg accgtggctt ttacttcaac 360 aaaccgactg gttacggatc ctcctctcgt cgcgctccgc aaactggcat cgttgatgaa 420 tgctgttttc gttcttgtga cctgcgccgt ctggaaatgt actgcgctcc gctgaaaccg 480 gctaagtctg catag 495

<210> SEQ ID NO 48
<211> LENGTH: 89
<212> TYPE: PRT
<213> ORGANISM: Artificial Sequence
<220> FEATURE:
<223> OTHER INFORMATION: Yeast invertase signal IGF-1 fusion protein

<400> SEQUENCE: 48

Met Leu Leu Gln Ala Phe Leu Phe Leu Leu Ala Gly Phe Ala Ala Lys
1 5 10 15

-continued

```
Ile Ser Ala Gly Pro Glu Thr Leu Cys Gly Ala Glu Leu Val Asp Ala
            20                  25                  30

Leu Gln Phe Val Cys Gly Asp Arg Gly Phe Tyr Phe Asn Lys Pro Thr
        35                  40                  45

Gly Tyr Gly Ser Ser Ser Arg Arg Ala Pro Gln Thr Gly Ile Val Asp
    50                  55                  60

Glu Cys Cys Phe Arg Ser Cys Asp Leu Arg Arg Leu Glu Met Tyr Cys
65                  70                  75                  80

Ala Pro Leu Lys Pro Ala Lys Ser Ala
                85


<210> SEQ ID NO 49
<211> LENGTH: 270
<212> TYPE: DNA
<213> ORGANISM: Artificial Sequence
<220> FEATURE:
<223> OTHER INFORMATION: Synthetic DNA

<400> SEQUENCE: 49

atgcttttgc aagctttcct tttccttttg gctggttttg cagccaaaat atctgcaggt     60

ccggaaactc tgtgcggcgc tgagctggtt gacgctctgc agttcgtatg tggtgatcga    120

ggcttctact tcaacaaacc gactgggtac ggatcctcct ctcgtcgtgc tccgcaaacc    180

ggcatcgttg atgaatgctg ttttcggtcc tgtgaccttc gccgtctgga aatgtactgc    240

gctccgctga aaccggctaa gtctgcatag                                     270


<210> SEQ ID NO 50
<211> LENGTH: 201
<212> TYPE: DNA
<213> ORGANISM: Artificial Sequence
<220> FEATURE:
<223> OTHER INFORMATION: Synthetic DNA; mature EGF coding sequence

<400> SEQUENCE: 50

gaattcatga actctgactc tgaatgtcca ttatcgcatg atgggtactg tttgcacgac     60

ggagtctgta tgtatattga agctctagac aagtacgctt gtaactgtgt tgttggttac    120

atcggtgaaa gatgtcaata cagagatcta aagtggtggg aattgagata gattgaattg    180

aattgaaatc gattaaagct t                                              201


<210> SEQ ID NO 51
<211> LENGTH: 138
<212> TYPE: PRT
<213> ORGANISM: Artificial Sequence
<220> FEATURE:
<223> OTHER INFORMATION: Yeast alpha factor protein “pre-pro” sequence
      fused with EGF

<400> SEQUENCE: 51

Met Arg Phe Pro Ser Ile Phe Ser Ala Val Leu Phe Ala Ala Ser Ser
 1               5                  10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80
```

```
Ser Leu Asp Lys Arg Asn Ser Asp Ser Glu Cys Pro Leu Ser His Asp
                85                  90                  95

Gly Tyr Cys Leu His Asp Gly Val Cys Met Tyr Ile Glu Ala Leu Asp
            100                 105                 110

Lys Tyr Ala Cys Asn Cys Val Val Gly Tyr Ile Gly Glu Arg Cys Gln
        115                 120                 125

Tyr Arg Asp Leu Lys Trp Trp Glu Leu Arg
    130                 135


<210> SEQ ID NO 52
<211> LENGTH: 417
<212> TYPE: DNA
<213> ORGANISM: Artificial Sequence
<220> FEATURE:
<223> OTHER INFORMATION: EGF DNA fused with yeast alpha factor "pre-pro"
      sequence

<400> SEQUENCE: 52

atgagatttc cttcaatttt tagtgcagtt ttattcgcag catcctccgc attagctgct     60

ccagtcaaca ctacaacaga agatgaaacg gcacaaattc cggctgaagc tgtcatcggt    120

tactcagatt tagaagggga tttcgatgtt gctgttttgc cattttccaa cagcacaaat    180

aacgggttat tgtttataaa tactactatt gccagcattg ctgctaaaga agaaggggta    240

tctttggata aaagaaactc tgactctgaa tgtccattat cgcatgatgg gtactgtttg    300

cacgacggag tctgtatgta tattgaagct ctagacaagt acgcttgtaa ctgtgttgtt    360

ggttacatcg gtgaaagatg tcaatacaga gatctaaagt ggtgggaatt gagatag       417


<210> SEQ ID NO 53
<211> LENGTH: 72
<212> TYPE: PRT
<213> ORGANISM: Artificial Sequence
<220> FEATURE:
<223> OTHER INFORMATION: Yeast invertase signal protein sequence fused
      with EGF

<400> SEQUENCE: 53

Met Leu Leu Gln Ala Phe Leu Phe Leu Leu Ala Gly Phe Ala Ala Lys
 1               5                  10                  15

Ile Ser Ala Asn Ser Asp Ser Glu Cys Pro Leu Ser His Asp Gly Tyr
            20                  25                  30

Cys Leu His Asp Gly Val Cys Met Tyr Ile Glu Ala Leu Asp Lys Tyr
        35                  40                  45

Ala Cys Asn Cys Val Val Gly Tyr Ile Gly Glu Arg Cys Gln Tyr Arg
    50                  55                  60

Asp Leu Lys Trp Trp Glu Leu Arg
65                  70


<210> SEQ ID NO 54
<211> LENGTH: 258
<212> TYPE: DNA
<213> ORGANISM: Artificial Sequence
<220> FEATURE:
<223> OTHER INFORMATION: EGF DNA fused with invertase sequence

<400> SEQUENCE: 54

gaattcatga tgttgttgca agctttcttg ttcttgttgg ctggtttcgc tgctaagatc     60

tctgctaact ctgactctga atgtccatta tcgcatgatg ggtactgttt gcacgacgga    120

gtctgtatgt acattgaagc tctagacaag tacgcttgta actgtgttgt tggttacatc    180
```

-continued

```
ggtgaaagat gtcaatacag agatctaaag tggtgggaat tgagatagat tgaattgaat    240

tgaaatcgat taaagctt                                                  258


<210> SEQ ID NO 55
<211> LENGTH: 68
<212> TYPE: PRT
<213> ORGANISM: Artificial Sequence
<220> FEATURE:
<223> OTHER INFORMATION: Protein coding sequence for Human IGF-II

<400> SEQUENCE: 55

Met Ala Tyr Arg Pro Ser Glu Thr Leu Cys Gly Gly Glu Leu Val Asp
 1               5                  10                  15

Thr Leu Gln Phe Val Cys Gly Asp Arg Gly Phe Tyr Phe Ser Arg Pro
            20                  25                  30

Ala Ser Arg Val Ser Arg Arg Ser Arg Gly Ile Val Glu Glu Cys Cys
        35                  40                  45

Phe Arg Ser Cys Asp Leu Ala Leu Leu Glu Thr Tyr Cys Ala Thr Pro
    50                  55                  60

Ala Lys Ser Glu
65


<210> SEQ ID NO 56
<211> LENGTH: 221
<212> TYPE: DNA
<213> ORGANISM: Artificial Sequence
<220> FEATURE:
<223> OTHER INFORMATION: DNA coding sequence for Human IGF-II

<400> SEQUENCE: 56

tctagaatta tggcttatcg accatctgaa accttgtgtg gtggtgagct ggtggacacc     60

ctccagttcg tctgtgggga ccgcggtttc tacttctcta ggcccgcaag ccgtgtgagc    120

cgtcgcagtc gtggcatcgt tgaggagtgc tgtttccgca gctgtgacct ggccctattg    180

gaaacctact gtgctacccc agctaagtct gaataggatc c                        221


<210> SEQ ID NO 57
<211> LENGTH: 5
<212> TYPE: PRT
<213> ORGANISM: Artificial Sequence
<220> FEATURE:
<223> OTHER INFORMATION: Protein carboxy terminus of alpha factor

<400> SEQUENCE: 57

Gly Gln Pro Met Tyr
 1               5


<210> SEQ ID NO 58
<211> LENGTH: 15
<212> TYPE: DNA
<213> ORGANISM: Artificial Sequence
<220> FEATURE:
<221> NAME/KEY: misc_feature
<222> LOCATION: 3
<223> OTHER INFORMATION: U= T or C
<221> NAME/KEY: misc_feature
<222> LOCATION: 9
<223> OTHER INFORMATION: U= A or T
<220> FEATURE:
<223> OTHER INFORMATION: DNA consensus oligonucleotides encoding
      alpha-factor carboxy terminus

<400> SEQUENCE: 58
```

-continued ggucaaccua tgtac 15

<210> SEQ ID NO 59
<211> LENGTH: 15
<212> TYPE: DNA
<213> ORGANISM: Artificial Sequence
<220> FEATURE:
<221> NAME/KEY: misc_feature
<222> LOCATION: 13
<223> OTHER INFORMATION: U= A or G
<220> FEATURE:
<223> OTHER INFORMATION: Synthetic DNA oligonucleotides pool I;
complementary to SEQ ID NO:58

<400> SEQUENCE: 59 gtacattggt tgucc 15

<210> SEQ ID NO 60
<211> LENGTH: 15
<212> TYPE: DNA
<213> ORGANISM: Artificial Sequence
<220> FEATURE:
<221> NAME/KEY: misc_feature
<222> LOCATION: 13
<223> OTHER INFORMATION: U= A or G
<220> FEATURE:
<223> OTHER INFORMATION: Synthetic DNA oligonucleotides pool II;
complementary to SEQ ID NO:58

<400> SEQUENCE: 60 gtacataggt tgucc 15

<210> SEQ ID NO 61
<211> LENGTH: 550
<212> TYPE: DNA
<213> ORGANISM: Artificial Sequence
<220> FEATURE:
<223> OTHER INFORMATION: DNA sequence of alpha factor

<400> SEQUENCE: 61 cgacagtaaa ttttgccgaa tttaatagct tctactgaaa aacagtggac catgtgaaaa 60 gatgcatctc atttatcaaa cacataatat tcaagtgagc cttacttcaa ttgtattgaa 120 gtgcaagaaa accaaaaagc aacaacaggt tttggataag tacatatata agagggcctt 180 ttgttcccat caaaaatgtt actgttctta cgattcattt acgattcaag aatagttcaa 240 acaagaagat tacaaactat caatttcata cacaatataa acgattaaaa gaatgagatt 300 tccttcaatt tttactgcag ttttattcgc agcatcctcc gcattagctg ctccagtcaa 360 cactacaaca gaagatgaaa cggcacaaat tccggctgaa gctgtcatcg gttacttaga 420 tttagaaggg gatttcgatg ttgctgtttt gccattttcc aacagcacaa ataacgggtt 480 attgtttata aatactacta ttgccagcat tgctgctaaa gaagaagggg tatctttgga 540 taaaagagag 550

<210> SEQ ID NO 62
<211> LENGTH: 80
<212> TYPE: PRT
<213> ORGANISM: Artificial Sequence
<220> FEATURE:
<223> OTHER INFORMATION: Protein sequence of alpha factor

<400> SEQUENCE: 62

Phe Thr Ala Val Leu Phe Ala Ala Ser Ser Ala Leu Ala Ala Pro Val
1 5 10 15

-continued

```
Asn Thr Thr Thr Glu Asp Glu Thr Ala Gln Ile Pro Ala Glu Ala Val
            20                  25                  30

Ile Gly Tyr Leu Asp Leu Glu Gly Asp Phe Asp Val Ala Val Leu Pro
        35                  40                  45

Phe Ser Asn Ser Thr Asn Asn Gly Leu Leu Phe Ile Asn Thr Thr Ile
    50                  55                  60

Ala Ser Ile Ala Ala Lys Glu Glu Gly Val Ser Leu Asp Lys Arg Glu
65                  70                  75                  80


<210> SEQ ID NO 63
<211> LENGTH: 79
<212> TYPE: PRT
<213> ORGANISM: Artificial Sequence
<220> FEATURE:
<223> OTHER INFORMATION: Protein sequence of alpha factor

<400> SEQUENCE: 63

Ala Glu Ala Trp His Trp Leu Gln Leu Lys Pro Gly Gln Pro Met Tyr
 1               5                  10                  15

Lys Arg Glu Ala Glu Ala Glu Ala Trp His Trp Leu Gln Leu Lys Pro
            20                  25                  30

Gly Gln Pro Met Tyr Lys Arg Glu Ala Asp Ala Glu Ala Trp His Trp
        35                  40                  45

Leu Gln Leu Lys Pro Gly Gln Pro Met Tyr Lys Arg Glu Ala Asp Ala
    50                  55                  60

Glu Ala Trp His Trp Leu Gln Leu Lys Pro Gly Gln Pro Met Tyr
65                  70                  75


<210> SEQ ID NO 64
<211> LENGTH: 552
<212> TYPE: DNA
<213> ORGANISM: Artificial Sequence
<220> FEATURE:
<223> OTHER INFORMATION: DNA sequence of alpha factor

<400> SEQUENCE: 64

gctgaagctt ggcattggtt gcaactaaaa cctggccaac caatgtacaa gagagaagcc     60

gaagctgaag cttggcattg gctgcaacta aagcctggcc aaccaatgta caaaagagaa    120

gccgacgctg aagcttggca ttggctgcaa ctaaagcctg gccaaccaat gtacaaaaga    180

gaagccgacg ctgaagcttg gcattggttg cagttaaaac ccggccaacc aatgtactaa    240

gcccgactga taacaacagt gtagatgtaa caaagtcgac tttgttccca ctgtactttt    300

agctcgtaca aaatacaata tacttttcat ttctccgtaa acaacatgtt ttcccatgta    360

atatcctttt ctatttttcg ttccgttacc aactttacac atactttata tagctattca    420

cttctataca ctaaaaaact aagacaattt taattttgct gcctgccata tttcaatttg    480

ttataaattc ctataattta tcctattagt agctaaaaaa agatgaatgt gaatcgaatc    540

ctaagagaat tc                                                        552


<210> SEQ ID NO 65
<211> LENGTH: 967
<212> TYPE: DNA
<213> ORGANISM: Artificial Sequence
<220> FEATURE:
<223> OTHER INFORMATION: DNA sequence of alpha factor

<400> SEQUENCE: 65

ttcttcattg gtacatcaat gccagcaacg atgtgcgcat ctgggcgacg cctgtagtga     60
```

-continued

```
ttgttttcaa ggtatcgagc caaactattc atcgttactg tttcaaatat tcagttgttt    120

cagtacagag tcgccgtgga cctagtgaaa cttggtgtct ttacagcgca gagacgaggg    180

cttatatgta taaaagctgt ccttgattct ggtgtagttt gaggtgtcct tcctatatct    240

gtttttatat tctatataat ggataattac taccatcacc tgcatcaaat tccagtaaat    300

tcacatattg gagaaaatga aattcatttc tacctttctc acttttattt tagcggccgt    360

ttctgtcact gctagttccg atgaagatat cgctcaggtg ccagccgagg ccattattgg    420

atacttggat ttcggaggtg atcatgacat agctttttta ccattcagta acgctaccgc    480

cagtgggcta ttgtttatca acaccactat tgctgaggcg gctgaaaaag agcaaaacac    540

cactttggcg aaaagagagg ctgttgccga cgcttggcac tggttaaatt tgagaccagg    600

ccaaccaatg tacaagagag aggccaacgc tgatgcttgg cactggttgc aactcaagcc    660

aggccaacca atgtactgaa aaatgaccct aaactacttc taaaccctct cgatttcttt    720

cacgttcata caacacctag ttttatttat tttcttttca atctgagtag ttgagttttc    780

gatcactcac atagaactat tttttgccat ttaaataaag tattctctca aatgatgcga    840

tactataata ctctttgcca tatattacat tcattcataa ataggctatg tttctatatc    900

cgtttccgat tctgtctgca agcaaggttc cctatcatta ccggattgtt cactatggtt    960

ggagctc                                                              967


<210> SEQ ID NO 66
<211> LENGTH: 120
<212> TYPE: PRT
<213> ORGANISM: Artificial Sequence
<220> FEATURE:
<223> OTHER INFORMATION: Protein sequence of alpha factor

<400> SEQUENCE: 66

Met Lys Phe Ile Ser Thr Phe Leu Thr Phe Ile Leu Ala Ala Val Ser
 1               5                  10                  15

Val Thr Ala Ser Ser Asp Glu Asp Ile Ala Gln Val Pro Ala Glu Ala
            20                  25                  30

Ile Ile Gly Tyr Leu Asp Phe Gly Gly Asp His Asp Ile Ala Phe Leu
        35                  40                  45

Pro Phe Ser Asn Ala Thr Ala Ser Gly Leu Leu Phe Ile Asn Thr Thr
    50                  55                  60

Ile Ala Glu Ala Ala Glu Lys Glu Gln Asn Thr Thr Leu Ala Lys Arg
65                  70                  75                  80

Glu Ala Val Ala Asp Ala Trp His Trp Leu Asn Leu Arg Pro Gly Gln
                85                  90                  95

Pro Met Tyr Lys Arg Glu Ala Asn Ala Asp Ala Trp His Trp Leu Gln
            100                 105                 110

Leu Lys Pro Gly Gln Pro Met Tyr
        115                 120
```

What is claimed is:

1. A fusion protein comprising the amino acid sequence of mature human IGF-I [as shown in FIG. 12 or a natural allelic variant thereof] *consisting of amino acids residues 20–89 of SEQ ID NO: 48* and, at the N-terminus of the mature *human* IGF-I, a bacterial protein followed by an enzymatic proteolysis site linking the bacterial protein and the mature *human* IGF-I.

* * * * *

UNITED STATES PATENT AND TRADEMARK OFFICE

CERTIFICATE OF CORRECTION

PATENT NO. : RE 39,355 E
APPLICATION NO. : 10/461712
DATED : October 17, 2006
INVENTOR(S) : James M. Lee et al.

It is certified that error appears in the above-identified patent and that said Letters Patent is hereby corrected as shown below:

On the Title page, in the "Assignee": (73) delete the Assignee data and replace as follows:

-- (73) Assignee: Genentech. Inc., South San Francisco,

CA (US) --

Signed and Sealed this

Sixth Day of May, 2008

JON W. DUDAS
*Director of the United States Patent and Trademark Office*